(12) United States Patent
Tan et al.

(10) Patent No.: US 11,955,241 B2
(45) Date of Patent: Apr. 9, 2024

(54) PATHOGENIC BIOMARKERS AND SERUM EXTRACELLULAR VESICULAR BIOMARKERS ASSOCIATED WITH VASCULAR MALFORMATION OF ENDOTHELIAL CELLS, AND USES THEREOF

(71) Applicant: The Regents of the University of California, Oakland, CA (US)

(72) Inventors: Wenbin Tan, Irvine, CA (US); John Stuart Nelson, Irvine, CA (US); Dongbao Chen, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 1346 days.

(21) Appl. No.: 16/430,396

(22) Filed: Jun. 3, 2019

(65) Prior Publication Data

US 2019/0371471 A1     Dec. 5, 2019

Related U.S. Application Data

(60) Provisional application No. 62/679,897, filed on Jun. 3, 2018.

(51) Int. Cl.
| | |
|---|---|
| *G16H 50/30* | (2018.01) |
| *G01N 33/53* | (2006.01) |
| *G01N 33/574* | (2006.01) |
| *G01N 33/68* | (2006.01) |
| *G16B 40/10* | (2019.01) |
| *G16H 50/20* | (2018.01) |

(52) U.S. Cl.
CPC ......... *G16H 50/30* (2018.01); *G01N 33/5308* (2013.01); *G01N 33/5743* (2013.01); *G01N 33/6848* (2013.01); *G16B 40/10* (2019.02); *G16H 50/20* (2018.01); *G01N 2800/20* (2013.01); *G01N 2800/60* (2013.01)

(58) Field of Classification Search
None
See application file for complete search history.

(56) References Cited

PUBLICATIONS

Laquer, Vivian T. et al. "Microarray Analysis of Port Wine Stains before and after Pulsed Dye Laser Treatment." Lasers in surgery and medicine 45.2 (2013): 67-75. Web. (Year: 2013).*
Ferreira R, Santos T, Amar A, Gong A, Chen TC, Tahara SM, Giannotta SL, Hofman FM. Argonaute-2 promotes miR-18a entry in human brain endothelial cells. J Am Heart Assoc. May 16, 2014;3(3):e000968. doi: 10.1161/JAHA.114.000968. (Year: 2014).*
TaqMan® Gene Expression Assays Providing the greatest sensitivity, specificity and reproducibility for quantitative gene expression. (2006) (Year: 2006).*
Fasen, Katrin, Douglas Pat Cerretti, and Uyen Huynh-Do. "Ligand Binding Induces Cbl-Dependent EphB1 Receptor Degradation Through the Lysosomal Pathway." Traffic (Copenhagen, Denmark) 9.2 (2008): 251-266. Web. (Year: 2008).*
Adams et al., Roles of ephrinB ligands and EphB receptors in cardiovascular development: demarcation of arterial/venous domains, vascular morphogenesis, and sprouting angiogenesis. Genes Dev 13:295-306 (1999).
Aoki et al., EphA receptors direct the differentiation of mammalian neural precursor cells through a mitogen-activated protein kinase-dependent pathway. J Biol Chem 279:32643-50 (2004).
Couto et al., Endothelial Cells from Capillary Malformations Are Enriched for Somatic GNAQ Mutations. Plast. Reconstr. Surg. 137, 77e-82e (2016).
Daar I.O., Non-SH2/PDZ reverse signaling by ephrins. Semin Cell Dev Biol 23:65-74 (2012).
Davy et al., Ephrin signaling in vivo: look both ways. Dev Dyn 232:1-10 (2005).
Denzer et al., Exosome: from internal vesicle of the multivesicular body to intercellular signaling device. J. Cell Sci. 113 Pt 19:3365-74 (2000).
Deutsch et al., Trans-Proteomic Pipeline supports and improves analysis of electron transfer dissociation data sets. Proteomics 10:1190-5 (2010).
Dvorak et al., Morphology of delayed type hypersensitivity reactions in man. II. Ultrastructural alterations affecting the microvasculature and the tissue mast cells. Lab Invest 34:179-91 (1976).
Fear et al., Comment to article: B1 and B2: a role for ephrin signaling in port-wine stain Tan et al. Br J Dermatol 177:1601-1611 (2017).
Gao et al., Topical rapamycin systematically suppresses the early stages of pulsed dye laser-induced angiogenesis pathways. Lasers Surg. Med. 46:679-88 (2014).
Gao et al., Topical axitinib suppresses angiogenesis pathways induced by pulsed dye laser. Br. J. Dermatol. 172:669-76 (2015).
Gao et al., Ultrastructural Characterization of Hyperactive Endothelial Cells, Pericytes and Fibroblasts in Hypertrophic and Nodular Port Wine Stain Lesions. Br. J. Dermatol. (2017).
Gerety et al., Symmetrical mutant phenotypes of the receptor EphB4 and its specific transmembrane ligand ephrin-B2 in cardiovascular development. Mol Cell 4:403-14 (1999).
Gerety et al., Cardiovascular ephrinB2 function is essential for embryonic angiogenesis. Development 129:1397-410 (2002).
Goodwin A., In vitro assays of angiogenesis for assessment of angiogenic and antiangiogenic agents. Microvasc Res 74:172-83 (2007).
Gorenberg et al., The Role of Co-chaperones in Synaptic Proteostasis and Neurodegenerative Disease. Front. Neurosci. 11, 248 (2017).
Grewal et al., Annexin A6—A multifunctional scaffold in cell motility. Cell Adh Migr 11, 288-304 (2017).

(Continued)

*Primary Examiner* — Joseph Woitach
*Assistant Examiner* — Jospeh Pulliam
(74) *Attorney, Agent, or Firm* — Gavrilovich, Dodd & Lindsey LLP

(57) ABSTRACT

The disclosure provides for pathogenic biomarkers and serum extracellular vesicular biomarkers that are associated with vascular anomalies and malformation of endothelial cells, and uses thereof, including for diagnosis, prognosis and therapy.

16 Claims, 13 Drawing Sheets

(56) References Cited

PUBLICATIONS

Hashizume et al., Openings between defective endothelial cells explain tumor vessel leakiness. Am. J. Pathol. 156, 1363-80 (2000).
Jiao et al., Ephrins as negative regulators of adult neurogenesis in diverse regions of the central nervous system. Proc Natl Acad Sci U S A 105:8778-83 (2008).
Johnson et al., Development of human embryonic and fetal dermal vasculature. J Invest Dermatol 93:10S-17S (1989).
Kao et al., Ephrin-mediated cis-attenuation of Eph receptor signaling is essential for spinal motor axon guidance. Neuron 71:76-91 (2011).
Kubota et al., Role of laminin and basement membrane in the morphological differentiation of human endothelial cells into capillary like structures. J Cell Biol 107:1589-98 (1988).
Lackmann et al., Eph, a protein family coming of age: more confusion, insight, or complexity? Sci Signal 1:re2 (2008).
Li et al., Tissue-specific venous expression of the EPH family receptor EphB1 in the skin vasculature. Dev Dyn 242:976-88 (2013).
Luks et al., Lymphatic and other vascular malformative/overgrowth disorders are caused by somatic mutations in PIK3CA. J Pediatr 166:1048-54 (2015).
Marquardt et al., Coexpressed EphA receptors and ephrin-A ligands mediate opposing actions on growth cone navigation from distinct membrane domains. Cell 121:127-39 (2005).
Nievergall et al., Eph-dependent cell-cell adhesion and segregation in development and cancer. Cell Mol Life Sci 69:1813-42 (2012).
Noordstra et al., Linking cortical microtubule attachment and exocytosis. F1000Res 6:469 (2017).
Ostasiewicz, et al., Proteome, phosphoproteome, and N309 glycoproteome are quantitatively preserved in formalin-fixed paraffin-embedded tissue and analyzable by high-resolution mass spectrometry. J. Proteome Res. 9:3688-700 (2010).
Pasquale et al., Eph receptor signalling casts a wide net on cell behaviour. Nat Rev Mol Cell Biol 6:462-75 (2005).
Phillips et al., The presynaptic particle web: ultrastructure, composition, dissolution, and reconstitution. Neuron 32: 63-77 (2001).
Saha et al., Cell-cell signaling via Eph receptors and ephrins. Curr Opin Cell Biol 9:534-42 (2007).
Selim et al., Confocal microscopy study of nerves and blood vessels in untreated and treated port wine stains: preliminary observations. Dermatol Surg 30:892-7 (2004).
Shirley et al., Sturge-Weber Syndrome and Port-Wine Stains Caused by Somatic Mutation in GNAQ. N. Engl. J. Med. 368:1971-9 (2013).
Simons et al., Exosomes—vesicular carriers for intercellular communication. Curr. Opin Cell Biol. 21:575-81 (2009).
Six et al., The Notch ligand Delta1 is sequentially cleaved by an ADAM protease and gamma-secretase. Proc. Natl. Acad. Sci. U. S. A. 100:7638-43 (2003).
Six et al., The notch ligand Delta1 recruits Dlg1 at cell-cell contacts and regulates cell migration. J. Biol. Chem. 279, 55818-26 (2004).
Tan et al., Topical rapamycin suppresses the angiogenesis pathways induced by pulsed dye laser: molecular mechanisms of inhibition of regeneration and revascularization of photocoagulated cutaneous blood vessels. Lasers Surg. Med. 44:796-804 (2012).
Tan et al., Sustained activation of c-Jun N-terminal and extracellular signal-regulated kinases in port-wine stain blood vessels. J. Am. Acad. Dermatol. 71, 964-68 (2014).
Tan et al., The somatic GNAQ mutation R183Q) is primarily located in Port Wine Stain blood vessels. J. Am. Acad. Dermatol. 74, 380-83 (2016).
Tan et al., Pathological Alterations Involve the Entire Skin Physiological Milieu in Infantile and Early Childhood Port Wine Stain. Br. J. Dermatol. (2016).
Tan et al., Coexistence of Eph receptor B1 and ephrin B2 in port-wine stain endothelial progenitor cells contributes to clinicopathological vasculature dilatation. Br. J. Dermatol 177(6):1601-1611 (Dec. 2017).
Tsou et al., DIA-Umpire: comprehensive computational framework for data-independent acquisition proteomics. Nat. Methods 12:258-64 (2015).
Wang et al., Molecular distinction and angiogenic interaction between embryonic arteries and veins revealed by ephrin-B2 and its receptor Eph-B4. Cell 93:741-53 (1998).
Watanabe et al., IQGAPs as Key Regulators of Actin-cytoskeleton Dynamics. Cell Struct. Funct. 40, 69-77 (2015).
Wilkinson DG., Regulation of cell differentiation by Eph receptor and ephrin signaling. Cell Adh Migr 8:339-48 (2014).
Yen et al., Ultrastructure of the human dermal microcirculation: the horizontal plexus of the papillary dermis. J Invest Dermatol 66:131-42 (1976).
Yin et al., Activation of PKCα and PI3K Kinases in Hypertrophic and Nodular Port Wine Stain Lesions. Am. J. Dermatopathol. (2016).
Yin et al., Membrane trafficking and exocytosis are upregulated in port wine stain blood vessels. Histol Histopathol 34: 479-490 (May 2019).
Zhao et al., Takada Y et al. Bidirectional ephrinB2-EphB4 signaling controls bone homeostasis. Cell Metab 4:111-21 (2006).

\* cited by examiner

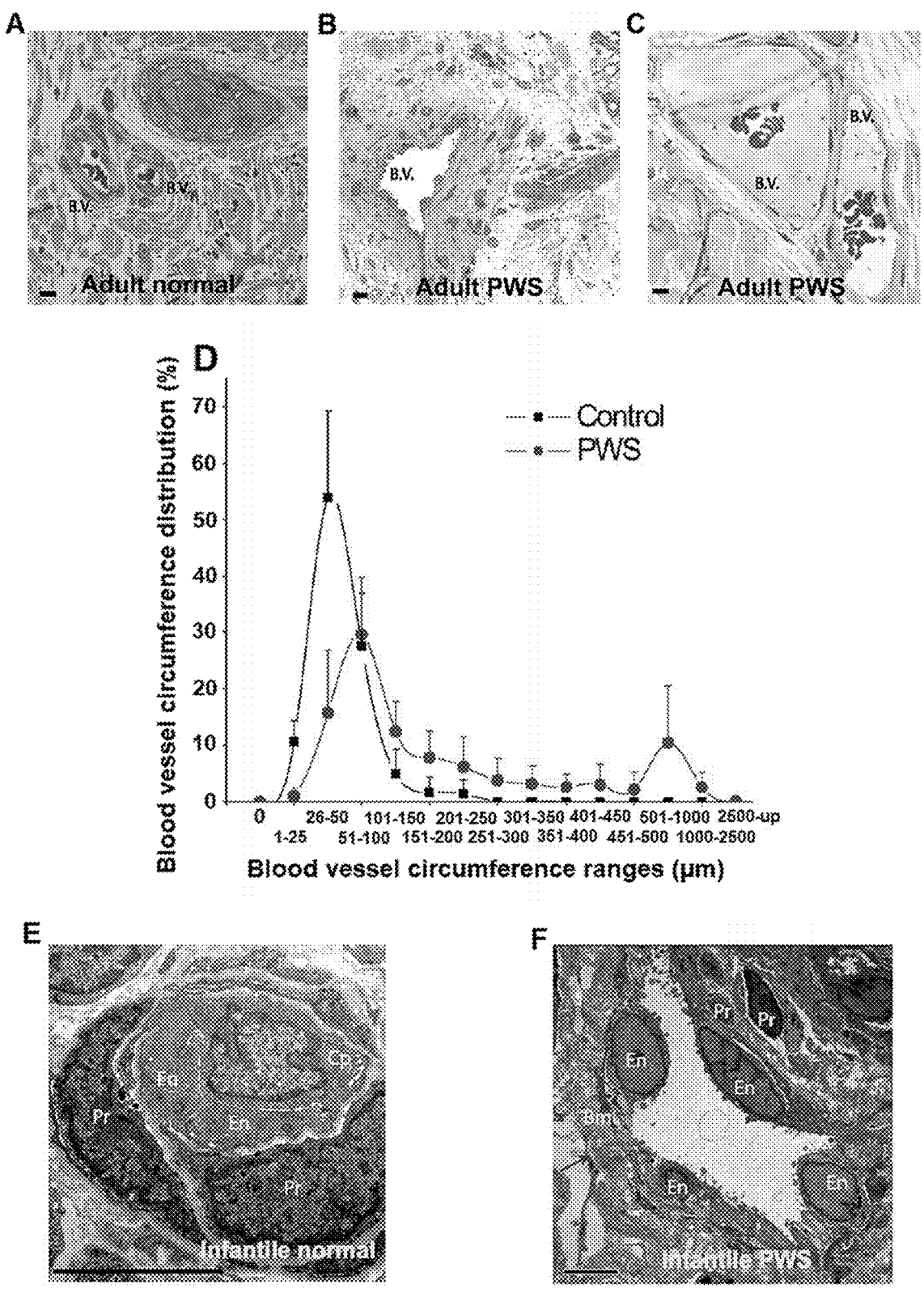
*FIG. 1A-F*

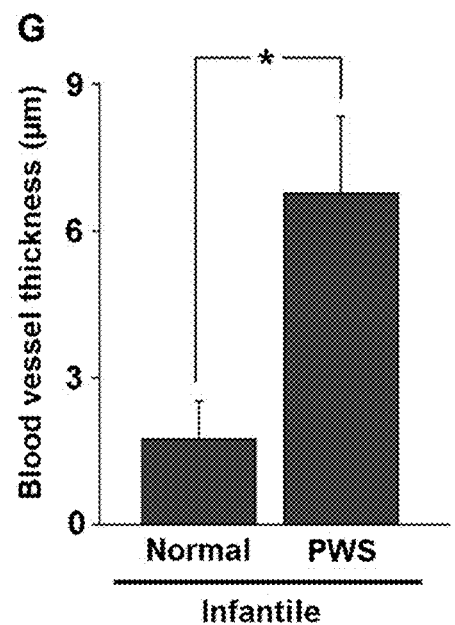
*FIG. 1G*
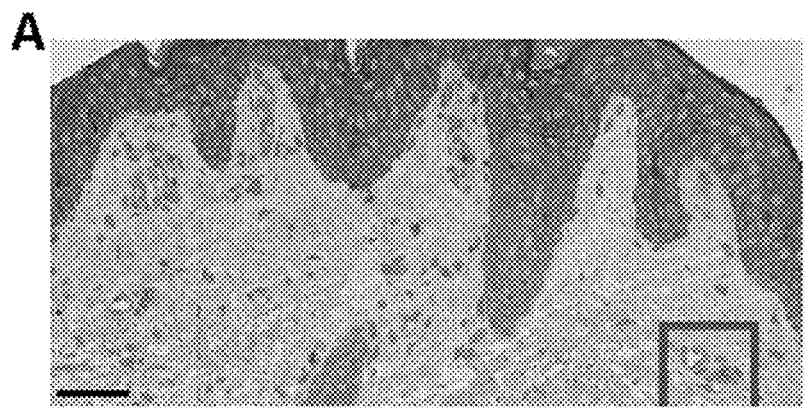
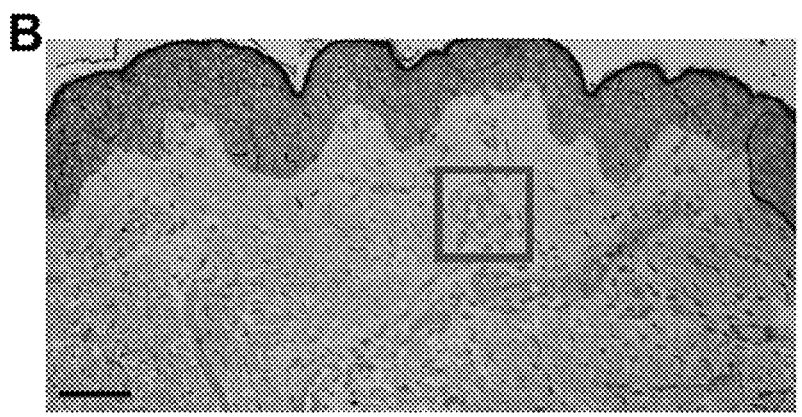
*FIG. 2A-B*

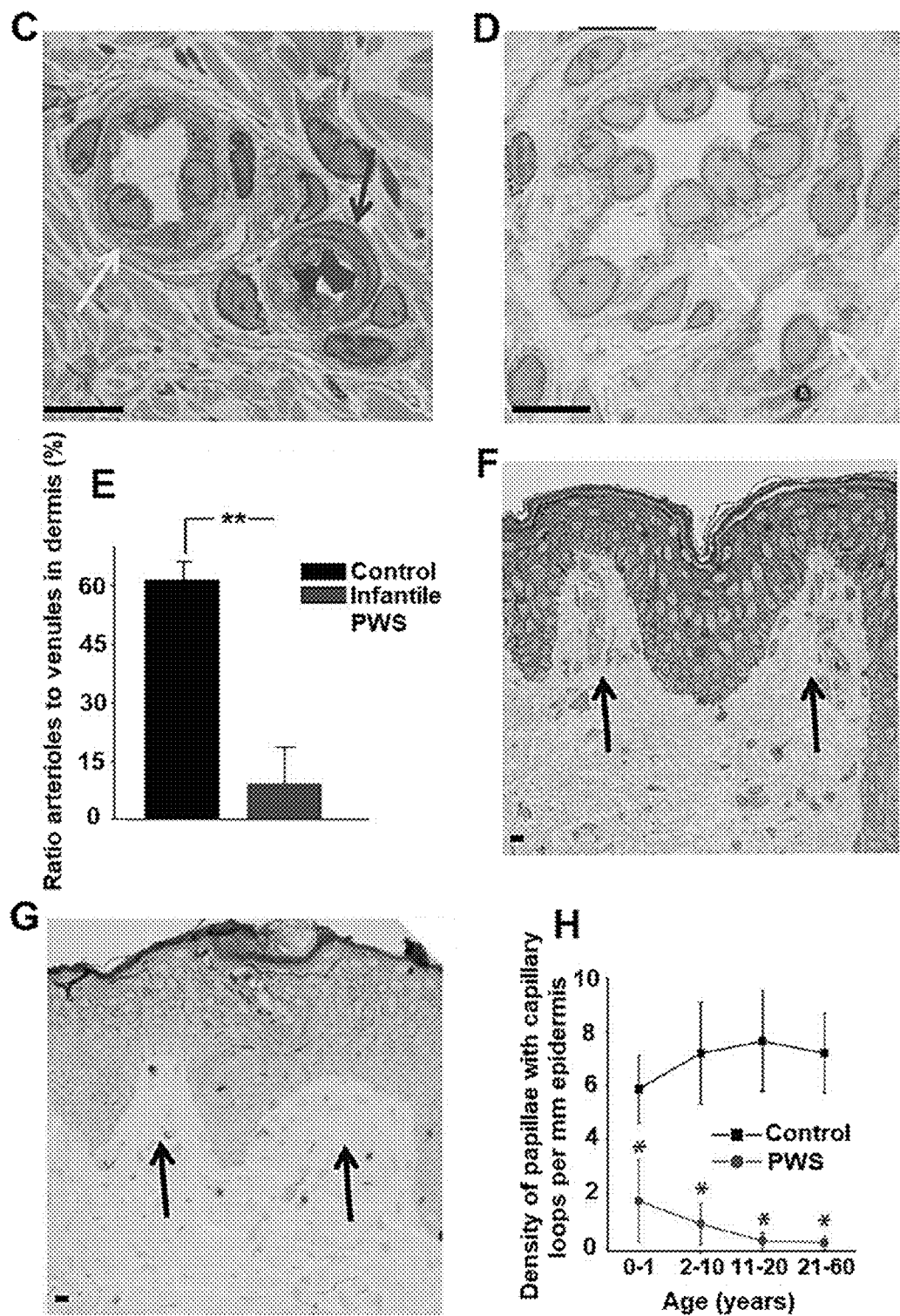
*FIG. 2C-H*

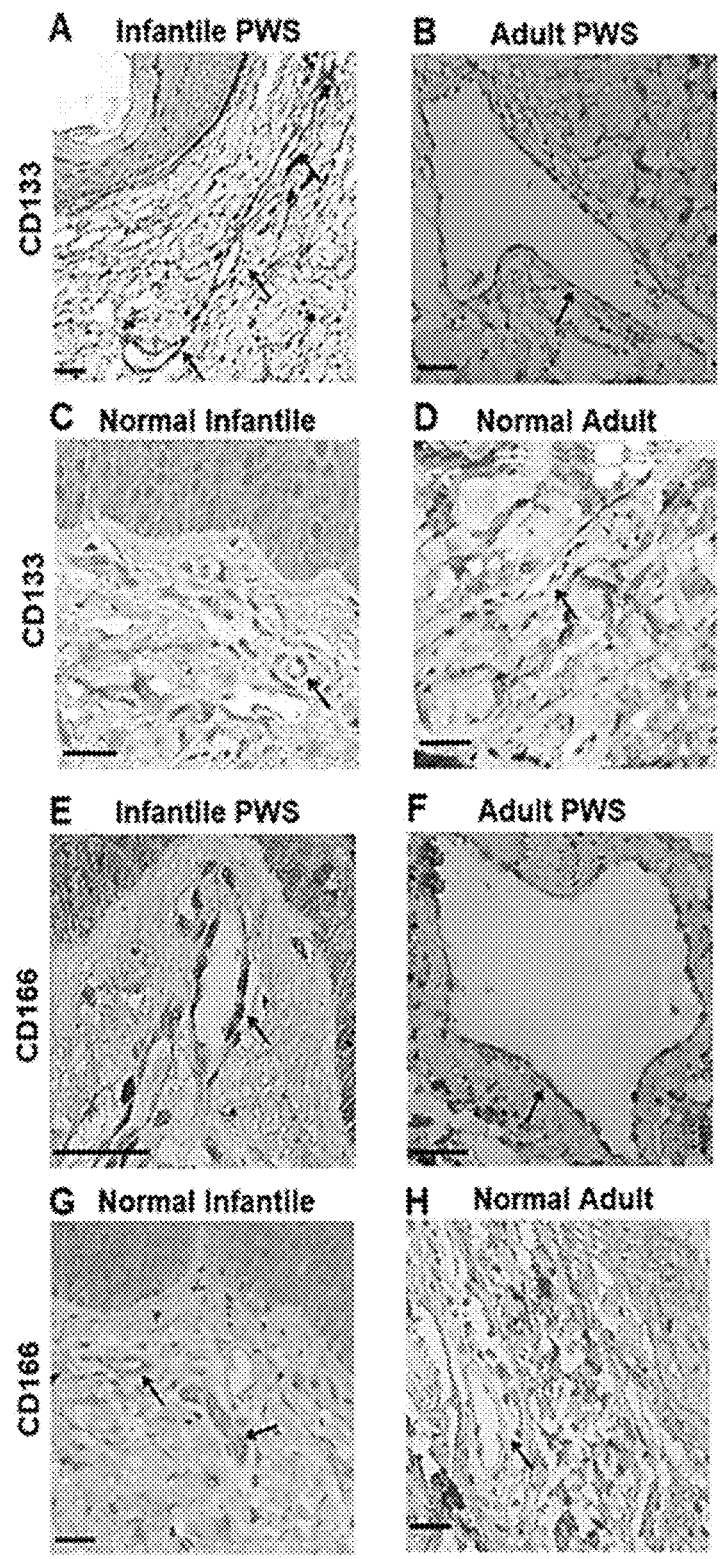
FIG. 3A-H

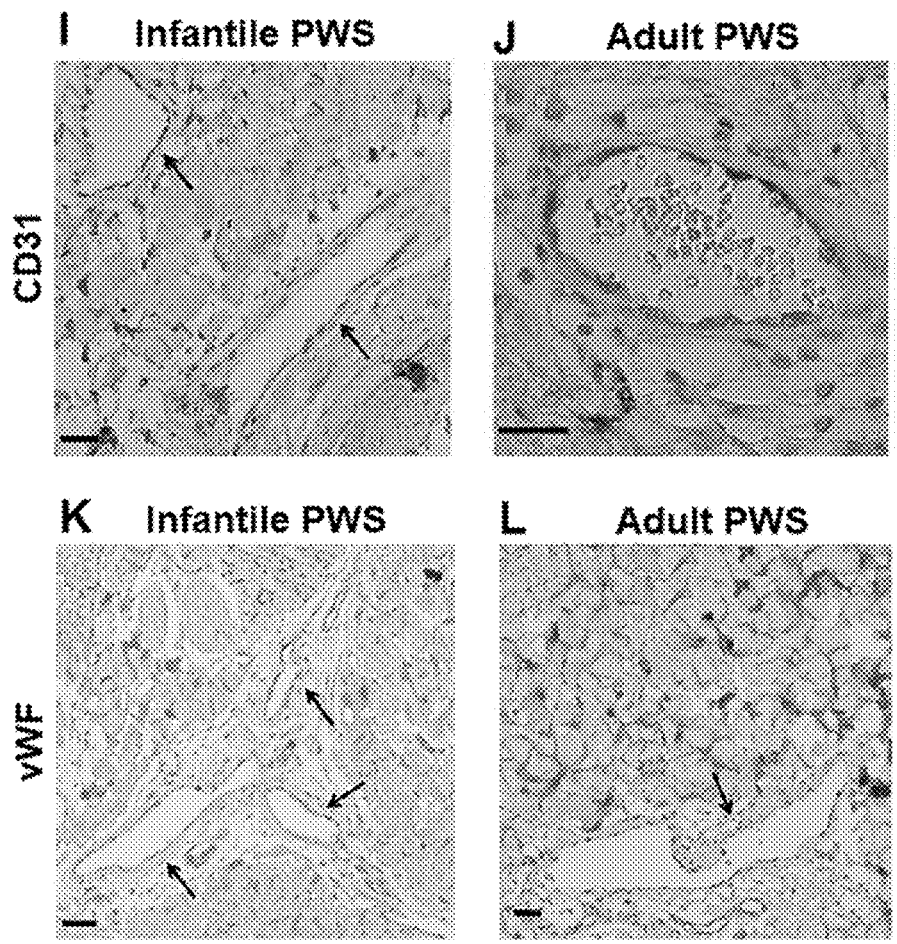
FIG. 3I-L
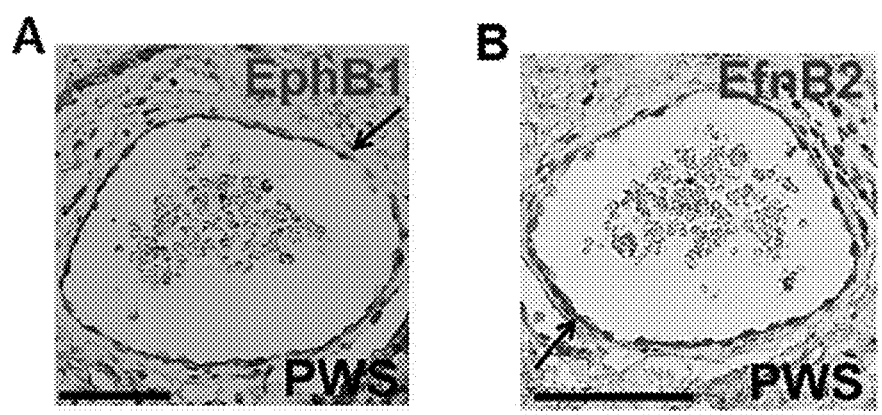
FIG. 4A-B

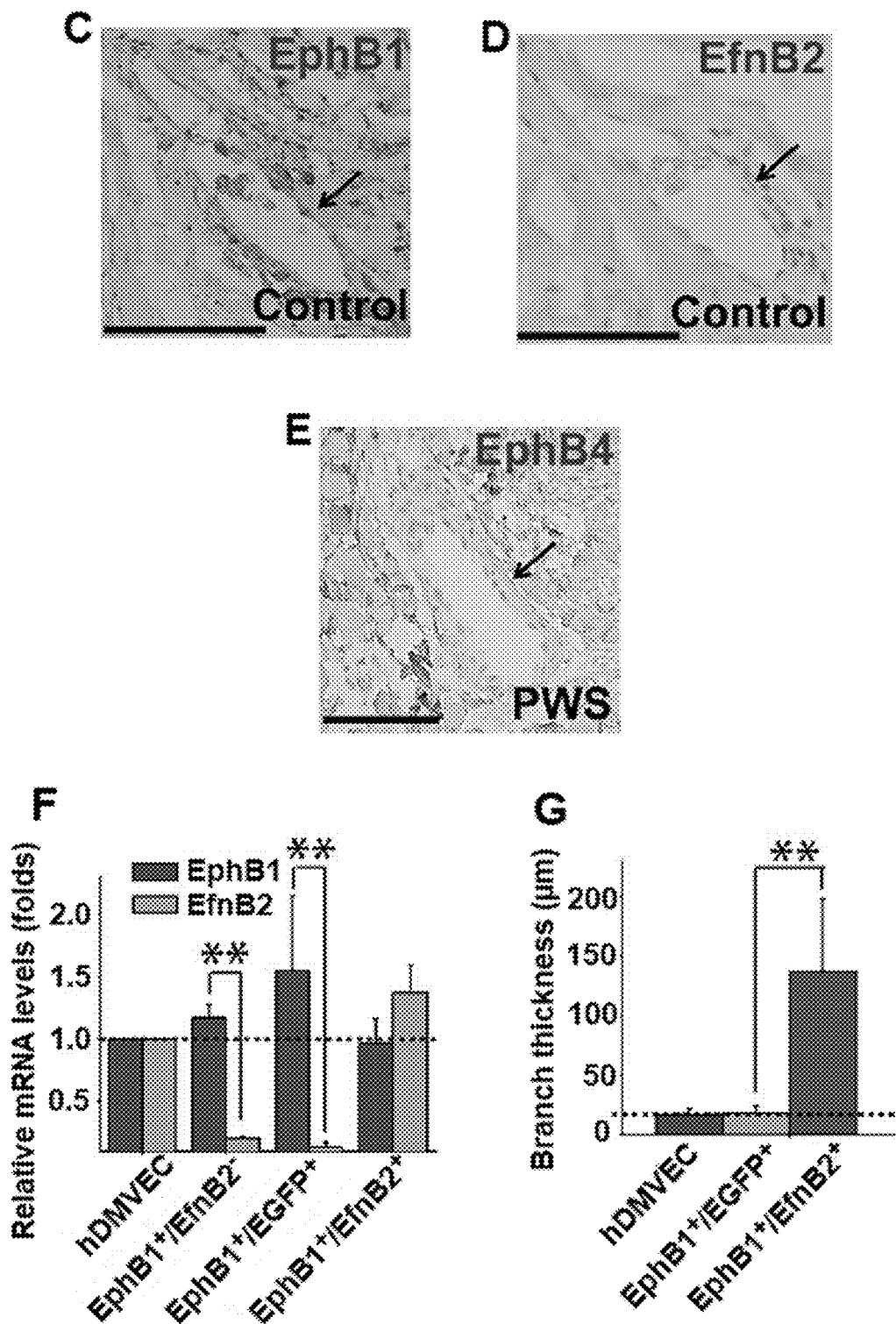
FIG. 4C-G

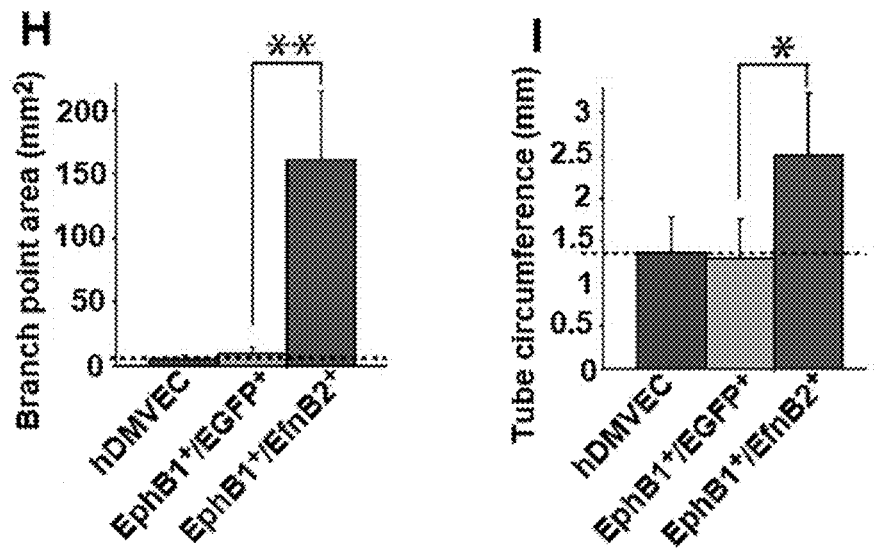
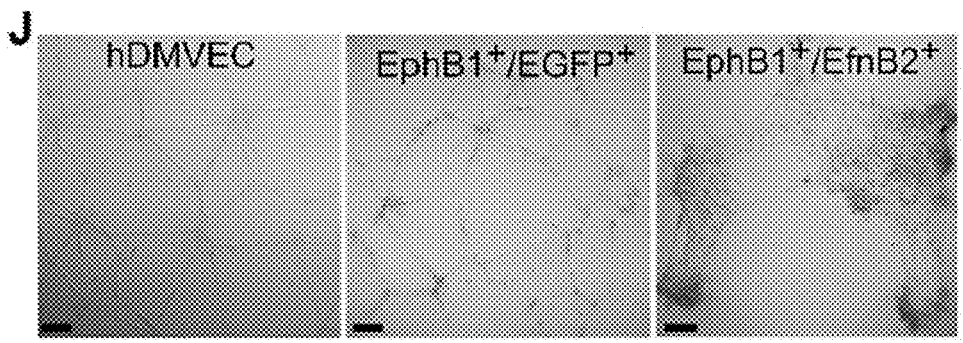
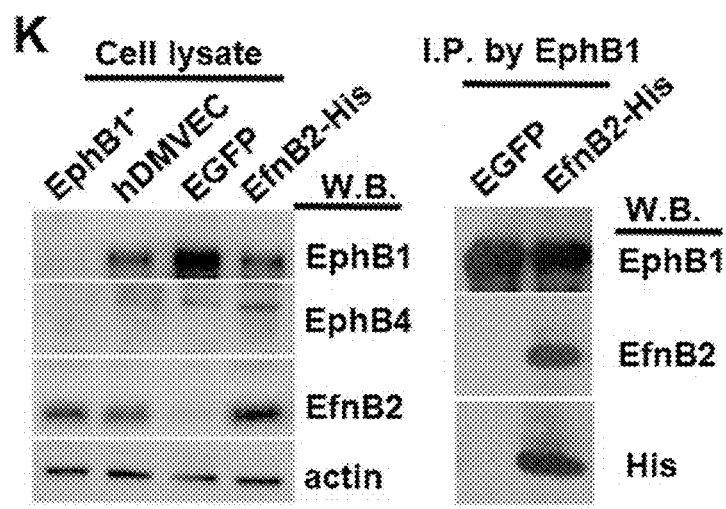
*FIG. 4H-K*

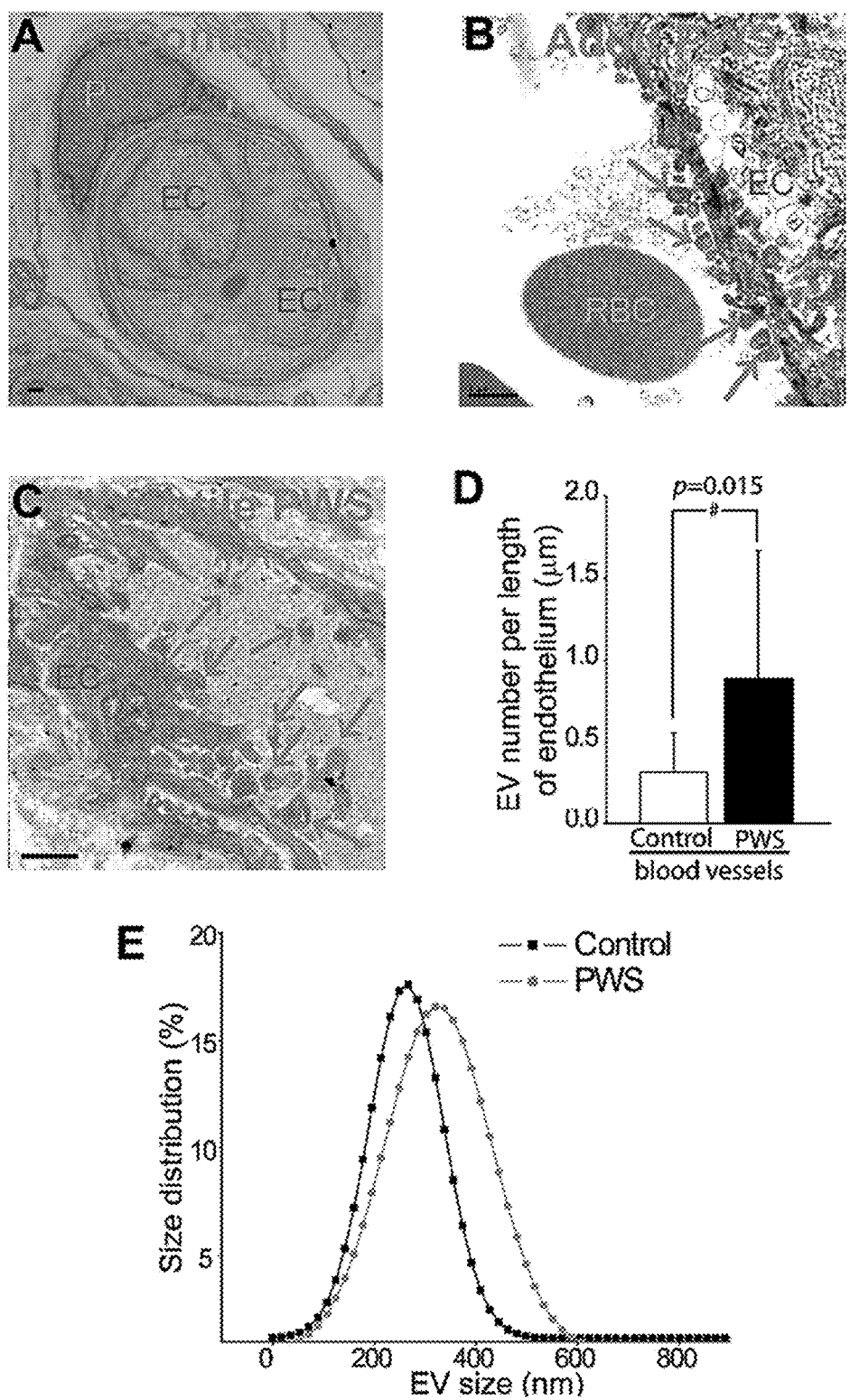
*FIG. 8A-E*

PATHOGENIC BIOMARKERS AND SERUM EXTRACELLULAR VESICULAR BIOMARKERS ASSOCIATED WITH VASCULAR MALFORMATION OF ENDOTHELIAL CELLS, AND USES THEREOF

CROSS REFERENCE TO RELATED APPLICATIONS

This application claims priority under 35 U.S.C. § 119 from Provisional Application Ser. No. 62/679,897, filed Jun. 3, 2018, the disclosure of which is incorporated herein by reference.

GOVERNMENT LICENSE RIGHTS

This invention was made with Government support under Grant Nos. AR059244, AR063766, and AR073172 awarded by the National Institutes of Health, and Grant No. W81XWH-18-1-0096 awarded by the Department of Defense. The Government has certain rights in the invention.

TECHNICAL FIELD

The disclosure provides for pathogenic biomarkers and serum extracellular vesicular biomarkers that are associated with vascular anomalies and malformation of endothelial cells, and uses thereof, including for diagnosis, prognosis and therapy.

BACKGROUND

A vascular anomaly is a disorder with developmental defects in blood vessels which can involve in each type of vasculature. The vascular phenotypes of vascular anomaly are usually characterized by an increase in vessels numbers and their diameters. Port-wine stain (PWS) is a kind of vascular anomaly characterized by progressive dilatation of postcapillary venules, but the molecular pathogenesis remains obscure.

SUMMARY

It was shown herein that PWS blood vessels are immature capillary vasculatures with aberrant expression of stem cell markers CD133 and CD166 and venous and arterial identities EphB1 and Ephrin B2 (EfnB2), which form immature venule-like pathoanatomic vasculatures. The disruption of normal endothelial cell to endothelial cell (EC-EC) interactions by co-existence of EphB1 and EfnB2 contributed to progressive dilatation of PWS vasculatures. The Eph receptor family is the largest subfamily of receptor tyrosine kinases. The Eph receptors are bound by ephrin ligands; receptors and nine ligands have been identified in humans. The receptors have a high degree of homology, as do the ligands, leading to functional redundancy. Ephrin/Eph signaling research focused initially on their role in the development of the central nervous system and topographic mapping. However, ephrins are also important for vascular development and play a role in endothelial differentiation and vascular morphogenesis. The data presented herein shows (1) anatomy of PWS capillaries and expression of developmental markers on ECs in PWS tissue samples, (2) the impact of aberrant ephrin expression on capillary formation in vitro, and (3) the vasculature in pediatric PWS tissue is aberrant, with increased vessel density and significant morphological abnormalities indicative of immature endothelial development (see FIG. 5). It was further found herein, that ECs in PWS tissue expressed CD133/CD166 and CD31 markers, suggesting that the ECs are late-stage endothelial progenitor cells rather than fully differentiated ECs. In other studies, presented herein, it was shown that PWS endothelial cells co-express both venous- and arterial-specific markers (EphB1 and EfnB2, respectively). Accordingly, the studies presented herein provide support that PWS is caused by disruption during development and that this affects EC phenotype. More specifically, that incomplete endothelial differentiation, as evidenced by co-expression of specific markers, underpinned the formation of the defective capillaries.

The disclosure has further identified differentially expressed (DE) proteins in PWS lesions as compared to normal skin using a proteomics approach namely sequential windowed acquisition of all theoretical fragment ion mass spectra (SWATH-MS). In additional studies, it was determined that PWS blood vessels have increased expression of cell membrane trafficking/exocytosis related molecules and that the exocytosis of extracellular vehicles (EVs) was enhanced in PWS blood vessels.

In a particular embodiment, the disclosure provides a method comprising obtaining one or more samples from a subject; determining the expression profile of pathogenic associated biomarkers and/or serum extracellular vesicle (EV) biomarkers that are associated with vascular anomalies or malformations from the subject's one or more samples; comparing the expression profile of pathogenic associated biomarkers and/or serum exosomal biomarkers from the subject's one or more samples with one or more normal control sample; and optionally, indicating that the subject has a vascular anomaly or malformation based upon the expression profile of the biomarkers from the one or more subject's samples differing from the expression profile of the biomarkers from the one or more normal control samples. In a further embodiment, the one or more samples from the subject and normal control are skin tissue biopsy samples and/or EV serum samples. In another embodiment, the one or more normal control samples are from the subject. In yet another embodiment, the one or more normal control samples are not from subject. In a certain embodiment, the pathogenic associated biomarkers and/or serum exosomal biomarkers comprise one or more biomarkers comprising Ephs, Efns, ADAMs, MMPs, STYs, CD31, CD133, CD166, VAT1, IQGAP1, HSC70, clathrin, perlecan, spectrin α1, GDIR1, and/or collagen subtypes 6A1 and 6A3. In a further embodiment, the pathogenic associated biomarkers and/or serum EV biomarkers comprise the biomarkers of Ephs, Efns, ADAMs, MMPs, STYs. CD31, CD133, CD166, VAT1, IQGAP1, HSC70, clathrin, perlecan, spectrin α1, GDIR1, and collagen subtypes 6A1 and 6A3. In yet a further embodiment, the pathogenic associated biomarkers and/or serum EV biomarkers comprise five or more biomarkers listed in Table 4. In another embodiment, the pathogenic associated biomarkers and/or serum EV biomarkers comprise ten or more biomarkers listed in Table 4. In yet another embodiment, the pathogenic associated biomarkers and/or serum EV biomarkers comprise twenty or more biomarkers listed in Table 4. In a particular embodiment, the expression profile of pathogenic associated biomarkers and/or serum EV biomarkers that are associated with vascular anomalies or malformations is determined using one or more techniques comprising FISH, microarray, IHC, sequencing, immunoassay, mass sequencing, SWATH-MS, and quantitative PCR. In another embodiment, the vascular anomalies or malformations are selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma. In a certain embodiment, the vascular anomalies or malformations are selected from AVM, VM, PWS, SWS, and KTWS. In a further embodiment, the vascular anomalies or malformations are PWS. In yet a further embodiment, for method disclosed herein a prognosis for treatment of the vascular anomalies or malformations in a subject is determined based upon a measured difference in the expression profile of the biomarkers from the one or more subject's samples vs. expression profile from the one or more normal control samples.

In a particular embodiment, the disclosure also provides a method comprising: obtaining one or more samples from a subject having vascular anomalies or malformations at a first time point; determining a first expression profile of pathogenic associated biomarkers and/or serum EV biomarkers that are associated with vascular anomalies or malformations from the subject's one or more samples obtained at the first time point; treating the subject with one or more treatments for vascular anomalies or malformations; obtaining one or more samples from the subject at a second time point; determining a second expression profile of pathogenic associated biomarkers and/or serum EV biomarkers that are associated with vascular anomalies or malformations from the subject's one or more samples obtained at the second time point; comparing the first expression profile of pathogenic associated biomarkers and/or serum EV biomarkers with the second expression profile of pathogenic associated biomarkers and/or serum EV biomarkers; and optionally, indicating that the effectiveness of the treatment of the subject with vascular anomalies or malformations based upon an improvement or lack thereof between the first expression profile of the biomarkers with the second expression profile of the biomarkers, wherein an improvement is indicated by the second expression profile of the biomarkers being more similar to an expression profile of a normal control subject vs. the first expression profile, and wherein a lack of improvement is indicated by measuring no difference between the first expression profile of the biomarkers and the second expression profile of the biomarkers, or by the second expression profile being more dissimilar to an expression profile of a normal control subject vs. the first expression profile. In a further embodiment, the one or more samples from the subject and normal control are skin tissue biopsy samples and/or EV serum samples. In yet a further embodiment, the pathogenic associated biomarkers and/or serum EV biomarkers comprise one or more biomarkers comprising Ephs, Efns, ADAMs, MMPs, STYs. CD31. CD133. CD166, VAT1, IQGAP1, HSC70, clathrin, perlecan, spectrin α1, GDIR1, and/or collagen subtypes 6A1 and 6A3. In another embodiment, the pathogenic associated biomarkers and/or serum EV biomarkers comprise the biomarkers of Ephs, Efns, ADAMs, MMPs, STYs, CD31, CD133, CD166, VAT1, IQGAP1, HSC70, clathrin, perlecan, spectrin α1, GDIR1, and collagen subtypes 6A1 and 6A3. In yet another embodiment, the pathogenic associated biomarkers and/or serum EV biomarkers comprise five or more biomarkers listed in Table 4. In a further embodiment, the pathogenic associated biomarkers and/or serum EV biomarkers comprise ten or more biomarkers listed in Table 4. In yet a further embodiment, the pathogenic associated biomarkers and/or serum EV biomarkers comprise twenty or more biomarkers listed in Table 4. In another embodiment, the expression profile of pathogenic associated biomarkers and/or serum EV biomarkers that are associated with vascular anomalies or malformations is determined using one or more techniques comprising FISH, microarray, IHC, sequencing, immunoassay, mass sequencing, SWATH-MS, and quantitative PCR. In a certain embodiment, the vascular anomalies or malformations are selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma. In a further embodiment, the vascular anomalies or malformations are selected from AVM, VM, PWS, SWS, and KTWS. In yet a further embodiment, the vascular anomalies or malformations are PWS. In a particular embodiment, the one or more treatments inhibit the expression of Ephs, Efns, ADAMs, MMPs, STYs, CD31, CD133, CD166, VAT1, IQGAP1, HSC70, clathrin, perlecan, spectrin α1, and/or GDIR1, increases the expression of collagen subtypes 6A1 and 6A3, and/or inhibits/increases expression of one or more biomarkers listed in Table 4. In another embodiment, the one or more treatments are encapsulated in an exosome. In yet another embodiment, the one or more treatments are small molecule drugs, gene silencing agents or surface targeting ligands. In a further embodiment, the gene silencing agents are selected from antisense oligonucleotides, ribozymes, RNA interference, microRNAs, and CRISPR. In yet a further embodiment, the surface targeting ligands is selected from antibodies, antibody fragments, and nanoparticles. In a certain embodiment, the surface targeting ligands bind or complex with CD133, CD166, Ephs, and/or Efns. In another embodiment, the one or more treatments are selected from pulsed dye laser, surgery, radiation, and freezing.

In a particular embodiment, the disclosure further provides a method comprising: obtaining one or more samples from a subject having vascular anomalies or malformations at a first time point; determining a first expression profile of pathogenic associated biomarkers and/or serum EV biomarkers that are associated with vascular anomalies or malformations from the subject's one or more samples obtained at the first time point; obtaining one or more samples from the subject at a second time point; determining a second expression profile of pathogenic associated biomarkers and/or serum EV biomarkers that are associated with vascular anomalies or malformations from the subject's one or more samples obtained at the second time point; comparing the first expression profile of pathogenic associated biomarkers and/or serum EV biomarkers with the second expression profile of pathogenic associated biomarkers and/or serum EV biomarkers; and optionally, indicating whether the vascular anomalies or malformations are progressing or regressing based upon an improvement or lack thereof between the first expression profile of the biomarkers with the second expression profile of the biomarkers, wherein an improvement is indicated by the second expression profile of the biomarkers being more similar to an expression profile of a normal control subject vs. the first expression profile, and wherein a lack of improvement is indicated by measuring no difference between the first expression profile of the biomarkers and the second expression profile of the biomarkers, or by the second expression profile being more dissimilar to an expression profile of a normal control subject vs. the first expression profile. In another embodiment, the one or more samples from the subject and normal control are skin tissue biopsy samples and/or EV serum samples. In yet another embodiment, the pathogenic associated biomarkers and/or serum EV biomarkers comprise one or more biomarkers comprising Ephs, Efns, ADAMs, MMPs, STYs, CD31, CD133, CD166, VAT1, IQGAP1, HSC70, clathrin, perlecan, spectrin α1, GDIR1, and/or collagen subtypes 6A1 and 6A3. In a further embodiment, the pathogenic associated biomarkers and/or serum EV biomarkers comprise the biomarkers of Ephs, Efns, ADAMs, MMPs, STYs. CD31, CD133, CD166, VAT1, IQGAP1, HSC70, clathrin, perlecan, spectrin α1, GDIR1, and collagen subtypes 6A1 and 6A3. In yet a further embodiment, the pathogenic associated biomarkers and/or serum EV biomarkers comprise five or more biomarkers listed in Table 4. In another embodiment, the pathogenic associated biomarkers and/or serum EV biomarkers comprise ten or more biomarkers listed in Table 4. In yet another embodiment, the pathogenic associated biomarkers and/or serum EV biomarkers comprise twenty or more biomarkers listed in Table 4. In a certain embodiment, the expression profile of pathogenic associated biomarkers and/or serum EV biomarkers that are associated with vascular anomalies or malformations is determined using one or more techniques comprising FISH, microarray, IHC, sequencing, immunoassay, mass sequencing, SWATH-MS, and quantitative PCR. In another embodiment, the vascular anomalies or malformations are selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma. In yet another embodiment, the vascular anomalies or malformations are selected from AVM, VM, PWS, SWS, and KTWS. In a particular embodiment, the vascular anomalies or malformations are PWS.

In another embodiment, the disclosure provides a method of measuring the expression profile of pathogenic associated biomarkers and/or serum EV biomarkers from a subject suspected of having or having a vascular anomaly or malformation with control samples, comprising: obtaining a skin tissue biopsy sample(s) and/or EV serum sample(s) from a subject suspected of having a vascular anomaly or malformation; measuring the expression profile of a set of seven or more pathogenic associated biomarkers and/or serum extracellular vesicles (EV) biomarkers from sample(s) obtained from the subject, wherein the set of pathogenic associated biomarkers and/or serum EV biomarkers is selected from Ephs, Efns, ADAMs, MMPs, STYs, CD31, CD133, CD166, CALM, ANXA1, MIME, DERM, PPIA, ANXA5, SUCB2, CO4A, TBB4B, COX2, CO6A3, TBA1B, ENOA, KPYM, ATPB, KV201, ACTBL, CO6A1, PRELP, IGHG1, THIO, TBB5, PGK1, ACTBM, LUM, POTEF, LAC7, TBA4A, APOA1, CBPA3, PGS2, CMA1, DSG1, TRYB2, LDHA, HSP71, TPIS, POSTN, POTEJ, LEG3, HSPB1, RLA2, PRDX6, CACP, ML12B, E9PBV3, K1C9, UBA1, K2C6B, IMB1, CAN1, Septin-7, NPM, FACR2, FBLN2, NDUAD, VAT1, HNRPU, ADT3, RL13A, ACADV, G6PI, PLEC, HNRPC, AL3A2, IF5A1, GDIR1, VTDB, TKT, TCPB, C1QBP, K2C3, CAPZB, GANAB, ANXA6, PTBP1, K2C1B, F16P1, CNDP2, MOES, CYB5, PRDBP, EHD2, PHB, CDC42, RTN3, CISY, SPTBN1, HEP2, ACOC, CD44, CLH1, CALL5, IQGA1, ECHA, MYO1C, HSC70, TRY6, ANXA7, ASPN, U2AF1, FIBB, PGAM2, CAP1, SERPH, RL36, RS12, clatharin, perlecan, spectrin α1, wherein the set of seven or more pathogenic associated biomarkers and/or serum extracellular vesicles (EV) biomarkers comprises at least VAT1, IQGAP1, HSC70, CLH1, perlecan, spectrin α1, and GDIR1. In yet a further embodiment, the set of seven or more pathogenic associated biomarkers and/or serum EV biomarkers further comprise one or more biomarkers selected from Ephs, Efns, ADAMs, MMPs, STYs, CD31, CD133, CD166, VDBP, ANXA1, CO6A1 and/or CO6A3. In another embodiment, the expression profile of the set of pathogenic associated biomarkers and/or serum EV biomarkers is measured using sequential windowed acquisition of all theoretical fragment ion mass spectra (SWATH-MS), immunohistochemistry, immunoblot, and/or transmission electron microscopy. In yet a further embodiment, the subject is suspected of having or has a vascular anomaly or malformation selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma. In yet another embodiment, a method disclosed herein further comprises comparing the expression profile of the set pathogenic associated biomarkers and/or serum EV biomarkers from the subject's skin tissue biopsy sample(s) and/or EV serum sample(s) with the expression profile of the same set pathogenic associated biomarkers and/or serum EV biomarkers from control skin tissue biopsy sample(s) and/or EV serum sample(s) that do not have a vascular anomaly or malformation. In a further embodiment, a method disclosed herein further comprises indicating that the subject is a candidate for treatment with a pulsed dye laser or intense pulsed light, based upon a significant difference in the expression profile of the set biomarkers from the subject samples in comparison with control skin tissue biopsy sample(s) and/or EV serum sample(s).

In a particular embodiment, the disclosure provides a method comprising: treating a subject having vascular anomalies or malformations with one or more treatments for vascular anomalies or malformations; obtaining a skin tissue biopsy sample(s) and/or EV serum sample(s) from a subject at the site of the vascular anomaly or malformation; measuring the expression profile of a set of seven or more pathogenic associated biomarkers and/or serum extracellular vesicles (EV) biomarkers from sample(s) obtained from the subject, wherein the set of pathogenic associated biomarkers and/or serum EV biomarkers is selected from Ephs, Efns, ADAMs, MMPs, STYs, CD31, CD133, CD166, CALM, ANXA1, MIME, DERM, PPIA, ANXA5, SUCB2, CO4A, TBB4B, COX2, CO6A3, TBA1B, ENOA, KPYM, ATPB, KV201, ACTBL, CO6A1, PRELP, IGHG1, THIO, TBB5, PGK1, ACTBM, LUM, POTEF, LAC7, TBA4A, APOA1, CBPA3, PGS2, CMA1, DSG1, TRYB2, LDHA, HSP71, TPIS, POSTN, POTEJ, LEG3, HSPB1, RLA2, PRDX6, CACP, ML12B, E9PBV3, K1C9, UBA1, K2C6B, IMB1, CAN1, Septin-7, NPM, FACR2, FBLN2, NDUAD, VAT1, HNRPU, ADT3, RL13A, ACADV, G6PI, PLEC, HNRPC, AL3A2, IF5A1, GDIR1, VTDB, TKT, TCPB, C1QBP, K2C3, CAPZB, GANAB, ANXA6, PTBP1, K2C1B, F16P1, CNDP2, MOES, CYB5, PRDBP, EHD2, PHB, CDC42, RTN3, CISY, SPTBN1, HEP2, ACOC, CD44, CLH1, CALL5, IQGA1, ECHA, MYO1C, HSC70, TRY6, ANXA7, ASPN, U2AF1, FIBB, PGAM2, CAP1, SERPH, RL36, RS12, clathrin, perlecan, spectrin α1, wherein the set of seven or more pathogenic associated biomarkers and/or serum extracellular vesicles (EV) biomarkers comprises at least VAT1, IQGAP1, HSC70, CLH1, perlecan, spectrin α1, and GDIR1; comparing the expression profile of the set pathogenic associated biomarkers and/or serum EV biomarkers from the subject's skin tissue biopsy sample(s) and/or EV serum sample(s) with the expression profile of the same set pathogenic associated biomarkers and/or serum EV biomarkers from control skin tissue biopsy sample(s) and/or EV serum sample(s) that do not have a vascular anomaly or malformation; indicating that the treatment for vascular anomalies or malformations in the subject was effective based upon measuring an improvement in the expression levels of the set of pathogenic associated biomarkers and/or serum EV biomarkers in the subject's samples, wherein an improvement is indicated by the expression profile of the biomarkers of the subject's sample being similar to or comparable with the expression profile of the same set pathogenic associated biomarkers and/or serum EV biomarkers from control skin tissue biopsy sample(s) and/or EV serum sample(s) that do not have a vascular anomaly or malformation, and wherein a lack of improvement is indicated by the expression profile of the biomarkers of the subject's sample being not similar to or not comparable with the expression profile of the same set pathogenic associated biomarkers and/or serum EV biomarkers from control skin tissue biopsy sample(s) and/or EV serum sample(s) that do not have a vascular anomaly or malformation. In yet another embodiment, the set of seven or more pathogenic associated biomarkers and/or serum EV biomarkers further comprise one or more biomarkers selected from Ephs, Efns, ADAMs, MMPs, STYs, CD31, CD133, CD166, VDBP, ANXA1, CO6A1 and/or CO6A3. In a further embodiment, the expression profile of the set of pathogenic associated biomarkers and/or serum EV biomarkers is measured using sequential windowed acquisition of all theoretical fragment ion mass spectra (SWATH-MS), immunohistochemistry, immunoblot, and/or transmission electron microscopy. In yet a further embodiment, the subject has a vascular anomaly or malformation selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma. In another embodiment, the one or more treatments are small molecule drugs, gene silencing agents or surface targeting ligands. In a further embodiment, the gene silencing agents are antisense oligonucleotides, ribozymes, RNA interference, microRNAs, and/or CRISPR. In yet a further embodiment, the surface targeting ligands bind or complex with CD133, CD166, EphB1, and/or EfnB2. In another embodiment, the small molecule drugs or therapies inhibit or disrupt EphB1/EfnB2 signaling pathways. In yet another embodiment, the small molecule drugs or therapies inhibit or disrupt or suppress exocytosis from lesional vasculatures by inhibiting or disrupting the expression of exocytotic proteins. In a further embodiment, the one or more treatments are pulsed dye laser, intense pulsed light, surgery, radiation, and/or freezing. In a further embodiment, a method disclosed herein further comprises treating a subject having vascular anomalies or malformations with one or more treatments for vascular anomalies or malformations; obtaining a second skin tissue biopsy sample(s) and/or EV serum sample(s) from the subject after treatment, where the skin tissue biopsy sample(s) and/or EV serum sample(s) are from the same general area as the sample(s) obtained prior to treatment; measuring a second expression profile of the set of seven or more pathogenic associated biomarkers and/or serum extracellular vesicles (EV) biomarkers from the subject's skin tissue biopsy sample(s) and/or EV serum sample(s) obtained after treatment; comparing the expression profile of the set of pathogenic associated biomarkers and/or serum EV biomarkers prior to treatment with the second expression profile of the set pathogenic associated biomarkers and/or serum EV biomarkers after treatment, wherein the same set of pathogenic associated biomarkers and/or serum EV biomarkers are compared between the expression profiles; and indicating whether the treatment for the vascular anomalies or malformations was effective based upon an improvement in the second expression profile for the biomarkers after treatment over the expression profile of the biomarkers prior to treatment, wherein an improvement is indicated by the second expression profile of the biomarkers being more similar to an expression profile of a normal control subject vs. the expression profile of the set of biomarkers prior to treatment, and wherein a lack of improvement is indicated by measuring little to no difference between the expression profile of the biomarkers prior to treatment and the second expression profile of the biomarkers. In a further embodiment, the subject has a vascular anomaly or malformation selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma. In yet a further embodiment, the one or more treatments for vascular anomalies or malformations are small molecule drugs that inhibit or disrupt EphB1/EfnB2 signaling pathways. In another embodiment, the one or more treatments for vascular anomalies or malformations are small molecule drugs that inhibit or disrupt or suppress exocytosis from lesional vasculatures by inhibiting or disrupting the expression of exocytotic proteins.

DESCRIPTION OF DRAWINGS

FIG. 1A-G Thick- and thin-walled blood vessels in adult and infant port-wine stain (PWS) lesions. (A) Normal blood vessels (b.v.) in adjacent normal skin from an adult with PWS. (B, C) Thick- and thin-walled PWS blood vessels from adults with PWS. (D) PWS blood vessel circumference distribution vs. normal dermal vasculatures (four patients with PWS and four normal adult participants). (E) Electron microscopy (EM) showed a normal capillary in adjacent normal skin from an infant with PWS. En, endothelial cell; Pr, pericyte; Cp, capillary. (F) EM showed an ectatic, thick walled blood vessel with replication of the basement membranes in PWS from the same subject as in (E). Bm, basement membrane. The arrow indicates the blood vessel wall. (G) Infantile PWS blood vessels showed a significantly thicker blood vessel wall compared with normal dermal blood vessels from the same subjects (n=4). Scale bar=5 µm. *$P<0.05$ vs. control.

FIG. 2A-I presents multiple developmental impairments of infant port-wine stain (PWS) vasculatures. (A) Semi-thin section showed normal adjacent skin from an infant with PWS. (B) Semi-thin section showed PWS lesional skin from the same subject as in (A). Scale bar=20 µm. (C) A normal venule (yellow arrow) and arteriole (red arrow) from the red-boxed area in (A). (D) PWS pathoanatomical venule-like vasculatures (yellow arrows) from the red-boxed area in (B). Scale bar=5 µm. (E) The ratio of arteriole to venule-like vasculatures in infantile PWS lesions was significantly reduced compared with normal adjacent skin from the same subjects (n=4). (F) Normal formation of capillary loop (black arrows) in adjacent normal skin from an infant with PWS. (G) Defects in capillary loop formation along with normal development of epidermal rete ridges in PWS from the same subject as in (D). Scale bar=5 µm. (H) Quantitative analysis of the density of papillae containing capillary loops per mm epidermis in patients with PWS vs. normal subjects among groups of different ages. (I) Reduction of capillary loops and rete ridges in PWS flat reddish macular, protuberant hypertrophic areas and nodules from the same subject. Scale bar=100 μm. **P<0.01 and *P<0.05 vs. the control groups in (E) and (H).

FIG. 3A-L shows port-wine stain (PWS) endothelial cells (ECs) presented stemness phenotypes of CD133$^+$/CD166$^+$ in non-nodular lesions. (A-H) Expression of CD133 and CD166 in infant and adult PWS and normal subjects. (I-L) PWS ECs expressed EC markers CD31 and von Willebrand factor (vWF). Positive stain is diaminobenzidine (DAB) (brown). Scale bar=50 μm. Arrows indicate blood vessels.

FIG. 4A-K demonstrates that port-wine stain (PWS) endothelial cells (ECs) showed dual arterial and venous identities of co-expression of Eph receptor B1 (EphB1) and ephrin B2 (EfnB2). (A, B) PWS ECs were EphB1$^+$ and EfnB2$^+$. (C, D) A normal dermal venule showed expression of EphB1 but not EfnB2. (E) PWS ECs were EphB4$^-$. (F) Relative mRNA levels of EphB1 and EfnB2 in selected normal human dermal microvascular endothelial cell (hDMVEC) subtypes. (G-I) Forced co-expression of EphB1 and EfnB2 in normal hDMVECs showed a significant increase in (G) branch thickness, (H) branch point area and (I) tube circumference of the capillary tubes formed in vitro compared with controls. (J) PWS blood vessel-like phenotypes were observed in EphB1$^+$/EfnB2$^+$ but not in wild-type and EphB1$^+$/EGFP$^+$ control hDMVECs in an in vitro capillary tube formation assay at 12 h after cell plating. Positive stain is diaminobenzidine (DAB; brown). Scale bar=100 μm. *P<0.05, ** P<0.01 vs. control. The arrows indicate blood vessels. (K) Left panel, detection of expression of EphB1, EphB4, b-actin and EfnB2 by Western blot (W.B.) in various hDMVEC subpopulations. hDMVEC, heterogeneous population prior to EfnB2-Fc selection; EphB1$^-$ hDMVEC, the remaining hDMVEC subpopulation after EfnB2-Fc selection; enhanced green fluorescent protein (EGFP) or EfnB2-His, overexpression of EGFP or EfnB2 in the EfnB2-Fc selected hDMVEC subpopulation. Right panel, an anti-EphB1 antibody was used to immunoprecipitate EphB1 from cell lysate and EfnB2 was detected from the immunoprecipitated protein complex using an anti-EfnB2 or anti-His antibody.

FIG. 8A-E provides for the exocytosis of EVs in blood vessels of PWS and normal skin demonstrated by TEM. (A) normal ECs. EVs (red arrows) were released from an adult PWS EC (B), and an infantile PWS EC blood vessel (C). P, pericyte; RBC, red blood cells; EC, endothelial cell. (D) Quantitative analysis of the number of released EVs from PWS ECs as compared to control (n=6 subjects). (E) Size distribution of released EVs from PWS ECs as compared to control (n=6 subjects).

DETAILED DESCRIPTION

Figure 2I:
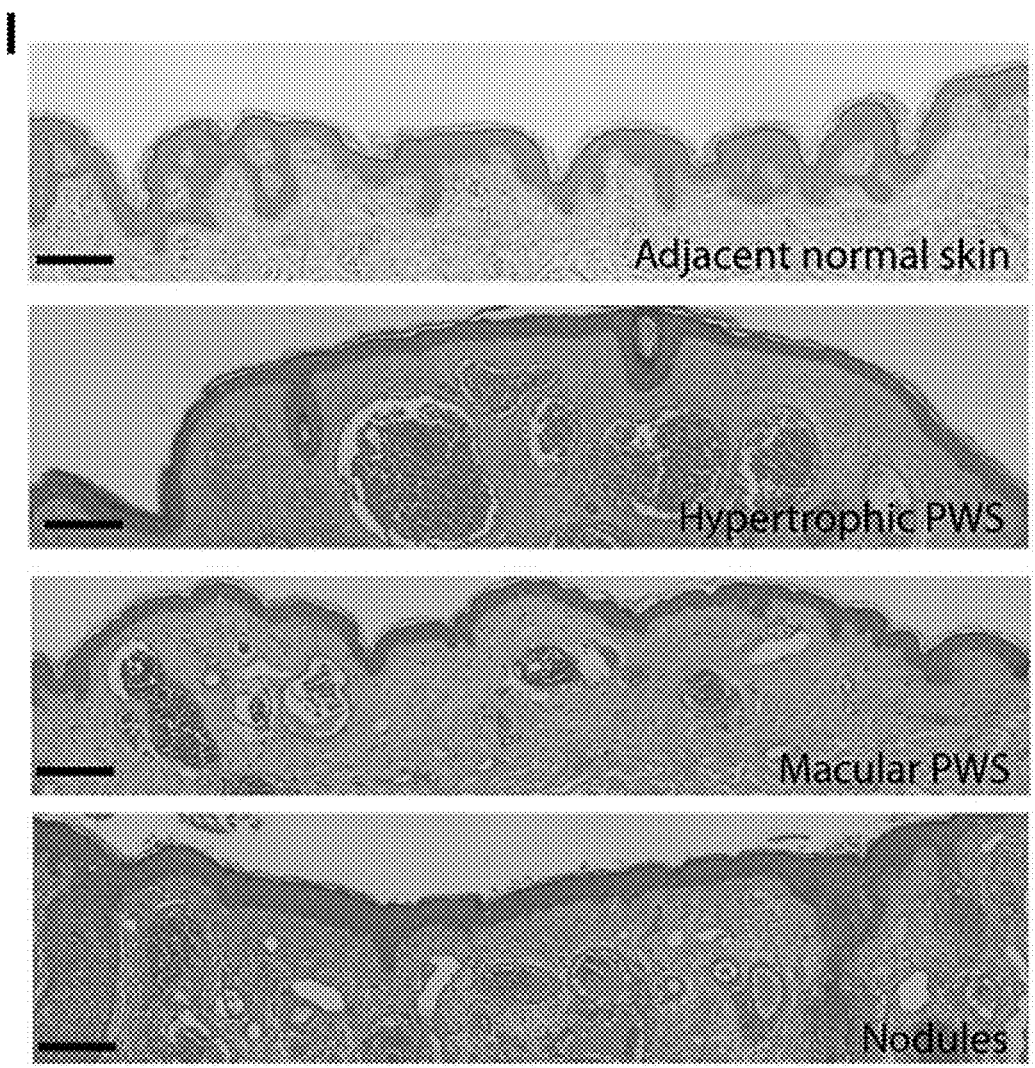

As used herein and in the appended claims, the singular forms "a," "an," and "the" include plural referents unless the context clearly dictates otherwise. Thus, for example, reference to "a biomarker" includes a plurality of biomarkers and reference to "the port wine stain lesion" includes reference to one or more port wine stain lesions and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

A "disorder" or "disease" is any condition that would benefit from treatment with the compositions and/or methods of the disclosure. An example of disorders and diseases that can be treated with the compositions and/or methods disclosed herein, includes vascular malformation of endothelial tissue.

An "effective amount" refers to an amount effective, at dosages and for periods of time necessary, to achieve the desired therapeutic or prophylactic result.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "substantially similar" or "substantially the same." as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by the values (e.g., $K_d$ values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

As used herein, "treatment" refers to clinical intervention in an attempt to alter the natural course of the individual or cell being treated and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, biomarkers disclosed herein are used to monitor the effectiveness of a therapy for the treatment of a disease or disorder.

Extracellular vesicles (EVs) are cell-derived vesicles with a closed double-layer membrane structure. According to their size and density, EVs mainly include exosomes (30-150 nm), micro vesicles (MVs) (100-1000 nm), and apoptotic bodies or cancer related oncocomes (1-10 μm). Exosomes include multi-vesicle body (MVB)-derived EVs carrying specific markers such as CD63, CD9, CD81 and/or TSG101. EVs exist in virtually all body fluids of human, animals, bacteria, and plants, such as blood, urine, saliva, beer, milk, etc. EVs and exosomes are able to carry various molecules, such as proteins, lipids and RNAs on their surface as well as within their lumen. The EV and exosomal surface proteins can mediate organ-specific homing of circulating EVs and exosomes. As used herein, the term "extracellular vesicles" or "'EVs'" includes all cell-derived vesicles with a closed double-layer membrane structure derived from multivescular bodies or from the plasma membrane, including exosomes, microvesicles, and oncocomes.

Port wine stain (PWS) is a congenital vascular malformation resulting from differentiation impaired endothelial cells (ECs) in human skin with a progressive dilatation of immature venule like vasculatures. The prevalence is estimated at 3-5 children per 1,000 live births. PWS initially appears as flat red macules in childhood; lesions tend to darken progressively to purple with soft tissue hypertrophy and, by middle age, they often become raised as a result of the development of vascular nodules which are susceptible to spontaneous bleeding or hemorrhage. PWS is a significant clinical problem that results in loss of self-esteem since most malformations occur on the face. The pulsed dye laser (PDL) is the treatment of choice for PWS but the regrowth of pathologic blood vessels post-PDL treatment is a major clinical barrier that needs to be overcome. The pathogenesis of PWS remains incompletely understood. Recent studies have suggested that the sporadic somatic mutation of guanine nucleotide-binding protein, G alpha subunit q (gnaq) (c.548G>A), is linked to PWS. The gnaq (c.548G>A) is primarily present in PWS blood vessels. In addition, PWS have sustained activation of mitogen-activated protein kinases since the infantile stage and, particularly, activation of PKCα and PI3K pathways in hypertrophic and nodular lesions.

Although currently largely elusive, there are at least two major hypotheses regarding the pathogenesis of PWS—nerve denervation and genetic mutations. PWS usually show a deficiency in nerve innervation, which has been speculated to be the cause of these abnormal hypervascular skin lesions. However, confirmatory evidence for this hypothesis has yet to be obtained. Recent studies have suggested that sporadic somatic mutations of GNAQ (c.548G>A) and phosphatidylinositol 3-kinase are linked to the vascular malformations observed in PWS. GNAQ (c.548G>A) has been found to be primarily present in abnormal PWS blood vessels (60%), and/or in connective tissue (30%) and hair follicle/glands (20%). These data suggest that pluripotent cells with GNAQ (c.548G>A) may give rise to multilineages in PWS. In analyzing the pathology of infantile PWS, it has been shown that the entire physiological milieu of human skin is altered during the early course of PWS, including the vasculature and connective tissue. The present data therefore suggest that PWS is a multifactorial disease involving not only the vasculature, but also other structures within the dermis.

PWS are usually characterized by a dilatation of postcapillary venules based on morphological observations. The data presented herein demonstrated that there were no normal—phenotypically and morphologically—arterioles and venules in PWS skin. PWS blood vessels have $CD133^+/CD166^+/EphB1^+/EfnB2^+$ phenotypes, likely due to differentiation impairments in endothelial progenitor cells (EPCs). Therefore, the data suggests that the current patho-anatomical descriptions of PWS should be redefined as 'progressive dilatation of venule-like vasculatures. During development, both dermal arterioles and venules are differentiated from primitive capillary plexus (PCP). It has been suggested that turning off EphB1 and switching on EfnB2 is important for dermal PCP differentiation into arterioles. In default mode, PCP is thought to develop into a vein with consistent expression of EphB1.

It has been postulated that the coexistence of EphB1 and EfnB2 in PWS EPCs will inhibit normal differentiation of both arterioles and venules from PCP, resulting in a venule-like vasculature that is a predetermined fate of PCP. In addition, as Efns and Ephs play a fundamental role in cell-cell interactions, such as the establishment of the arterial-venous vasculature, it has been surmised that the coexistence of Eph-B1 and EfnB2 in ECs will disrupt normal cell-cell interactions and communications, which likely contributes to the progressive dilatation of PWS vasculatures. Indeed, the data shown herein indicates that forced co-expression of EphB1 and EfnB2 in normal ECs leads to formation of PWS-like vasculatures in vitro, for example large-diameter and thick-wall capillaries.

In general, Efn interacts with Eph on adjacent cells, inducing Eph receptor forward and Efn ligand reverse signaling elevation of Eph forward signaling promotes cell segregation; an increase in Efn reverse signaling facilitates neoangiogenesis and invasion. In addition, autoregulation of Eph and Efn signaling occurs when both are expressed in some cell types. A 'cis-binding' theory has been proposed by several reports; namely, that co-expression of Eph and Efn will attenuate Eph forward signaling via lateral cis-binding properties not involving the ligand binding domain of Eph. In the studies presented herein, it has been shown that EphB1 and EfnB2 are associated, which results in a PWS-like vasculature phenotype, which probably acts through the cis-binding mechanism.

In addition to developmental tissue morphogenesis, there is increasing evidence that Eph-Efn signaling regulates cell differentiation, as well as controls stem cell positioning and proliferation. For example, EfnB2 reverse signaling can inhibit osteoclast differentiation, whereas EphB4 forward signaling promotes osteoblast differentiation. The roles of Eph-Efn signaling in the modulation of progenitor cell proliferation and differentiation are largely diverse, presumably depending on downstream effectors, such as activation or inhibition of the mitogen-activated protein kinase pathway. In the studies presented herein, it has been shown that PWS ECs are differentiation impaired EPCs with phenotypes of $CD133^+/CD166^+/EphB1^+/EfnB2^+$, suggesting the potential roles of co-expression of EphB1/EfnB2 in regulation of differentiation status of PWS EPCs. The characterization of the differentiation status of PWS EPCs is of clinical significance, as it proves a therapeutic target of EphB1/EfB2 signaling to modulate the differentiation process of PWS EPCs.

Based upon the studies presented herein, it has been found that PWS blood vessels are immature capillary vasculatures with aberrant stemness properties and dual venous and arterial identities. As such, PWS is a disease resulting from differentiation-impaired EPCs in human skin that develop into venule-like vasculatures morphologically and undergo progressive dilatation due to the disruption of normal EC-EC interactions by the co-existence of EphB1/EfnB2.

In other studies presented herein, 107 proteins were identified from formalin-fixed paraffin-embedded (FFPE) tissues as being differentially expressed (DE) in PWS lesions as compared to normal skins, the DE proteins are mainly involved in the functional processes of metabolism/biosynthesis, membrane trafficking, cytoskeleton and cell adhesion/migration. The results are consistent with the TEM study showing that PWS ECs, pericytes, and fibroblasts are very hyperactive in biosynthesis, metabolism and vesicular secretion. It was further confirmed that the expressions of cell adhesion/migration/exocytosis related proteins, including VAT1, IQGAP1, HSC70, clathrin, perlecan, spectrin $1\alpha$ and GDIR1, were significantly upregulated in PWS blood vessels in both hypertrophic lesions and nodules. The aberrant expression patterns of these proteins underlie a molecular mechanism for the enhanced secretion of extracellular vesicles (EVs) from PWS blood vessels. Furthermore, the levels of Col6A1 and Col6A3 proteins were found to be decreased in PWS lesions, which provide initial steps in elucidating the mechanism accounting for the collagenous alterations that were previously reported from infantile up through hypertrophic lesions and nodules.

Biosynthesis and exocytosis of EVs is a biological process that consists of vesicle-mediated membrane secretory trafficking and fusion of intracellular vesicles with the plasma membrane. The EVs contain cell type-specific compositions of cellular contents such as lipids, proteins, mRNAs and microRNAs. EVs can be taken up by a variety of neighboring cells and by systemic circulation into distant cells; thus, EVs can facilitate intercellular communications by exchanging biological contents between cells. Exocytosis of EVs requires dynamic rearrangements of the intracellular cytoskeleton architecture. Many proteins can function as key regulators for cytoskeleton remodeling, such as IQGAP1, clathrin, spectrin $1\alpha$, HSC70, calmodulin (CaM) and GDIR1, to modulate EV exocytosis. These proteins either interact with the cytoskeleton as it scaffolds to recruit their partner proteins or act as modulators to regulate cytoskeleton reorganization. For example, IQGAP1 has been shown to play multiple roles at different steps in the secretory pathway by: (1) linking to actin via S100 in a $Ca^{2+}$-dependent manner, which can be regulated by CaM; (2) regulating actin dynamics to facilitate vesicle docking and fusion with the plasma membrane; (3) interacting with CDC42 and regulating the exocytosis in gastric parietal cells and epithelial cells; (4) forming a complex with Rab27A and regulating exocytosis of insulin-containing vesicles in pancreatic $\beta$ cells; and (5) associating with exocyst complex molecules, such as Exo70, Sec3 and Sec8, which mediate the tethering of exocytotic vesicles, HSC70 forms a complex with other co-chaperones and enhances the chaperone's ATPase activity, thus regulating vesicle exocytosis and endocytosis. Clathrin is one of the major proteins involved in the formation of coated vesicles. VAT1, spectrin $1\alpha$ and clathrin have been found in synaptic protein complexes. In studies presented herein, it has been shown that all of these exocytotic proteins are dysregulated in PWS lesions (see FIG. 6 and Table 4), suggesting an aberrant alteration in EV formation and exocytosis in PWS lesions. Indeed, the TEM studies have confirmed that PWS ECs release more EVs than normal ECs. These findings together suggest that upregulation of exocytotic proteins results in enhanced EV release from PWS ECs. These EVs contain specific cell tropism from the parental lesional ECs where they are released and orchestrate the essential pathological signaling into neighboring ECs and pericytes, causing disease progression. It can be speculated that these EVs may be released into the circulation where they can be isolated and their EC-specific compositions characterized to identify the unique pathological phenotypes of PWS blood vessels.

Upregulation of IQGAP1, perlecan and spectrin may modulate cell adhesion/mobility signaling, thus contributing to the progressive dilatation of PWS blood vessels, the most prominent clinical phenotype of the disease. IQGAP1 can crosslink actin filaments via its calponin homology domain or interact with a subset of microtubule associated proteins to facilitate cell mobility. Spectrin can interact with annx family members, such as annx 6, to modulate proteolysis for adhesion complexes, including focal adhesion kinase (FAK). In addition, perlecan regulates angiogenesis and facilitates migration of ECs. In studies presented herein, it was found that the expressions of IQGAP1, perlecan, and spectrin were upregulated in PWS ECs. The data suggest that enhanced expression of these molecules likely contributes to the steady and dynamic expansion of PWS ECs over time. In particular, the upregulation of IQGAP1 was also found in pericytes and fibroblasts in PWS lesions, suggesting its potential roles in mediating the progressive expansion of the entire PWS blood vessel into matrix of the dermis as well as outgrowth of the soft tissues seen in hypertrophic lesions and nodules.

In a particular embodiment, the disclosure provides for pathogenic associated biomarkers and/or serum EVs' biomarkers that can be used to identify vascular anomalies or malformations in a subject. Examples of vascular anomalies or malformations, include but are not limited to, arteriovenous malformations (AVM), venous malformations (VM), port-wine stain (PWS), Sturge-Weber syndrome (SWS), Klippel-Trenaunay-Weber syndrome (KTWS), hemangioma (including, capillary hemangioma, cavernous hemangioma, compound hemangiomas, lobular hemangioma, and infantile hemangioma), cavernoma, capillary telangiectasia, dural AV fistula, and angiokeratoma. Examples of the pathogenic associated biomarkers and/or serum EVs' biomarkers for identifying vascular anomalies or malformations in a subject, include but are not limited to, Ephs, Efns, ADAMs, MMPs, STYs, CD31, CD133, CD166, VAT1, IQGAP1, HSC70, clathrin, perlecan, spectrin α1, GDIR1, collagen subtypes 6A1 and 6A3, and the additional biomarkers listed in Table 4. More specifically, the pathogenic associated biomarkers and/or serum EVs' biomarkers disclosed herein can be used:

(1) to identify whether a subject has vascular anomalies or malformations;
(2) to monitor the progression or regression of vascular anomalies or malformations in a subject;
(3) to monitor the effectiveness of treatments for vascular anomalies or malformations in a subject;
(4) to aid in prognosis of the treatment options for vascular anomalies or malformations in a subject;
(5) to aid in specific targeting of endothelial cells, pericytes or fibroblasts of vascular anomalies or malformations in a subject; and
(6) to regulate their biological functions for treatment of vascular anomalies or malformations in a subject.

In one embodiment, the disclosure provides a method comprising: performing an analysis of one or more samples from a subject to determine an expression profile of 1, 2, 3, 4, 5, 6, 7, 8, 9, 10, 11, 12, 13, 14, 15, 20, 30, 40, 50, 60, 70, 80, 90, or 100 different pathogenic associated biomarkers and/or serum EV biomarkers disclosed herein, or any range that includes or is between any two of the foregoing numbers. In a further embodiment, the one or more samples from the subject are tissue biopsy skin samples and/or serum samples. Expression and/or molecular profiling comprises the profiling of at least one gene (or gene product) for each assay technique that is performed. Different numbers of genes or gene products can be assayed with different techniques. Any biomarker disclosed herein that is associated directly or indirectly with a target therapeutic can be assessed based on either the gene, e.g., DNA sequence, and/or gene product, e.g., mRNA or protein. Such nucleic acid and/or polypeptide can be profiled as applicable as to presence or absence, level or amount, mutation, sequence, haplotype, rearrangement, copy number, etc. In some embodiments, a single gene and/or one or more corresponding gene products is assayed by more than one profiling technique. A gene or gene product (also referred to herein as "marker" or "biomarker"), e.g., an mRNA or protein, is assessed using applicable techniques (e.g., to assess DNA, RNA, protein), including without limitation FISH, microarray, IHC, sequencing, immunoassay (e.g., immunoblot, immunohistochemistry. ELISA), mass sequencing (e.g., RNA-Seq), SWATH-MS, transmission electron microscope, and quantitative PCR. Therefore, any of the markers disclosed herein can be assayed by a single molecular profiling technique or by multiple methods disclosed herein (e.g., a single marker is profiled by one or more of SWATH-MS. IHC, immunoassay, mass sequencing, microarray, quantitative PCR, etc.). The number of markers assayed can depend on the technique used. For example, microarray and massively parallel sequencing lead themselves to high throughput analysis. In a particular embodiment, the pathogenic associated biomarkers and/or serum EV markers comprise one or more of the following biomarkers Ephs, Efns, ADAMs, MMPs, STYs, CD31, CD133, CD166, VAT1, IQGAP1, HSC70, clathrin, perlecan, spectrin α1, GDIR1, collagen subtypes 6A1 and 6A3, and the additional biomarkers listed in Table 4. In another or further embodiment, the pathogenic associated biomarkers and/or serum EV markers being profiled comprise 1, 5, 10, 15, 20, 25, 30, 35, 40, 45, 50, 60, 70, 80, 90, 100 or more additional serum markers listed in Table 4, or any range that includes or is between any two of the foregoing numbers.

The Tables provided herein set forth information that one of skill in the art can readily use to identify the human gene sequences and polypeptide sequences associated with the particular gene. The particular sequences (known in the art) are incorporated herein by reference in their entirety. An exemplary listing of these biomarkers to be measured is provided in Table 4.

The systems and methods disclosed herein can be used to select a treatment whose projected efficacy can be linked to molecular profiling results using the pathogenic associated biomarkers and/or serum EV biomarkers of the disclosure. The disclosure comprises use of molecular profiling results to suggest associations with treatment responses. In an embodiment, the appropriate biomarkers for molecular profiling are selected on the basis of the visual presentation of the vascular anomaly or malformation in a subject. These suggested biomarkers can be used to modify a default list of pathogenic associated biomarkers and/or serum EV biomarkers. In some embodiments, rules are used to provide the suggested treatments based on the molecular profiling test results. The "best evidence" can be used as the basis for a rule. The simplest rules are constructed in the format of "if biomarker(s) positive then treatment option one, else treatment option two." Treatment options can include treatment with one or more specific drug products, treatment with pulsed dye laser, surgery, radiation, freezing, or a combination of any of the foregoing. In some embodiments, more complex rules are constructed that involve the interaction of two or more biomarkers. In such cases, the more complex interactions are typically supported by clinical studies that analyze the interaction between the biomarkers included in the rule. In some embodiments, these biomarkers can be used as therapeutic candidates for specific targeting of vascular anomalies' cells. In such cases, nanoparticles or EVs or other types of particles can be conjugated by a ligand or antibody or other molecules that can recognize these biomarkers for specific targeting. The substances including but not limited to small molecule inhibitors, chromophores, compounds, biological products, etc. can be encapsulated into particles for the purposes of but not limited to therapeutics or image, etc. In some embodiments, these biomarkers can be used as treatments for vascular anomalies. In such cases, modifications of the functions of these biomarkers such as down- or up-regulation of their expressions or promote/inhibit their biological activities will result in restoration of normal blood vessels formation from vascular malformations, therefore ultimately to treat vascular anomalies. Finally, a report can be generated that describes the association of the response and the biomarker and a summary statement of the best evidence supporting the treatments selected. Ultimately, the treating physician will decide on the best course of treatment.

Molecular profiling using the pathogenic associated biomarkers and/or serum EV biomarkers of the disclosure can be performed by any known means for detecting a molecule in a biological sample. Profiling can be performed on any applicable biological sample. The sample typically comes from an individual with a suspected or having a vascular anomaly or malformation. Molecular profiling of the sample can also be performed by any number of techniques that assess the amount or state of a biological factor, such as a DNA sequence, an mRNA sequence or a protein. Such techniques include without limitation immunohistochemistry (IHC), in situ hybridization (ISH), fluorescent in situ hybridization (FISH), various types of microarray (mRNA expression arrays, protein arrays, etc.), various types of sequencing (Sanger, pyrosequencing, etc.), comparative genomic hybridization (CGH), NextGen sequencing, Northern blot, Southern blot, immunoassay, quantitative PCR, SWATH-MS and any other appropriate technique to assay the presence or quantity of a biological molecule of interest. Any one or more of these methods can be used concurrently or subsequent to each other.

Molecular profiling using the pathogenic associated biomarkers and/or serum EV biomarkers of the disclosure can be used to select a candidate treatment for a subject. For example, the candidate treatment can be a treatment with a pulsed dye laser, surgery, radiation, freezing, one or more active drug products, and/or a treatment to modify their biological functions. Differential expression can include either over expression and under expression of a biological product, e.g., a gene, mRNA or protein, compared to a control. The control can include similar cells to the sample, but without vascular anomalies or malformations. The control can be derived from the same patient, e.g., a normal adjacent portion of the same organ as the vascular anomalies or malformations, or the control can be derived from healthy tissues from a healthy subject or population of subjects.

The source of differential expression in a sample (e.g., between vascular anomalies or malformations and a normal control) can vary. For example, a gene copy number may be increased in a cell, thereby resulting in increased expression of the gene. Alternately, transcription of the gene may be modified, e.g., by chromatin remodeling, differential methylation, differential expression or activity of transcription factors, etc. Translation may also be modified, e.g., by differential expression of factors that degrade mRNA, translate mRNA, or silence translation, e.g., microRNAs or siRNAs. In some embodiments, differential expression comprises differential activity. For example, a protein may carry a mutation that increases the activity of the protein, such as constitutive activation, thereby contributing to a diseased state. Molecular profiling that reveals changes in activity can be used to guide treatment selection and even be selected as treatment targets.

Nucleic acids, as referred to herein, include deoxyribonucleotides or ribonucleotides and polymers thereof in either single- or double-stranded form, or complements thereof. In some embodiments, nucleic acids can contain known nucleotide analogs or modified backbone residues or linkages, which are synthetic, naturally occurring, and non-naturally occurring, which have similar binding properties as a reference nucleic acid (e.g., a naturally occurring nucleic acid), and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). A Nucleic acid sequence (or polynucleotide) includes conservatively modified variants of a reference nucleic acid sequence (e.g., degenerate codon substitutions) or complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid can be used interchangeably with gene, cDNA, mRNA, oligonucleotide, and polynucleotide.

A particular nucleic acid sequence may implicitly encompass the particular sequence and "splice variants" and nucleic acid sequences encoding truncated forms. Similarly, a particular protein encoded by a nucleic acid can encompass any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created/engineered.

The terms "genetic variant" and "nucleic acid variant" are used herein interchangeably to refer to changes or alterations to the reference human gene or the corresponding cDNA sequence at a particular locus, including, but not limited to, nucleotide base deletions, insertions, inversions, and substitutions in the coding and non-coding regions. Deletions may be of a single nucleotide base, a portion or a region of the nucleotide sequence of the gene, or of the entire gene sequence. Insertions may be of one or more nucleotide bases. The genetic variant or nucleotide variant may occur in transcriptional regulatory regions, untranslated regions of mRNA, exons, introns, exon/intron junctions, etc. The genetic variant or nucleotide variant can potentially result in stop codons, frame shifts, deletions of amino acids, altered gene transcript splice forms or altered amino acid sequence.

An allele or gene allele generally comprises a naturally occurring gene having a reference sequence or a gene containing a specific nucleic acid variant.

A gene can include RNAi products. For example, as used herein, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

A haplotype refers to a combination of genetic (nucleotide) variants in a region of an mRNA or a genomic DNA on a chromosome found in an individual. Thus, a haplotype includes a number of genetically linked polymorphic variants which are typically inherited together as a unit.

The term "genotype" as used herein means the nucleotide characters at a particular genetic locus in either one allele or both alleles of a gene (or a particular chromosome region).

With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, i.e., the nucleotide(s) at a particular gene locus. Genotyping can also be done by determining the amino acid variant at a particular position of a protein which can be used to deduce the corresponding nucleotide variant(s).

The term "locus" refers to a specific position or site in a gene sequence or protein. Thus, there may be one or more contiguous nucleotides in a particular gene locus, or one or more amino acids at a particular locus in a polypeptide. Moreover, a locus may refer to a particular position in a gene where one or more nucleotides have been deleted, inserted, or inverted.

As used herein, the terms "polypeptide," "protein," and "peptide" are used interchangeably to refer to an amino acid chain in which the amino acid residues are linked by covalent peptide bonds. The amino acid chain can be of any length of at least two amino acids, including full-length proteins. Unless otherwise specified, polypeptide, protein, and peptide also encompass various modified forms thereof including but not limited to glycosylated forms, phosphorylated forms, etc. A polypeptide, protein or peptide can also be referred to as a gene product.

Lists of gene and gene products that can be assayed by molecular profiling techniques are disclosed herein. Lists of genes may be presented in the context of molecular profiling techniques that detect a gene product (e.g., an mRNA or protein). One of skill will understand that this implies detection of the gene product of the listed genes. Similarly, lists of gene products may be presented in the context of molecular profiling techniques that detect a gene sequence or copy number. One of skill will understand that this implies detection of the gene corresponding to the gene products, including as an example DNA encoding the gene products. As will be appreciated by those skilled in the art, a "biomarker" or "marker" comprises a gene and/or gene product depending on the context. A biomarker can also be a cDNA derived from mRNA through, for example, RT-PCR.

In any of the methods and examples described herein a biomarker (e.g., a cDNA, mRNA, DNA, polypeptide, protein etc.) may be detectably labeled. The biomarker levels and/or presence can then be determined by measuring the amount of presence of a label in an assay.

The terms "label" and "detectable label" can refer to any composition or agent that is detectable by spectroscopic, photochemical, biochemical, immunochemical, electrical, optical, chemical or similar methods. Such labels include biotin for staining with labeled streptavidin conjugate, magnetic beads (e.g., DYNABEADS) fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Labels can include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden Introduction to Immunocytochemistry, 2nd ed., Springer Verlag, NY (1997); and in Haugland Handbook of Fluorescent Probes and Research Chemicals, a combined handbook and catalogue Published by Molecular Probes, Inc. (1996).

Detectable labels include, but are not limited to, nucleotides (labeled or unlabelled), compomers, sugars, peptides, proteins, antibodies, chemical compounds, conducting polymers, binding moieties such as biotin, mass tags, calorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like.

The terms "primer", "probe," and "oligonucleotide" are used herein interchangeably to refer to a relatively short nucleic acid fragment or sequence. They can comprise DNA. RNA, or a hybrid thereof, or chemically modified analog or derivatives thereof. Typically, they are single-stranded. However, they can also be double-stranded having two complementing strands which can be separated by denaturation. Normally, primers, probes and oligonucleotides have a length of from about 8 nucleotides to about 200 nucleotides, preferably from about 12 nucleotides to about 100 nucleotides, and more preferably about 18 to about 50 nucleotides. They can be labeled with detectable markers or modified using conventional manners for various molecular biological applications. Such oligonucleotides can be used in solution or fixed to a substrate (e.g., a nucleic acid array).

The term "isolated" when used in reference to nucleic acids (e.g., genomic DNAs, cDNAs, mRNAs, or fragments thereof) is intended to mean that a nucleic acid molecule is present in a form that is substantially separated from other naturally occurring nucleic acids that are normally associated with the molecule. Because a naturally existing chromosome (or a viral equivalent thereof) includes a long nucleic acid sequence, an isolated nucleic acid can be a nucleic acid molecule having only a portion of the nucleic acid sequence in the chromosome but not one or more other portions present on the same chromosome or nucleic acid that occurs naturally. An isolated nucleic acid can be substantially separated from other naturally occurring nucleic acids that are on a different chromosome of the same organism. An isolated nucleic acid can also be a composition in which the specified nucleic acid molecule is significantly enriched so as to constitute at least 10%, 20%, 30%, 40%, 50%, 60%, 70%, 80%, 90%, 95%, or at least 99% of the total nucleic acids in the composition.

An isolated nucleic acid can be a hybrid nucleic acid having the specified nucleic acid molecule covalently linked to one or more nucleic acid molecules that are not the nucleic acids naturally flanking the specified nucleic acid. For example, an isolated nucleic acid can be in a vector. In addition, the specified nucleic acid may have a nucleotide sequence that is identical to a naturally occurring nucleic acid or a modified form or mutein thereof having one or more mutations such as nucleotide substitution, deletion/insertion, inversion, and the like.

An isolated nucleic acid can be prepared from a recombinant host cell (in which the nucleic acids have been recombinantly amplified and/or expressed) or can be a chemically synthesized nucleic acid having a naturally occurring nucleotide sequence or an artificially modified form thereof.

The term "isolated polypeptide" as used herein is defined as a polypeptide molecule that is present in a form other than that found in nature. Thus, an isolated polypeptide can be a non-naturally occurring polypeptide. For example, an isolated polypeptide can be a "hybrid polypeptide." An isolated polypeptide can also be a polypeptide derived from a naturally occurring polypeptide by additions or deletions or substitutions of amino acids. An isolated polypeptide can also be a "purified polypeptide" which is used herein to mean a composition or preparation in which the specified polypeptide molecule is significantly enriched so as to constitute at least 10% of the total protein content in the composition. A "purified polypeptide" can be obtained from natural or recombinant host cells by standard purification techniques, or by chemically synthesis, as will be apparent to skilled artisans.

The term "high stringency hybridization conditions," when used in connection with nucleic acid hybridization, includes hybridization conducted overnight at 42° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 0.1×SSC at about 65° C. The term "moderate stringent hybridization conditions," when used in connection with nucleic acid hybridization, includes hybridization conducted overnight at 37° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

For the purpose of comparing two different nucleic acid or polypeptide sequences, one sequence (test sequence) may be described to be a specific percentage identical to another sequence (comparison sequence). The percentage identity can be determined by the algorithm of Karlin and Altschul, Proc. Natl. Acad. Sci. USA, 90:5873-5877 (1993), which is incorporated into various BLAST programs. The percentage identity can be determined by the "BLAST 2 Sequences" tool, which is available at the National Center for Biotechnology Information (NCBI) website. See Tatusova and Madden. FEMS Microbiol. Lett., 174(2):247-250 (1999). For pairwise DNA-DNA comparison, the BLASTN program is used with default parameters (e.g., Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP program can be employed using default parameters (e.g., Matrix: BLOSUM62; gap open: 11; gap extension: 1; x_dropoff 15; expect: 10.0; and wordsize: 3, with filter). Percent identity of two sequences is calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST is used to compare two sequences, it aligns the sequences and yields the percent identity over defined, aligned regions. If the two sequences are aligned across their entire length, the percent identity yielded by the BLAST is the percent identity of the two sequences. If BLAST does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence. Various versions of the BLAST programs can be used to compare sequences, e.g., BLAST 2.1.2 or BLAST+ 2.2.22.

A subject can be any animal which may benefit from the methods of the disclosure, including, e.g., humans and non-human mammals, such as primates, rodents, horses, dogs and cats. Subjects include without limitation a eukaryotic organism, most preferably a mammal such as a primate. e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may be referred to as an individual or a patient.

Treatment of a condition or individual according to the disclosure is an approach for obtaining beneficial or desired medical results, including clinical results, but not necessarily a cure. For purposes of this disclosure, beneficial or desired clinical results include, but are not limited to, alleviation or amelioration of one or more symptoms, diminishment of extent of a disease, disorder, condition or syndrome, stabilized (i.e., not worsening) state of a disease, disorder, condition or syndrome, preventing spread (e.g., growth of the vascular anomalies or malformations) of a disease, disorder, condition or syndrome, delay or slowing of disease, disorder, condition or syndrome progression, amelioration or palliation of the disease, disorder, condition or syndrome state, and remission (whether partial or total), whether detectable or undetectable. Treatment also includes improving the appearance of the subject's skin and/or the wellbeing of the subject as compared to not receiving treatment or if receiving a different treatment. A treatment can include administration of one of more therapeutic agents which provides a normalizing effect on vascular anomalies or malformations (i.e., restoration of vascular tissue to a normal state). Therapeutic agents selected by the methods of the disclosure are not limited. Any therapeutic agent can be selected where a link can be made between molecular profiling and potential efficacy of the agent. Therapeutic agents for use in the methods of the disclosure comprise agents that inhibit or block pathological pathways that are mediated by the EV serum markers disclosed herein. e.g., agents that block the expression of Ephs, Efns, ADAMs, MMPs, STYs, CD31, CD133, CD166, VAT1, IQGAP1, HSC70, clathrin, perlecan, spectrin α1, and/or GDIR1, and/or agents that increase the expression of collagen subtypes 6A1 and 6A3. Examples of such therapeutic agents, include small molecule drug products (e.g., KYL, dasatinib, foretinib, PD-173955, bosutinib, TAPI-0, TAPI-1, TAPI-2, GI 254023X, TMI-1, etc.), gene silencing agents (e.g., antisense oligonucleotides, ribozymes, RNA interference, microRNAs, CRISPR), TALENs, and surface targeting ligands (e.g., antibodies, nanoparticles, etc.). For example, surface targeting ligands like antibodies or fragments thereof, can be used to target surface biomarkers, like CD133, CD166, Ephs, Efns on the surface of endothelial cells, or bind EV trafficked proteins like VAT1, IQGAP1, HSC70, clathrin, perlecan, spectrin α1, and GDIR1.

In one embodiment, the disclosure provides for use of EV as a delivery vector for the therapeutic agents disclosed herein. EVs (including exosomes) are small intracellular membrane-based vesicles with different compositions that are involved in several biological and pathological processes. The exploitation of EV as drug delivery vehicles offers important advantages compared to other nanoparticulate drug delivery systems such as liposomes and polymeric nanoparticles; EVs are non-immunogenic in nature due to similar composition as body's own cells. In general, the formation of EVs consists of three different stages: (1) the formation of endocytic vesicles from plasma membrane, (2) the inward budding of the endosomal vesicle membrane resulting in MVBs that consist of intraluminal vesicles (ILVs), and (3) the fusion of these MVBs with the plasma membrane, which releases the vesicular contents, known as EVs. The EVs can be loaded with a drug product by using saponin permeabilization, freeze-thaw cycling, sonification, and extrusion procedures. In alternate embodiments, the disclosure provides for use of liposomes or nanoparticles as a delivery vectors or gold nanoparticles for the therapeutic agents disclosed herein. A liposome is a synthetic vesicle with a phospholipid membrane that self-assembles into various sizes and shapes in an aqueous environment. Polymeric nanoparticles are drug delivery systems that help in the entrapment, encapsulation, or attachment of drug molecules. Both of these delivery systems have been used to deliver different types of drug molecules, including anti-cancer drugs, anti-fungal drugs, and analgesics. In another alternate embodiment, the disclosure provides for use of viruses or retroviruses as a delivery vectors for the therapeutic agents disclosed herein. In particular, viruses and retroviruses are ideally suited for administering gene silencing agents, including siRNAs and miRNAs that inhibit the expression of one or more pathogenic associated biomarkers and/or serum EV biomarkers disclosed herein.

A sample as used herein includes any relevant sample that can be used for molecular profiling, e.g., sections of tissues such as biopsy or tissue removed during surgical or other procedures, frozen sections taken for histological purposes, blood samples, cerebral spinal fluid and the like. Such samples include blood and blood fractions or products (e.g., serum, buffy coat, plasma, platelets, red blood cells, and the like), cultured cells (e.g., primary cultures, explants, and transformed cells). A sample may be processed according to techniques understood by those in the art. A sample can be, without limitation, fresh, frozen or fixed. In some embodiments, a sample comprises formalin-fixed paraffin-embedded (FFPE) tissue or fresh frozen (FF) tissue. A sample can comprise cultured cells, including primary or stem cell lines derived from a subject sample. A sample can also refer to an extract from a sample from a subject. For example, a sample can comprise DNA. RNA or protein extracted from a tissue. Many techniques and commercial kits are available for such purposes. The fresh sample from the individual can be treated with an agent to preserve RNA prior to further processing, e.g., cell lysis and extraction. Samples can include frozen samples collected for other purposes. Samples can be associated with relevant information such as age, gender, and clinical symptoms present in the subject; source of the sample; and methods of collection and storage of the sample. A sample is typically obtained from a subject.

A biopsy comprises (i) the process of removing a tissue sample for diagnostic or prognostic evaluation, and (ii) to the tissue specimen itself. Any biopsy technique known in the art can be applied to the molecular profiling methods of the disclosure. The biopsy technique applied can depend on the tissue type to be evaluated, the size and type of the vascular anomaly or malformation, among other factors. Representative biopsy techniques include, but are not limited to, excisional biopsy, incisional biopsy, needle biopsy, surgical biopsy, and bone marrow biopsy. An "excisional biopsy" refers to the removal of an entire vascular anomaly or malformation with a small margin of normal tissue surrounding it. An "incisional biopsy" refers to the removal of a wedge of tissue that includes a cross-sectional diameter of the vascular anomaly or malformation. Molecular profiling can use a "core-needle biopsy" of the vascular anomaly or malformation mass, or a "fine-needle aspiration biopsy" which generally obtains a suspension of cells from within the vascular anomaly or malformation. Biopsy techniques are discussed, for example, in Harrison's Principles of Internal Medicine, Kasper, et al., eds., 16th ed., 2005, Chapter 70, and throughout Part V.

In some aspects of the disclosure, the biomarkers are assessed by gene expression profiling. Methods of gene expression profiling include methods based on hybridization analysis of polynucleotides, and methods based on sequencing of polynucleotides. Commonly used methods known in the art for the quantification of mRNA expression in a sample include northern blotting and in situ hybridization (Parker & Barnes (1999) Methods in Molecular Biology 106:247-283); RNAse protection assays (Hod (1992) Biotechniques 13:852-854); and reverse transcription polymerase chain reaction (RT-PCR) (Weis et al. (1992) Trends in Genetics 8:263-264). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Nucleic acid variants can be detected by a suitable detection process. Non limiting examples of methods of detection, quantification, sequencing and the like are; mass detection of mass modified amplicons (e.g., matrix-assisted laser desorption ionization (MALDI) mass spectrometry and electrospray (ES) mass spectrometry), a primer extension method (e.g., iPLEX; Sequenom, Inc.), microsequencing methods (e.g., a modification of primer extension methodology), ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183,958), direct DNA sequencing, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH). Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension (e.g., microarray sequence determination methods), Tag arrays, Coded microspheres, Template-directed incorporation (TDI), fluorescence polarization, Colorimetric oligonucleotide ligation assay (OLA), Sequence-coded OLA, SWATH-MS, Microarray ligation, Ligase chain reaction, Padlock probes, Invader assay, hybridization methods (e.g., hybridization using at least one probe, hybridization using at least one fluorescently labeled probe, and the like), conventional dot blot analyses, single strand conformational polymorphism analysis (SSCP, e.g., U.S. Pat. Nos. 5,891,625 and 6,013,499; Orita et al., Proc. Natl. Acad. Sci. U.S.A. 86: 27776-2770 (1989)), denaturing gradient gel electrophoresis (DGGE), heteroduplex analysis, mismatch cleavage detection, and techniques described in Sheffield et al., Proc. Natl. Acad. Sci. USA 49: 699-706 (1991), White et al., Genomics 12: 301-306 (1992), Grompe et al., Proc. Natl. Acad. Sci. USA 86: 5855-5892 (1989), and Grompe, Nature Genetics 5: 111-117 (1993), cloning and sequencing, electrophoresis, the use of hybridization probes and quantitative real time polymerase chain reaction (QRT-PCR), digital PCR, nanopore sequencing, chips and combinations thereof. The detection and quantification of alleles or paralogs can be carried out using the "closed-tube" methods described in U.S. patent application Ser. No. 11/950,395, filed on Dec. 4, 2007. In some embodiments the amount of a nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

RT-PCR can be used to determine RNA levels, e.g., mRNA or miRNA levels, of the biomarkers of the disclosure. RT-PCR can be used to compare such RNA levels of the biomarkers of the disclosure in different sample populations, in normal and in vascular anomalies or malformations, with or without drug treatment, to characterize patterns of gene expression, to discriminate between closely related RNAs, and to analyze RNA structure. General PCR techniques are known and have been modified to include quantitative PCR, real-time PCR and the like.

A first step in any RT-PCR is obtaining RNA, e.g., mRNA, from a sample. The starting material can be total RNA isolated from a vascular anomaly or malformation, and from corresponding normal tissues, respectively. Thus, RNA can be isolated from a sample, e.g., skin biopsy, and compared with pooled DNA from healthy donors. If the source of mRNA is a skin biopsy, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al. (1997) Current Protocols of Molecular Biology, John Wiley and Sons. Methods for RNA extraction from paraffin embedded tissues are disclosed, for example, in Rupp & Locker (1987) Lab Invest. 56:A67, and De Andres et al., BioTechniques 18:42044 (1995). In particular, RNA isolation can be performed using purification kit, buffer set and protease from commercial manufacturers, such as Qiagen, according to the manufacturer's instructions (QIAGEN Inc., Valencia, Calif.). For example, total RNA from cells in culture can be isolated using Qiagen RNeasy mini-columns. Numerous RNA isolation kits are commercially available and can be used in the methods of the disclosure.

In the alternative, the first step is the isolation of miRNA from a target sample. The starting material is typically total RNA isolated from a vascular anomaly or malformation, and corresponding normal tissues, respectively. If the source of miRNA is a skin biopsy, miRNA can be extracted, for example, from frozen or archived paraffin-embedded and fixed (e.g. formalin-fixed) tissue samples.

General methods for miRNA extraction are well known in the art and are disclosed in standard textbooks of molecular biology, including Ausubel et al (1997) Current Protocols of Molecular Biology, John Wiley and Sons. Methods for RNA extraction from paraffin embedded tissues are disclosed, for example, in Rupp & Locker (1987) Lab Invest. 56:A67, and De Andres et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Numerous RNA isolation kits are commercially available and can be used in the methods of the disclosure.

Whether the RNA comprises mRNA, miRNA or other types of RNA, gene expression profiling by RT-PCR can include reverse transcription of the RNA template into cDNA, followed by amplification in a PCR reaction. Commonly used reverse transcriptases include, but are not limited to, avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan™ RT-PCR can be performed using commercially available equipment, such as, for example, ABI PRISM 7700. Sequence Detection System (Perkin-Elmer-Applied Biosystems. Foster City. Calif., USA), or Lightcycler (Roche Molecular Biochemicals, Mannheim. Germany). In one specific embodiment, the 5' nuclease procedure is run on a real-time quantitative PCR device such as the ABI PRISM 7700™ Sequence Detection System. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells and detected at the CCD. The system includes software for running the instrument and for analyzing the data.

TaqMan data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

Real time quantitative PCR (also quantitative real time polymerase chain reaction, QRT-PCR or Q-PCR) is a more recent variation of the RT-PCR technique. Q-PCR can measure PCR product accumulation through a dual-labeled fluorigenic probe (i.e., TaqMan probe). Real time PCR is compatible both with quantitative competitive PCR, where internal competitor for each target sequence is used for normalization, and with quantitative comparative PCR using a normalization gene contained within the sample, or a housekeeping gene for RT-PCR See, e.g. Held et al. (1996) Genome Research 6:986-994.

IHC is a process of localizing antigens (e.g., proteins) in cells of a tissue by binding antibodies specifically to antigens in the tissues. The antigen-binding antibody can be conjugated or fused to a tag (e.g., a detectable label) that allows its detection, e.g., via visualization. In some embodiments, the tag is an enzyme that can catalyze a color-producing reaction, such as alkaline phosphatase or horseradish peroxidase. The enzyme can be fused to the antibody or non-covalently bound, e.g., using a biotin-avidin system. Alternatively, the antibody can be tagged with a fluorophore, such as fluorescein, rhodamine, DyLight Fluor or Alexa Fluor. The antigen-binding antibody can be directly tagged or it can itself be recognized by a detection antibody that carries the tag. Using IHC, one or more proteins may be detected. The expression of a gene product can be related to its staining intensity compared to control levels. In some embodiments, the gene product is considered differentially expressed if its staining varies at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold in the sample versus the control.

The biomarkers of the disclosure can also be identified, confirmed, and/or measured using the microarray technique. Thus, the expression profile biomarkers can be measured in either fresh or paraffin-embedded tissue sample, using microarray technology. In this method, polynucleotide or oligonucleotide sequences of interest are plated, or arrayed, on a microchip substrate. The arrayed sequences are then hybridized with specific DNA probes from cells or tissues of interest (e.g., cDNA from PCR or other sources). The source of mRNA can be total RNA isolated from a sample, e.g., a vascular anomaly or malformation and corresponding normal tissues. Thus, RNA can be isolated from a variety of a vascular anomalies or malformations. If the source of mRNA is a skin biopsy, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. In one aspect, at least 10, 50, 100, 200, 300, 400, 500, 600, 700, 800, 900, 1,000, 1,500, 2,000, 3000, 4000, 5000, 6000, 7000, 8000, 9000, 10,000, 15,000, 20,000, 25,000, 30,000, 35,000, 40,000, 45,000 or at least 50,000 nucleotide sequences are applied to the substrate. Each sequence can correspond to a different gene, or multiple sequences can be arrayed per gene. The microarrayed genes, immobilized on the microchip, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al. (1996) Proc. Natl. Acad. Sci. USA 93(2):106-149). Microarray analysis can be performed by commercially available equipment following manufacturer's protocols, including without limitation the Affymetrix GeneChip technology (Affymetrix, Santa Clara, Calif.), Agilent (Agilent Technologies, Inc., Santa Clara. Calif.), or Illumina (Illumina, Inc., San Diego, Calif.) microarray technology.

In some embodiments, the Agilent Whole Human Genome Microarray Kit (Agilent Technologies, Inc., Santa Clara, Calif.) can be used. The system can analyze more than 41,000 unique human genes and transcripts represented, all with public domain annotations. The system is used according to the manufacturer's instructions.

In some embodiments, the Illumina Whole Genome DASL assay (Illumina Inc., San Diego, Calif.) is used. The system offers a method to simultaneously profile over 24,000 transcripts from minimal RNA input, from both fresh frozen (FF) and formalin-fixed paraffin embedded (FFPE) tissue sources, in a high throughput fashion.

Microarray expression analysis comprises identifying whether a gene or gene product is up-regulated or down-regulated relative to a reference. The identification can be performed using a statistical test to determine statistical significance of any differential expression observed. In some embodiments, statistical significance is determined using a parametric statistical test. The parametric statistical test can comprise, for example, a fractional factorial design, analysis of variance (ANOVA), a t-test, least squares, a Pearson correlation, simple linear regression, nonlinear regression, multiple linear regression, or multiple nonlinear regression. Alternatively, the parametric statistical test can comprise a one-way analysis of variance, two-way analysis of variance, or repeated measures analysis of variance. In other embodiments, statistical significance is determined using a nonparametric statistical test. Examples include, but are not limited to, a Wilcoxon signed-rank test, a Mann-Whitney test, a Kruskal-Wallis test, a Friedman test, a Spearman ranked order correlation coefficient, a Kendall Tau analysis, and a nonparametric regression test. In some embodiments, statistical significance is determined at a p-value of less than about 0.05, 0.01, 0.005, 0.001, 0.0005, or 0.0001. Although the microarray systems used in the methods of the disclosure may assay thousands of transcripts, data analysis need only be performed on the transcripts of interest, thereby reducing the problem of multiple comparisons inherent in performing multiple statistical tests. The p-values can also be corrected for multiple comparisons, e.g., using a Bonferroni correction, a modification thereof, or other technique known to those in the art, e.g., the Hochberg correction, Holm-Bonferroni correction. Sidak correction, or Dunnett's correction. The degree of differential expression can also be taken into account. For example, a gene can be considered as differentially expressed when the fold-change in expression compared to control level is at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold different in the sample versus the control. The differential expression takes into account both over expression and under expression. A gene or gene product can be considered up or down-regulated if the differential expression meets a statistical threshold, a fold-change threshold, or both. For example, the criteria for identifying differential expression can comprise both a p-value of 0.001 and fold change of at least 1.5-fold (up or down). One of skill will understand that such statistical and threshold measures can be adapted to determine differential expression by any molecular profiling technique disclosed herein.

Various methods of the disclosure make use of many types of microarrays that detect the presence and potentially the amount of biological entities in a sample. Arrays typically contain addressable moieties that can detect the presence of the entity in the sample, e.g., via a binding event. Microarrays include without limitation DNA microarrays, such as cDNA microarrays, oligonucleotide microarrays and SNP microarrays, microRNA arrays, protein microarrays, antibody microarrays, tissue microarrays, cellular microarrays (also called transfection microarrays), chemical compound microarrays, and carbohydrate arrays (glycoarrays). DNA arrays typically comprise addressable nucleotide sequences that can bind to sequences present in a sample. MicroRNA arrays. e.g., the MMChips array, can be used to detect microRNAs. Protein microarrays can be used to identify protein-protein interactions, including without limitation identifying substrates of protein kinases, transcription factor protein-activation, or to identify the targets of biologically active small molecules. Protein arrays may comprise an array of different protein molecules, commonly antibodies, or nucleotide sequences that bind to proteins of interest. Antibody microarrays comprise antibodies spotted onto the protein chip that are used as capture molecules to detect proteins or other biological materials from a sample, e.g., from cell or tissue lysate solutions. For example, antibody arrays can be used to detect biomarkers from bodily fluids, e.g., serum or urine, for diagnostic applications. Tissue microarrays comprise separate tissue cores assembled in array fashion to allow multiplex histological analysis. Cellular microarrays, also called transfection microarrays, comprise various capture agents, such as antibodies, proteins, or lipids, which can interact with cells to facilitate their capture on addressable locations. Chemical compound microarrays comprise arrays of chemical compounds and can be used to detect protein or other biological materials that bind the compounds. Carbohydrate arrays (glycoarrays) comprise arrays of carbohydrates and can detect, e.g., protein that bind sugar moieties. One of skill will appreciate that similar technologies or improvements can be used according to the methods of the disclosure.

Another approach is a multi-parallel sequencing system (MPSS) approach described by Brenner et al. (2000) Nature Biotechnology 18:630-634, that combines non-gel-based signature sequencing with in vitro cloning of millions of templates on separate microbeads. First, a microbead library of DNA templates is constructed by in vitro cloning. This is followed by the assembly of a planar array of the template-containing microbeads in a flow cell at a high density. The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a cDNA library.

MPSS data has many uses. The expression levels of nearly all transcripts can be quantitatively determined; the abundance of signatures is representative of the expression level of the gene in the analyzed tissue. Quantitative methods for the analysis of tag frequencies and detection of differences among libraries have been published and incorporated into public databases for SAGE data and are applicable to MPSS data. The availability of complete genome sequences permits the direct comparison of signatures to genomic sequences and further extends the utility of MPSS data. Because the targets for MPSS analysis are not preselected (like on a microarray), MPSS data can characterize the full complexity of transcriptomes. This is analogous to sequencing millions of ESTs at once, and genomic sequence data can be used so that the source of the MPSS signature can be readily identified by computational means.

Serial analysis of gene expression (SAGE) is a method that allows the simultaneous and quantitative analysis of a large number of gene transcripts, without the need of providing an individual hybridization probe for each transcript. First, a short sequence tag (e.g., about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, e.g. Velculescu et al. (1995) Science 270:484-487; and Velculescu et al. (1997) Cell 88:243-51.

Any method capable of determining a DNA copy number profile of a particular sample can be used for molecular profiling according to the disclosure as along as the resolution is sufficient to identify the biomarkers of the disclosure. The skilled artisan is aware of and capable of using a number of different platforms for assessing whole genome copy number changes at a resolution sufficient to identify the copy number of the one or more biomarkers of the disclosure. Some of the platforms and techniques are described in the embodiments below.

In some embodiments, the copy number profile analysis involves amplification of whole genome DNA by a whole genome amplification method. The whole genome amplification method can use a strand displacing polymerase and random primers.

In some aspects of these embodiments, the copy number profile analysis involves hybridization of whole genome amplified DNA with a high-density array. In a more specific aspect, the high-density array has 5,000 or more different probes. In another specific aspect, the high-density array has 5,000, 10,000, 20,000, 50,000, 100,000, 200,000, 300,000, 400,000, 500,000, 600,000, 700,000, 800,000, 900,000, or 1,000,000 or more different probes. In another specific aspect, each of the different probes on the array is an oligonucleotide having from about 15 to 200 bases in length. In another specific aspect, each of the different probes on the array is an oligonucleotide having from about 15 to 200, 15 to 150, 15 to 100, 15 to 75, 15 to 60, or 20 to 55 bases in length.

Microarrays typically comprise a plurality of oligomers (e.g., DNA or RNA polynucleotides or oligonucleotides, or other polymers), synthesized or deposited on a substrate (e.g., glass support) in an array pattern. The support-bound oligomers are "probes", which function to hybridize or bind with a sample material (e.g., nucleic acids prepared or obtained from the vascular anomaly or malformation), in hybridization experiments. The reverse situation can also be applied: the sample can be bound to the microarray substrate and the oligomer probes are in solution for the hybridization. In use, the array surface is contacted with one or more targets under conditions that promote specific, high-affinity binding of the target to one or more of the probes. In some configurations, the sample nucleic acid is labeled with a detectable label, such as a fluorescent tag, so that the hybridized sample and probes are detectable with scanning equipment. DNA array technology offers the potential of using a multitude (e.g., hundreds of thousands) of different oligonucleotides to analyze DNA copy number profiles. In some embodiments, the substrates used for arrays are surface-derivatized glass or silica, or polymer membrane surfaces (see e.g., in Z. Guo, et al., Nucleic Acids Res, 22, 5456-65 (1994); U. Maskos, E. M. Southern, Nucleic Acids Res, 20, 1679-84 (1992), and E. M. Southern, et al., Nucleic Acids Res, 22, 1368-73 (1994), each incorporated by reference herein). Modification of surfaces of array substrates can be accomplished by many techniques. For example, siliceous or metal oxide surfaces can be derivatized with bifunctional silanes, i.e., silanes having a first functional group enabling covalent binding to the surface (e.g., Si-halogen or Si-alkoxy group, as in —SiCl3 or —Si(OCH3)3, respectively) and a second functional group that can impart the desired chemical and/or physical modifications to the surface to covalently or non-covalently attach ligands and/or the polymers or monomers for the biological probe array. Silylated derivatizations and other surface derivatizations that are known in the art (see for example U.S. Pat. No. 5,624,711 to Sundberg, U.S. Pat. No. 5,266,222 to Willis, and U.S. Pat. No. 5,137,765 to Farnsworth, each incorporated by reference herein). Other processes for preparing arrays are described in U.S. Pat. No. 6,649,348, to Bass et al., assigned to Agilent Corp., which disclose DNA arrays created by in situ synthesis methods.

Polymer array synthesis is also described extensively in the literature including in the following: WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, 5,412,087, 6,147,205, 6,262,216, 6,310,189, 5,889,165, and 5,959,098 in PCT Applications Nos. PCT/US99/00730 (International Publication No. WO 99/36760) and PCT/US01/04285 (International Publication No. WO 01/58593), which are all incorporated herein by reference in their entirety for all purposes.

Nucleic acid arrays that are useful in the disclosure include, but are not limited to, those that are commercially available from Affymetrix (Santa Clara. Calif.) under the brand name GeneChip™. Example arrays are shown on the website at affymetrix.com. Another microarray supplier is Illumina, Inc., of San Diego, Calif. with example arrays shown on their website at illumina.com.

In some embodiments, the methods provide for sample preparation. Depending on the microarray and experiment to be performed, sample nucleic acid can be prepared in a number of ways by methods known to the skilled artisan. In some aspects of the disclosure, prior to or concurrent with genotyping (analysis of copy number profiles), the sample may be amplified any number of mechanisms. The most common amplification procedure used involves PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford), and U.S. Pat. Nos. 4,683,202, 4,683,195, 4,800,159 4,965,188, and 5,333,675, and each of which is incorporated herein by reference in their entireties for all purposes. In some embodiments, the sample may be amplified on the array (e.g., U.S. Pat. No. 6,300,070 which is incorporated herein by reference)

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See. U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

The disclosure can also use molecular profiling to look at the genotype of a sample from a subject vs. an expression profile. Molecular profiling according to the disclosure comprises methods for genotyping one or more biomarkers by determining whether an individual has one or more nucleotide variants (or amino acid variants) in one or more of the genes or gene products. Genotyping one or more genes according to the methods of the disclosure in some embodiments, can provide more evidence for selecting a treatment.

The biomarkers of the disclosure can be analyzed by any method useful for determining alterations in nucleic acids or the proteins they encode. According to one embodiment, the ordinary skilled artisan can analyze the one or more genes for mutations including deletion mutants, insertion mutants, frameshift mutants, nonsense mutants, missense mutant, and splice mutants.

Nucleic acid used for analysis of the one or more genes can be isolated from cells in the sample according to standard methodologies (Sambrook et al., 1989). The nucleic acid, for example, may be genomic DNA or fractionated or whole cell RNA, or miRNA acquired from exosomes or cell surfaces. Where RNA is used, it may be desired to convert the RNA to a complementary DNA (cDNA). In one embodiment, the RNA is whole cell RNA; in another, it is poly-A RNA; in another, it is exosomal RNA. Normally, the nucleic acid is amplified. Depending on the format of the assay for analyzing the one or more genes, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

In situ hybridization assays are well known and are generally described in Angerer et al., Methods Enzymol. 152:649-660 (1987). In an in situ hybridization assay, cells, e.g., from a biopsy, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters. FISH (fluorescence in situ hybridization) uses fluorescent probes that bind to only those parts of a sequence with which they show a high degree of sequence similarity.

FISH is a cytogenetic technique used to detect and localize specific polynucleotide sequences in cells. For example, FISH can be used to detect DNA sequences on chromosomes. FISH can also be used to detect and localize specific RNAs, e.g., mRNAs, within tissue samples. FISH uses fluorescent probes that bind to specific nucleotide sequences to which they show a high degree of sequence similarity. Fluorescence microscopy can be used to find out whether and where the fluorescent probes are bound. In addition to detecting specific nucleotide sequences. e.g., translocations, fusion, breaks, duplications and other chromosomal abnormalities, FISH can help define the spatial-temporal patterns of specific gene copy number and/or gene expression within cells and tissues.

As is apparent from the above survey of the suitable detection techniques, it may or may not be necessary to amplify the target DNA, i.e., the gene, cDNA, mRNA, or a portion thereof to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., Molecular Cloning: A Laboratory Manual, $4^{th}$ Ed., Cold Spring Harbor Laboratory, Cold Spring Harbor, N.Y., 2012.

Protein-based detection techniques are also useful for molecular profiling, especially when the nucleotide variant causes amino acid substitutions or deletions or insertions or frameshift that affect the protein primary, secondary or tertiary structure. To detect the amino acid variations, protein sequencing techniques may be used. For example, a protein or fragment thereof corresponding to a gene can be synthesized by recombinant expression using a DNA fragment isolated from an individual to be tested. Preferably, a cDNA fragment of no more than 100 to 150 base pairs encompassing the polymorphic locus to be determined is used. The amino acid sequence of the peptide can then be determined by conventional protein sequencing methods. Alternatively, the HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., Anal. Chem., 72:757-763 (2000).

Other protein-based detection molecular profiling techniques include immunoaffinity assays based on antibodies selectively immunoreactive with mutant gene encoded protein according to the disclosure. Methods for producing such antibodies are known in the art. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See, e.g., U.S. Pat. Nos. 4,376,110 and 4,486,530, both of which are incorporated herein by reference.

Typically, once the expression profile is determined, physicians or genetic counselors or patients or other researchers may be informed of the result. Specifically, the result can be cast in a transmittable form that can be communicated or transmitted to other researchers or physicians or genetic counselors or patients. Such a form can vary and can be tangible or intangible. The result can be embodied in descriptive statements, diagrams, photographs, charts, images or any other visual forms. For example, images of gel electrophoresis of PCR products can be used in explaining the results. Diagrams showing where a variant occurs in an individual's gene are also useful in indicating the testing results. The statements and visual forms can be recorded on a tangible media such as papers, computer readable media such as floppy disks, compact disks, etc., or on an intangible media, e.g., an electronic media in the form of email or website on internet or intranet. Thus, the information and data on a test result can be produced anywhere in the world and transmitted to a different location. Accordingly, the disclosure also encompasses a method for producing a transmittable form of information on the gene expression profile or molecular profile of pathogenic associated biomarkers and/or serum EV biomarkers from a subject. The method comprises the steps of (1) determining the profile from the samples according to methods of the disclosure; and (2) embodying the result of the determining step in a transmittable form. The transmittable form is the product of the production method. In a further embodiment, the produced results can then be used to determine a treatment regimen.

The practice of the disclosure may also employ conventional biology methods, software and systems. Computer software products of the disclosure typically include computer readable medium having computer-executable instructions for performing the logic steps of the method of the disclosure. Suitable computer readable medium includes floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier. Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The disclosure further provides the use of the methods and biomarkers disclosed herein for the development of therapies that can be used to treat vascular anomalies or malformations. In particular embodiment, the disclosure provides a method for testing the effectiveness of a therapy for treating vascular anomalies or malformations comprising: obtaining samples (e.g., a skin tissue biopsy sample(s) and/or EV serum sample(s)) from a subject having vascular anomalies or malformations at a first time point; measuring a first expression profile of a set of 5, 6, 7, 8, 9 10, 11, 12, 13, 14, 15, 20, 25, 30, 35, 40, 50, 55, 60, 65, 70, 75, 80, 90, 100, 120, 140, 150, 160, 180, 250 or more pathogenic associated biomarkers and/or serum extracellular vesicles (EV) biomarkers described herein (e.g., biomarkers listed in Table 4 and throughout the disclosure) from the subject's sample(s) obtained at the first time point; treating the subject with one or more treatments for vascular anomalies or malformations, such treatments, can include light and laser therapies, and/or administration of agent(s) that interfere with or downregulate EphB1/EfnB2 signaling pathways, and/or administration of agent(s) that inhibit or suppress exosome release or exocytosis from lesional vasculatures or vascular anomalies or malformations; obtaining a sample(s) (e.g., a skin tissue biopsy sample(s) and/or EV serum sample(s)) from the subject at a second time point, wherein the sample(s) are from the same general area as the sample(s) obtained at the first time point; measuring a second expression profile of a set of 5, 6, 7, 8, 9 10, 11, 12, 13, 14, 15, 20, 25, 30, 35, 40, 50, 55, 60, 65, 70, 75, 80, 90, 100, 120, 140, 150, 160, 180, 250 or more pathogenic associated biomarkers and/or serum extracellular vesicles (EV) biomarkers described herein (e.g., biomarkers listed in Table 4 and throughout the disclosure) from the subject's sample(s) obtained at the second time point; comparing the first expression profile of the set of pathogenic associated biomarkers and/or serum EV biomarkers with the second expression profile of the set pathogenic associated biomarkers and/or serum EV biomarkers, wherein the same set of pathogenic associated biomarkers and/or serum EV biomarkers are compared between the first expression profile and the second expression profile; and indicating that the treatment for vascular anomalies or malformations in the subject was effective based upon measuring an improvement in the expression levels of the set of pathogenic associated biomarkers and/or serum EV biomarkers in the subject's samples, wherein an improvement is indicated by the second expression profile of the biomarkers being more similar to an expression profile of a normal control subject vs. the first expression profile, and wherein a lack of improvement is indicated by measuring no difference between the first expression profile of the biomarkers and the second expression profile of the biomarkers, or by the second expression profile being more dissimilar to an expression profile of a normal control subject vs. the first expression profile. In a further embodiment, the set of pathogenic associated biomarkers and/or serum extracellular vesicles (EV) biomarkers is selected from Ephs, Efns, ADAMs, MMPs, STYs, CD31, CD133, CD166, CALM, ANXA1, MIME, DERM, PPIA, ANXA5, SUCB2, CO4A, TBB4B, COX2, CO6A3, TBA1B, ENOA, KPYM, ATPB, KV201, ACTBL, CO6A1, PRELP, IGHG1, THIO, TBB5, PGK1, ACTBM, LUM, POTEF, LAC7, TBA4A, APOA1, CBPA3, PGS2, CMA1, DSG1, TRYB2, LDHA, HSP71, TPIS, POSTN, POTEJ, LEG3, HSPB1, RLA2, PRDX6, CACP, ML12B, E9PBV3, K1C9, UBA1, K2C6B, IMB1, CAN1, Septin-7, NPM, FACR2, FBLN2, NDUAD, VAT1, HNRPU, ADT3, RL13A, ACADV, G6PI, PLEC, HNRPC, AL3A2, IF5A1, GDIR1, VTDB, TKT, TCPB, C1QBP, K2C3, CAPZB, GANAB, ANXA6, PTBP1, K2C1B, F16PI, CNDP2, MOES, CYB5, PRDBP, EHD2, PHB, CDC42, RTN3, CISY, SPTBN1, HEP2, ACOC, CD44, CLH1, CALL5, IQGA1, ECHA, MYO1C, HSC70, TRY6, ANXA7, ASPN, U2AF1, FIBB, PGAM2, CAP1, SERPH, RL36, RS12, clatharin, perlecan, spectrin α1. In yet a further embodiment, the set pathogenic associated biomarkers and/or serum extracellular vesicles (EV) biomarkers comprises at least VAT1, IQGAP1, HSC70, CLH1, perlecan, spectrin α1, and GDIR1. Generally accepted therapies for treating vascular anomalies and malformations include, but are not limited to, pulsed laser dye, intense pulsed light, surgery, radiation, and freezing. The disclosure provides for the development of investigational therapies that can be used to treat vascular anomalies or malformations by use of the methods and biomarkers disclosed herein. In particular, the studies presented herein demonstrate that the coexistence of Eph receptor B1 and ephrin B2 in endothelial progenitor cells is indicative of clinicopathological vasculature anomalies and malformations. As such, agents which inhibit EphB1/EfnB2 signaling pathways have promise as therapies for treating vascular anomalies and malformations. Specific examples of inhibitors of EphB1/EfnB2 signaling pathways include agents that are receptor antagonists (e.g., anti-EphB1 antibodies, anti-EphB1-Fc, anti-EfnB2 antibodies, anti-EfnB2-Fc, etc.); small molecule inhibitors (e.g., EphB1-IN-10); siRNA, shRNA and RNAi products to suppress EphB1 and/or EfnB2 gene expression. The methods and biomarkers of the disclosure can be used to test and develop investigational therapies and approaches for treating vascular anomalies or malformations by inhibiting or suppressing EphB1/EfnB2 signaling pathways. Moreover, further studies presented herein indicate that agents which suppress exosome release or exocytosis from lesional vasculatures could be beneficial for treating vascular anomalies and malformations. In particular, agents which suppress the expression of exocytic proteins associated with biomarkers disclosed herein (e.g., exocytic proteins listed in Table 4) can be used, e.g., to suppress exocytosis from lesional vasculatures, and thus be used to treat vascular anomalies and malformations. Examples of exocytic proteins include those exocytic proteins listed in Table 4.

The following examples are intended to illustrate but not limit the disclosure. While they are typical of those that might be used, other procedures known to those skilled in the art may alternatively be used.

EXAMPLES

Tissue Preparation.

A total of 37 PWS biopsy samples, including four infant, 11 pediatric, five teenage and 17 adult specimens, were obtained from 27 subjects and de-identified for this study (Table 1).

TABLE 1

Clinical description of patients with port-wine stains (PWS)

| Patient No. | Sex | Age (years) | Diagnosis | Treatment History |
|---|---|---|---|---|
| 1 | F | 0 | PWS arm | None |
| 2 | F | 0 | PWS chest | None |
| 3 | M | 1 | PWS face | PDL |
| 4 | M | 1 | PWS face | None |
| 5 | M | 2 | PWS back | None |
| 6 | M | 2 | PWS back | None |
| 7 | M | 2 | PWS face and back | None |
| 8 | M | 3 | PWS face | None |
| 9 | F | 3 | PWS face and back | None |
| 10 | M | 3 | PWS face | None |
| 11 | M | 3 | PWS face | None |
| 12 | F | 3 | PWS face | None |
| 13 | F | 4 | PWS face | None |
| 14 | F | 5 | PWS face | None |
| 15 | M | 6 | PWS arm | None |
| 16 | F | 16 | PWS face | PDL |
| 17 | F | 13 | PWS face | None |
| 18 | M | 27 | PWS face | None |
| 19 | M | 38 | PWS face | PDL |
| 20 | M | 38 | PWS arm | PDL |
| 21 | M | 41 | PWS face | PDL |
| 22 | M | 51 | PWS face | None |
| 23 | M | 55 | PWS face | None |
| 24 | F | 56 | PWS face | PDL |
| 25 | F | 40 | PWS face | None |
| 26 | M | 55 | PWS face | PDL |
| 27 | M | 36 | PWS face | PDL |

F, female;
M, male;
PDL, pulsed-dye laser

A total of 14 infant, 40 pediatric, 43 teenage and 45 adult control skin specimens for adjacent normal skin or patients without PWS were retrieved from skin biopsy tissue banks and served as controls. Biopsy tissue was fixed in 10% buffered formalin (Fisher Scientific, Pittsburgh, PA, U.S.A.) and processed for permanent paraffin embedding on an ASP 300 tissue processor (Leica Microsystems, Bannockburn, IL, U.S.A.). Approximately 6-μm-thick paraffin sections were cut and collected.

For blood vessel counting, six of 600 μm×300 μm or two of 1200 μm×600 μm areas underneath the epidermis in each biopsy section were randomly picked. The numbers and perimeters of blood vessels in each chosen area were counted and measured. A total of 464 normal blood vessels (n=11 control subjects) and 982 lesional blood vessels (n=15 patients with PWS) were analyzed. The total numbers of rete ridges and papillae containing capillary loops from each section were counted and the full length of epidermis of each section was directly measured using Nikon NIS-Elements software (Nikon, Tokyo, Japan). The densities of rete ridges and papillae containing capillary loops per mm epidermis were calculated.

The arteriole-like and venule-like vasculatures were identified based on their morphological characteristics from semi-thin sections from infants with PWS (n=4). Adjacent normal skin from the same participants were used as controls. A total of 45 PWS and 33 normal blood vessels were identified, counted and categorized. The thickness of blood vessel walls was measured with ImageJ software (National Institutes of Health. Bethesda, MD, U.S.A.). The number of participants in each age group is listed in Table 2.

TABLE 2

Impairment of normal capillary loop formation in patients with port-wine stains (PWS)

| Age group (years) | Density of rete ridges[a] | | Density of papillae with capillary loops[b] | | Ratio[c] | | n | |
|---|---|---|---|---|---|---|---|---|
| | Control | PWS | Control | PWS | Control | PWS | Control | PWS |
| 0-1 | 8.43 ± 1.99 | 6.86 ± 3.77 | 5.81 ± 1.26 | 1.74 ± 1.51* | 0.71 ± 0.09 | 0.22 ± 0.20* | 14 | 4 |
| 2-10 | 9.56 ± 2.26 | 3.71 ± 1.90* | 7.21 ± 1.89 | 0.89 ± 0.75* | 0.77 ± 0.14 | 0.25 ± 0.21* | 40 | 11 |
| 11-29 | 9.90 ± 2.44 | 1.96 ± 2.16* | 7.66 ± 1.87 | 0.27 ± 0.28* | 0.78 ± 0.10 | 0.22 ± 0.22* | 68 | 5 |
| 30-60 | 9.74 ± 1.79 | 2.26 ± 3.17* | 7.22 ± 1.48 | 0.20 ± 0.26* | 0.75 ± 0.15 | 0.18 ± 0.24* | 20 | 17 |

Data are mean ± SD unless otherwise indicated.

[a]Number of rete ridges per mm epidermis;

[b]number of papillae containing capillary loops per mm epidermis;

[c]number of papillae containing capillary loops/number of total rete ridges per mm epidermis.

*$P < 0.05$ vs. control groups.

Semi-Thin and Ultrathin Section Preparation.

Biopsies were immediately fixed in Karnovsky solution (2% paraformaldehyde, 3% glutaraldehyde, 0.1 mol L$^{-1}$ sodium cacodylate) for 3 h, then underwent postfixation with 1% osmium tetraoxide solution for 1 h, en bloc staining with Kelenberger uranyl acetate buffer for 2 h and a series of dehydrations (30%, 50%, 70%, 90%, 100% ethanol, two-thirds ethanol and one-third propylene oxide, one-third ethanol and two-thirds propylene oxide, and 100% propylene oxide). Tissues then were infiltrated with an Epon mixture overnight and embedded in Epon in a 60° C. oven for 3 days. For light microscopy experiments, the semi-thin sections with thicknesses of 500-600 nm were cut and stained with Richardson solution. For transmission electron microscopy experiments, 70-nm-thick sections were cut and stained with uranyl and lead citrates.

Immunohistochemistry.

Paraffin sections were deparaffinized according to routine procedures. Antigen retrieval was performed in 10 mmol L$^{-1}$ sodium citrate buffer (pH 6.0) at 97° C. for 2-4 h. The sections were then incubated in a humidified chamber overnight at 4° C. with the following primary antibodies: CD31 (1:50 dilution; Bethyl Laboratories, Montgomery, TX, U.S.A.); CD133 (1:50 dilution; Boster Immunoleader, Pleasanton, CA, U.S.A.); von Willebrand factor [vWF; 1:50 dilution (Dako, Carpinteria, CA, U.S.A.)]; EphB4 (1:50 dilution; Thermo Fisher. Waltham, MA U.S.A.); CD166, Efn-B2 and EphB1 (all 1:50 dilution; all from Santa Cruz Biotechnology, Santa Cruz, CA U.S.A.). Biotinylated antimouse, antirabbit and antigoat secondary antibodies were incubated with sections for 2 h at room temperature after the primary antibody reactions. An indirect biotin avidin diaminobenzidine (DAB) system (Dako, Glostrup, Denmark) was used for detection.

The cellular immunoreactivity score was evaluated using a system reported by Populo et al. (*Br. J. Ophthalmol* 95:715-9 (2011)). Briefly, the intensity was graded as follows: no staining, 0; weak staining, 1; intermediate staining, 2; strong staining, 3. The percentage of immunoreactive cells was graded as either focal (1 indicates ≤30%) or diffuse (2 indicates >30%). For each antibody, an immunoreactivity score was estimated by multiplying the intensity grade by the grade of the immunoreactive cell percentage. Immunoreactivity scores were classified as follows:

negative=0, low=1, moderate=2, 3 and 4, high=6.

Human Dermal Microvascular Endothelial Cell Culture.

Human dermal microvascular endothelial cells (hDMVECs) were purchased from Cell Applications (San Diego, CA, U.S.A.) and were cultured in EC Basal Medium with growth supplement (Cell Applications). As hDMVECs were a heterogeneous population of venular and arteriolar ECs, biotinylated chimera EfnB2-Fc and streptavidin-conjugated magnetic beads were used to isolate the EphB1$^+$/EfnB2$^-$ hDMVEC subpopulation.

Chimera EfnB2-Fc (20 µg; R&D Systems, Minneapolis, MN, U.S.A.) was added into a N-hydroxysuccinimide type of biotinylation reagent (Thermo Fisher) at a biotin:protein molar ratio of 20:1. The reaction was incubated on ice for 2 h. The protein concentration of biotinylated chimera EfnB2 Fc was then determined after desalting or dialysis. For isolation of the EphB1$^+$/EfnB2$^-$ hDMVEC subpopulation, biotinylated chimera EfnB2-Fc (2 µg) was first incubated with 100 µg streptavidin-conjugated Sera-Mag magnetic beads (GE Healthcare, Pittsburgh, PA, U.S.A.) at room temperature for 15 min; the EfnB2-Fc-magnetic bead complex was then pulled down by magnetic strands to remove free biotinylated chimera EfnB2-Fc. The prepared chimera EfnB2-Fc-magnetic beads were then incubated with 5×10$^5$ hDMVECs on ice for 30 min. The hDMVEC chimera EfnB2-Fc-magnetic bead complexes were then washed in phosphate-buffered saline three times and cultured in complete EC medium. The selected subpopulation was designated EphB1$^+$/EfnB2$^-$ hDMVEC. A total of four independent preparations of a selection of EphB1/EfnB2$^-$ hDMVECs were performed.

Transfection, Immunoprecipitation and Immunoblot.

Human EfnB2 cDNA was amplified using two primers so as to have a Flag and His tag flanked at the N-terminal and C-terminal of EfnB2, respectively. The amplified fragment was cleaved by BamHI and XhoI and cloned into the same sites in a pcDNA3 vector. Insertion was confirmed by Sanger sequencing.

The plasmids containing enhanced green fluorescent protein (EGFP) and human EfnB2 cDNA were transfected into four independently prepared EphB1$^+$/EfnB2$^-$ hDMVEC subpopulations by using a FuGene HD (Thermo Fisher). The cells were then screened with G418 (300-600 µg mL$^{-1}$) for 1 week-10 days to remove untransfected cells in order to obtain EGFP$^+$/EphB1$^+$/EfnB2$^+$ and EphB1$^+$/EfnB2$^+$ cell models (n=4 for each cell model). For the immunoprecipitation assay, the cells were lysed in RIPA buffer [25 mmol L$^{-1}$ Tris (pH 7-8), 150 mmol L$^{-1}$ NaCl, 0.1% sodium dodecyl sulfate, 0.5% sodium deoxycholate and 1% Triton X-100] with proteinase inhibitors. The cell lysate (50 µg total protein) was precleared by protein G agarose beads and goat IgG (Santa Cruz Biotechnology). Goat anti-EphB1 antibody (0.2 µg; Santa Cruz Biotechnology) was incubated with cell lysate for 2 h at room temperature and followed by addition of 20 µL protein G agarose beads. The immunoprecipitated components were identified by Western blot using anti-EphB1, EfnB2 and His antibodies.

Matrigel In Vitro Tube Formation.

The capillary-like structure (CLS) formation of angiogenesis from ECs can be modelled in vitro by a Matrigel-based tube formation assay (Thermo Fisher). ECs plated on Matrigel at low densities form a network of branching structures, which can be photographed and quantified by measuring the length, perimeter or area of the CLS. Matrigel in vitro tube formation was performed in 48-well plates. Briefly, Matrigel (80 µL per well, Thermo Fisher) was added to a 48-well plate and incubated at 37° C. for 30 min. hDMVECs (n=4 for each cell model prepared as described above) were trypsinized and resuspended in EC basal medium without supplements. Each type of cell (2.5-4×10$^4$ in 200 µl) was then added into each well and incubated at 37° C. with 5% CO$^2$ for 12-16 h to form a CLS. The cells were fixed with 4% buffered formalin at the end of the experiments. Images were acquired using a Nikon Eclipse Ti-E system. The CLS wall thickness, perimeter and area of branching point were outlined from the acquired images and directly measured with Nikon NIS-Elements software. The total sample sizes for capillary wall thickness were 47, 46 and 18 CLSs, perimeters were 35, 33 and 12 CLSs, and area of branching points were 155, 79 and 24 CLSs.

SWATH-MS.

Formalin-fixed paraffin-embedded (FFPE) sections were used for SWATH-MS. There was one group of controls (n=3) and two groups of PWS specimens (n=6). The protocols of protein extraction from FFPE sections and peptide library preparation were as reported in Ostasiewicz et al. (*J. Proteome Res.* 9, 3688-700 (2010)). All samples were duplicated during the mass spectrometry studies. Mass spectra were acquired on an AB Sciex 5600+ triple TOF mass spectrometer (AB Sciex, Framingham, MA) in data independent acquisition (DIA) mode. Each SWATH cycle included an MS1 scan and 32 equal SWATH window scans covering the entire MS1 scan range (400-1200 m/z). The DIA files were analyzed using DIA-Umpire according to Deutsch et al. (*Proteomics* 10:1190-5 (2010) and Tsou et al. (Nat. Methods 12:258-64 (2015) with a default setting. The quantification and re-extraction module of DIA-Umpire was used to quantify proteins. iBAQ and MS2 (Top 6 peptides) protein quantities were analyzed using the Perseus software package with a Student's T-Test Immunoblot and Immunohistochemistry (IHC).

The procedures of immunoblot and immunohistochemistry (IHC) and on PWS and control tissues followed the protocols in Gao e al. (*Br. J. Dermatol* 2017; Tan et al. 2014 (J. am. Acad. Dermatol. 71:964-68 (2014); Tan et al. 2016 (*Br. J. Dermatol* (2016); and Yin et al. (*Am. J Dermatopathol* (2016)). The fresh skin biopsy samples were homogenized in radioimmunoprecipitation assay (RIPA) buffer (25 mM Tris, 150 mM NaCl, 0.1%6 SDS, 0.5% sodium deoxycholate, 1% NP-40) containing cocktail proteinase inhibitors. The protein was quantified. For immunoblot, 5-10 µg of total proteins were loaded per lane. The primary antibodies including IQ motif containing GTPase activating protein 1 (IQGAP1), vesicle amine transport 1 (VAT1), spectrin 1α, clathrin, Rho GDP dissociation inhibitor (GDI) alpha (GDIR1), heat shock cognate protein 70 (HSC70), perlecan, annexin A1 (ANXA1), collagen 6A1 (CO6A1), CO6A3, vitamin D binding protein (VDBP) and glyceraldehyde 3-phosphate dehydrogenase (GAPDH) were from Santa Cruz Biotechnology. The dilution for all primary antibodies was 1:3000 and GAPDH was used as the loading control. For IHC, approximately 6 µm thick paraffin sections were cut and antigen retrieval was performed in 10 mM sodium citrate buffer (pH 6.0) at 97° C. for 3 h. Sections were then incubated in a humidified chamber overnight at 4° C. with the following primary antibodies: anti-IQGAP1 (1:50), anti-spectrin 1α (1:50), anticlathrin (1:50), anti-GDIR1 (1:100) and anti-HSC70 (1:200). Biotinylated antimouse secondary antibodies were incubated with the sections for 2 h at room temperature after the primary antibodies' reaction. An indirect biotin avidin diaminobenzidine (DAB) system (Dako, Glostrup, Denmark) was used for detection.

Transmission Electron Microscopy (TEM).

Tissue samples were minced to <0.5 mm$^3$, fixed in Karnovsky's solution (1% glutaraldehyde and 4% paraformaldehyde in 0.1M phosphate buffer) for 24 hours, and followed by post-fixation in 1% osmium tetroxide. After fixation, all of the samples were dehydrated in series graded ethanol solutions and embedded in an Epon-epoxy mixture. Ultra-thin 70 nm thick sections were prepared by using Leica Ultracut 7 for TEM according to standard procedures. The sections were then examined by an electron microscope (Tecnai Spirit, FEI) operated at 80 kV. An AMT camera system was used for electron microscopy and image capture. The quantity and diameter of EVs were analyzed using ImageJ software.

Statistics.

Paired-samples t-tests were performed to evaluate the statistical differences in CLS morphological parameters among the various cell models, and differences between PWS and normal control datasets; and protein expression levels, EV numbers and sizes between PWS lesions and normal controls. Data are presented as mean±SD and a Pvalue<0.05 was considered significant.

Determining the Primary Pathological Phenotypes During the Early Development of PWS.

It was hypothesized that PWS endothelial cells (ECs) are differentiation-impaired endothelial progenitor cells (EPCs), consisting of a dermal primitive capillary plexus (PCP), which eventually develop into venule-like vasculatures morphologically; and that co-expression of venous and arterial-specific markers, for example Eph receptor B1 (EphB1) and ephrin B2 (EfnB2), in PWS EPCs disrupts normal EC-EC interactions, leading to the progressive dilatation of PWS vasculatures observed over time.

The clinical history of PWS biopsy samples is listed in Table 1. Both ectatic thin- and thick-walled blood vessels were observed in adult PWS lesions (see FIG. 1A-C). The density of dermal blood vessels per mm$^2$ was significantly higher in PWS lesions compared with normal control skins [PWS 53.14±21.16 (n=982 blood vessels from 15 participants); control 42.22±5.14 (n=464 blood vessels from 11 participants); P=0.046]. Adult PWS blood vessels displayed statistically significant dilatation: 50% of PWS blood vessels had a circumference ranging from 50 to 200 µm with an additional 19% ranging from 401 to 2500 µm, whereas only 34% of blood vessels in normal skin had circumferences >50 µm (n=982 blood vessels from 15 participants with PWS and 464 blood vessels from 11 controls; P<0.05, Mann-Whitney U-test; see FIG. 1D). However, only ectatic thick-walled, but not thin-walled, blood vessels were observed in infant PWS lesions. Infant PWS blood vessels showed a significantly thicker blood vessel wall compared with adjacent normal skin dermal blood vessels from the same subjects (n=45 PWS and 33 normal blood vessels from four subjects; P<0.05) (see FIG. 1E-G). These results suggested that ectatic thick-walled rather than thin-walled blood vessels were the primary pathological phenotypes during the early development of PWS.

Characterization of the Arterial/Venous Pathoanatomical Features of PWS Blood Vessels.

Differentiation of veins and arteries from dermal PCP is initiated by the end of the second trimester during normal human embryogenesis. In a normal skin papillary plexus, an arterial capillary wall shows homogeneous-appearing basement membrane material, which is distinguished from venous capillary walls by the presence of multilayered basement membrane and bridged fenestrations. In infant PWS, blood vessels showed dilatations and exhibited a typical venule-like vasculature. It was found a substantial reduction in the number of arteriole-like structures in PWS (see FIG. 2A, B). The ratio of arteriole-like to venule-like structures observed from semi-thin sections in infant PWS significantly decreased compared with adjacent normal skin from the same subject [PWS 9.17±9.50%; control 61.27±4.89% (n=45 PWS and 33 normal blood vessels from four subjects); P<0.01] (See FIG. 3C). Therefore, the normal development of arterioles was impaired.

Capillary loops begin sprouting from superficial PCP during weeks 4-5 after birth and are complete prior to 9 months of age as perpendicular hairpin-shaped loops projecting into the dermal papillae. Capillary loops in infant and pediatric PWS are not completely developed. In infant and pediatric patients with PWS, the density of papillae containing capillary loops to total papillae per mm of epidermis significantly decreased from 0-1 and 2-10 years of age, respectively (see FIG. 2F-H, Table 2).

In adolescent and adult PWS, this decrease was even more profound than in infant and pediatric PWS lesions, with significantly lower densities than those in normal human skin at 11-60 years of age (see FIG. 2H, Table 2). The ratio of papillae containing capillary loops to total rete ridges per mm epidermis was significantly lower than normal controls (Table 2). The formation of Rete ridges appeared morphologically normal in infantile PWS, but the densities per mm epidermis were significantly reduced during the progression of the disease (see FIG. 2G, Table 2), especially in hypertrophic and nodular PWS (see FIG. 2I).

The morphological abnormalities observed in vasculatures and deficiency of capillary loop formation in infantile and pediatric PWS suggest that ECs are immature and/or malfunctioned and thus unable to form normal vasculatures, which subsequently fail to form normal capillary loops within the dermal papillae after birth.

Determining the Differentiation Status of PWS ECs.

It was found that most infant, pediatric and adult PWS blood vessels except nodules were positive for CD133 and CD166, markers of EPCs (see FIG. 3, Table 2). CD133 and CD166 were weakly positive in normal dermal ECs in infantile skin but negative in adult human skin (see FIG. 3, Table 2). Consequently, PWS ECs in nonnodular lesions were CD133+/CD166+ EPCs. The PWS EPCs also showed expression of EC differential markers, for example CD31 and vWF (see FIG. 3), suggesting that these EPCs are late stage EPCs with some initial differentiation occurring. Therefore, the ectatic PWS vasculatures are composed of aberrant late-stage EPCs. The results suggest that the immaturity of late-stage PWS EPCs accounts for the progressive vascular dilatation observed over time and the reduction in the number of capillary loops formed in the skin.

Determining the Molecular Identities of PWS EPCs Using Specific Venous (EphB1, EphB4) and Arterial (EfnB2) Markers.

Mutually exclusive expression of venous (EphB1, EphB4) and arterial (EfnB2) markers is required during the early stages of normal vascular plexus remodelling. PCP also express EphB1. It was found that most infant, pediatric and adult PWS ECs co-expressed EphB1 and EfnB2 (n=27 patients with PWS; see FIGS. 4A, 4B and 4E; Table 2). Expression of EphB4 in the PWS sections was not observed. A mild immunoreactive signal of EphB1 and EphB4 could be observed in mature veins but not in other types of vasculatures in normal control skin dermis (n=9 participants, see FIGS. 4C and 4D). Normal dermal capillary ECs show a mild EfnB2 immunoreactive signal (see Table 3).

TABLE 3

Immunoreactive scores for each surface marker in blood vessels from controls and patients with port-wine stains (PWS)

| Patient No. | Age/sample | | CD133 | CD166 | EphB1 | EfnB2 |
|---|---|---|---|---|---|---|
| 1 | Infant | S | 2 | 3 | 0 | 2 |
| 2 | Infant | T | 6 | 6 | 6 | 2 |
| 3 | Infant | Ex | 4 | 6 | 6 | 4 |
| 4 | Infant | S | 3 | 6 | 4 | 4 |
| 5 | Pediatric | T | 4 | 6 | 1 | 3 |
| 6 | Pediatric | T | 6 | 6 | 1 | 4 |
| 7 | Pediatric | T | 4 | 6 | 1 | 4 |
| 8 | Pediatric | F | 4 | 4 | 2 | 2 |
| 9 | Pediatric | T | 4 | 6 | 3 | 2 |
| 10 | Pediatric | F | 4 | 6 | 4 | 3 |
| 11 | Pediatric | F | 6 | 6 | 1 | 3 |
| 12 | Pediatric | F | 3 | 4 | 0 | 1 |
| 13 | Pediatric | F | 4 | 6 | 6 | 4 |
| 14 | Pediatric | F | 4 | 4 | 1 | 2 |
| 15 | Pediatric | Ex | 2 | 4 | 4 | 1 |
| 16 | Teenage | F | 2 | 4 | 4 | 4 |
| | | E | 2 | 3 | 4 | 4 |
| 17 | Teenage | F | 6 | 3 | 3 | 2 |
| | | E | 3 | 2 | 2 | 6 |
| 18 | Adult | F | 2 | 2 | 4 | 2 |
| | | E | 0 | 0 | 4 | 1 |
| 19 | Adult | Ex | 2 | 2 | 4 | 3 |
| 20 | Adult | S | 6 | 6 | 0 | 3 |
| 21 | Adult | S | 0 | 1 | 6 | 0 |
| 22 | Adult | F | 6 | 6 | 4 | 6 |
| | | N | 6 | 6 | 1 | 4 |
| 23 | Adult | F | 3 | 3 | 4 | 4 |
| | | E | 2 | 2 | 4 | 4 |
| 24 | Adult | F | 2 | 2 | 4 | 4 |
| | | E | 0 | 0 | 4 | 0 |
| | | D-1 | 0 | 0 | 0 | 2 |
| | | D-2 | 0 | 0 | 4 | 2 |
| 25 | Adult | F | 2 | 1 | 6 | 1 |
| 26 | Adult | F | 2 | 0 | 6 | 1 |
| 27 | Adult | F | 3 | 1 | 4 | 1 |
| | | D | 1 | 0 | 1 | 0 |
| Control 1 | Pediatric | F | 2 | 1 | 1 | 2 |
| Control 2 | Pediatric | F | 2 | 2 | 1 | 3 |
| Control 3 | Pediatric | Ex | 1 | 1 | 1 | 2 |
| Control 4 | Pediatric | F | 2 | 3 | 1 | 3 |
| Control 5 | Adult | Ex | 0 | 0 | 0 | 1 |
| Control 6 | Adult | Ex | 0 | 0 | 0 | 1 |
| Control 7 | Adult | F | 0 | 0 | 0 | 2 |
| Control 8 | Adult | F | 0 | 0 | 0 | 3 |
| Control 9 | Adult | Ex | 0 | 0 | 0 | 2 |

EphB1, Eph receptor B1;
Efn-B2, ephrin B2;
S, scalp;
T, trunk;
Ex, extremity;
F, facial;
N, neck;
E, edge of PWS lesion sites;
D, nodular PWS These data suggest that both arteriole and venous differentiation from PCP are impaired in PWS. PCP is thought to be predetermined to develop into a vein if expression of EphB1 remains, whereas PCP will differentiate into arteries when EphB1 is off and EfnB2 is switched on. Therefore, aberrant PWS PCP with dual expression of EphB1 and EfnB2 may hamper the normal differentiation of both arterioles and venules, eventually resulting in PWS venule-like vasculatures. In order to explore the roles of co-expressed EphB1/EfnB2 in the alteration of vasculatures, a subset of normal hDMVECs with high expression of surface EphB1 via biotinylated chimera EfnB2-Fc and streptavidin-conjugated magnetic beads were isolated. The rationale for this selection was that the EfnB2-Fc chimera ligand binds to the EphB1+/EphB4+-expressing venous hDMVEC subpopulation, whereas the remaining arterial hDMVEC subpopulation (EphB−/EphB4−) expresses EfnB2. Indeed, the expression of EphB1, EphB4 and EfnB2 could be observed in the heterogeneous population of hDMVECs (see FIG. 4K). The EfnB2-Fc selected hDMVEC subpopulation showed a higher level of EphB1 mRNA by a factor of $1.277\pm0.064$ and a much lower level of EfnB2 mRNA by a factor of $0.195\pm0.021$ than nonselected heterogeneous hDMVEC populations (n=4; FIG. 4F). The protein levels of EfnB2 in the EfnB2-Fc selected hDMVEC subpopulation were undetectable by immunoblotting assay (see FIG. 4K).

Thus, the selected subpopulation was designated as EphB1+/EfnB2+ hDMVECs. The remaining hDMVEC subpopulation after EfnB2-Fc selection showed EfnB2 expression but not EphB1 and EphB4, and was designated as EphB1−/EphB4−/EfnB2+ hDMVEC subpopulation (see FIG. 4K). Subsequently, the EphB1+/EfnB2− hDMVECs (n=4) were transfected with a plasmid carrying EGFP and EfnB2-His. The cells were screened with G418 to obtain EphB1+/EGFP+ and EphB1+/EfnB2+ subsets (n=4 for each cell model) (see FIG. 4F). The EGFP-transfected hDMVECs, EGFP+/EphB1+/EfnB2−, showed similar EphB1 and EfnB2 mRNA levels to the EphB1+/EfnB2− hDMVEC subpopulation (n=4, see FIG. 4F), whereas EfnB2-transfected hDMVECs showed an increase in EfnB2 mRNA by a factor of 3.539±0.372 vs. the EphB1+/EfnB2− hDMVEC subpopulation (n=4; see FIG. 4F).

Figure 5:
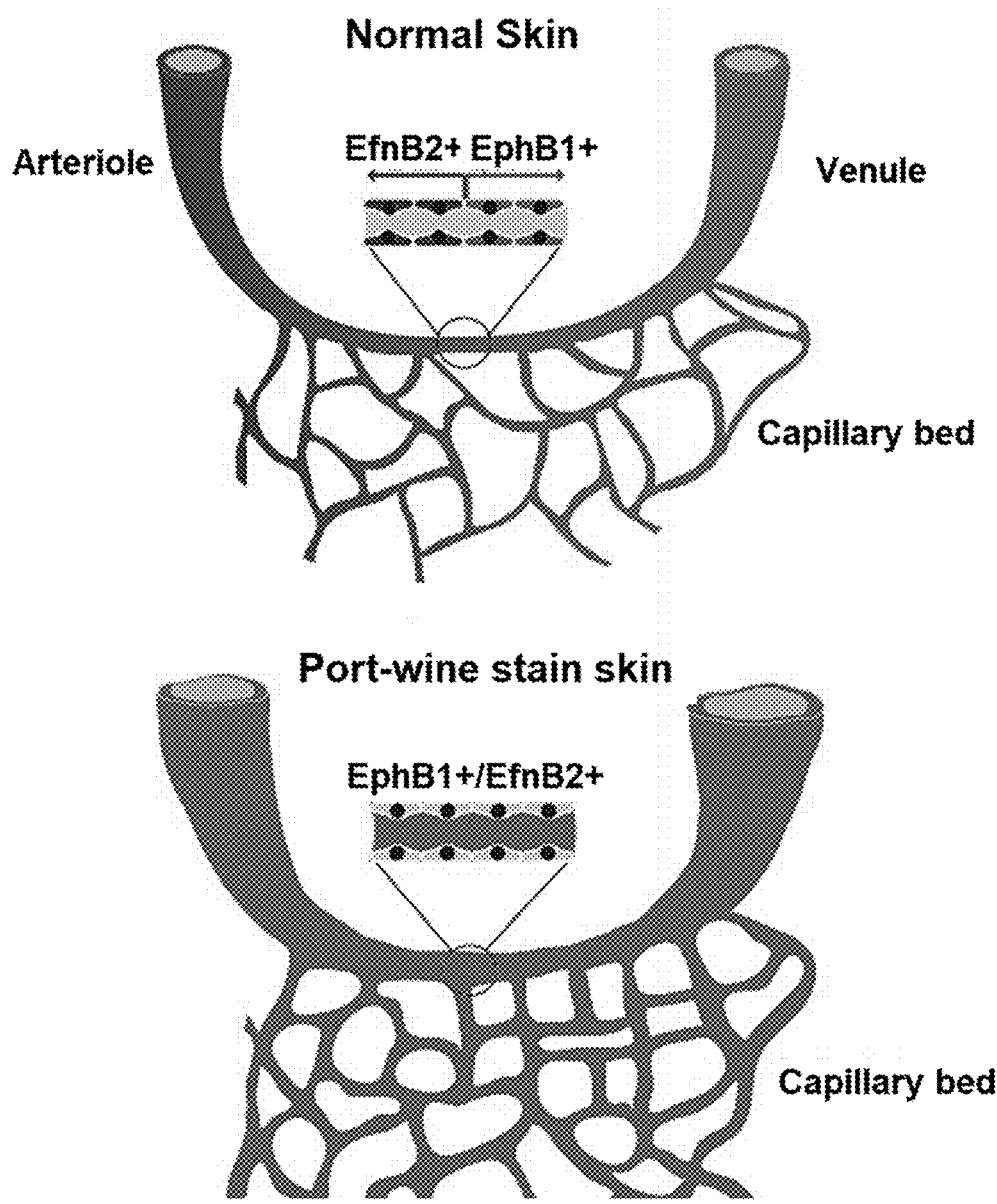
FIG. 5 shows that vasculature in pediatric port-wine stain (PWS) tissue has increased vessel density and significant morphological abnormalities. Endothelial cells in PWS tissue express CD133/CD166 and CD31 markers, as well as co-expressing venous and arterial specific proteins [ephrin B1 (EphB1) and ephrin B2 (EfnB2)], suggesting they are late stage endothelial progenitor cells rather than fully differentiated.

Therefore, these cells were designated as EphB1+/EfnB2+ hDMVECs. CLS formation has been used to assess morphological differentiations involving multiple cellular signaling-activated processes, including cell migration, adhesion, protease secretion and alignment among a variety of ECs. Matrigel tube formation was performed in vitro to characterize the phenotypes of vasculatures formed by various ECs subpopulations prepared as described above. Forced co-expression of EphB1/EfnB2 resulted in formation of PWS blood vessel-like capillary tubes at 12-16 h after cell plating, for example significantly thicker branches (see FIGS. 4G and 4J), larger branch point areas (see FIGS. 4H and 4J) and larger diameters (see FIGS. 4I and 4J), in Matrigel compared with wild-type and EGFP+ hDMVECs (see FIG. 4B-E). The EphB1/EfnB2 cells formed in the CLS remained dynamically unstable and at 16-20 h tended to aggregate as spheres at the branching points. Overexpression of EfnB2 in hDMVECs was confirmed by Western blot using an anti-EfnB2 antibody (see FIG. 4K). An immunoprecipitation assay showed that EphB1 and EfnB2 were associated with each other (see FIG. 4K). Taken together, the co-expression of EphB1 and EfnB2 in ECs results in disruption of the normal vasculature and directly contributes to the formation of abnormal PWS like vasculatures. Accordingly, the above studies indicate that the vasculature in pediatric PWS tissue is aberrant, with increased vessel density and significant morphological abnormalities indicative of immature endothelial development (see FIG. 5)

Screening for Differential Expression of Proteins from PWS Lesions v. Normal Controls Using SWATH-MS.

A total of 299 proteins from PWS FFPE samples were identified by SWATH-MS, among which 107 showed significant changes in their expression levels in PWS lesions as compared to normal skin (see Table 4).

TABLE 4

List of SWATH-MS-identified proteins and DE candidates from FFP PWS samples

| Protein | Protein ID | Changes | T-test p value | Protein full name |
|---|---|---|---|---|
| CALM | P62158 | decrease | 0.0000 | Calmodulin |
| ANXA1 | P04083 | decrease | 0.0378 | Annexin I |
| MIME | P20774 | decrease | 0.0059 | Mimecan |
| DERM | Q07507 | decrease | 0.0034 | Dermatopontin |
| PPIA | P62937 | decrease | 0.0031 | Peptidyl-prolyl cis-trans isomerase A |
| ANXA5 | P08758 | decrease | 0.0100 | Annexin 5 |
| SUCB2 | Q96I99-2 | decrease | 0.0449 | GTP-specific succinyl-CoA synthetase subunit beta, isoform 2 |
| CO4A | P0C0L4 | decrease | 0.0001 | Complement C4-A |
| TBB4B | P68371 | decrease | 0.0002 | Tubulin beta-4B |
| COX2 | P00403 | decrease | 0.0092 | Cytochrome c oxidase, Subunit 2 |
| CO6A3 | P12111-2 | decrease | 0.0194 | Collagen 6 A3 |
| TBA1B | P68363 | decrease | 0.0065 | Tubulin beta-1B |
| ENOA | P06733 | decrease | 0.0018 | apha-enolase |
| KPYM | P14618-3 | decrease | 0.0029 | Pyruvate kinase PKM |
| ATPB | P06576 | decrease | 0.0286 | ATP synthase subunit beta, mitochondrial |
| KV201 | P01614 | decrease | 0.0066 | Immunoglobulin kappa variable 2D-40 |
| ACTBL | Q562R1 | decrease | 0.0044 | Beta-actin-like protein 2 |
| CO6A1 | P12109 | decrease | 0.0338 | Collagen alpha-1 (VI) chain |
| PRELP | P51888 | decrease | 0.0036 | Prolargin |
| IGHG1 | P01857 | decrease | 0.0120 | Immunoglobulin heavy constant gamma 1 |
| THIO | P10599 | decrease | 0.0103 | Thioredoxin |
| TBB5 | P07437 | decrease | 0.0228 | Tubulin beta chain |
| PGK1 | P00558 | decrease | 0.0306 | Phosphoglycerate kinase 1 |
| ACTBM | Q9BYX7 | decrease | 0.1050 | Putative beta-actin-like protein 3 |
| LUM | P51884 | decrease | 0.0003 | Lumican |
| POTEF | A5A3E0 | decrease | 0.0100 | POTE ankyrin domain family member F |
| LAC7 | A0M8Q6 | decrease | 0.0850 | Immunoglobulin lambda, constant 7 |
| TBA4A | P68366 | decrease | 0.0030 | Tubulin alpha-4A chain |
| APOA1 | P02647 | decrease | 0.0151 | Apolipoprotein A-I |
| CBPA3 | P15088 | decrease | 0.0068 | Mast cell carboxypeptidase A |
| PGS2 | P07585 | decrease | 0.0377 | Decorin |
| CMA1 | P23946 | decrease | 0.0971 | Chymase |
| DSG1 | Q02413 | decrease | 0.0321 | Desmoglein-1 |
| TRYB2 | P20231 | decrease | 0.0348 | Tryptase beta-2 |
| LDHA | P00338-3 | decrease | 0.0393 | L-lactate dehydrogenase A chain |
| HSP71 | P08107 | decrease | 0.0274 | Heat shock 70 kDa protein 1 |
| TPIS | P60174-1 | decrease | 0.0164 | Triosephosphate isomerase |
| POSTN | Q15063-3 | decrease | 0.0219 | Periostin |
| POTEJ | P0CG39 | decrease | 0.0135 | POTE ankyrin domain family member J |
| LEG3 | P17931 | decrease | 0.0209 | Galectin-3 |
| HSPB1 | P04792 | decrease | 0.0368 | Heat shock protein beta-1 |

TABLE 4-continued

List of SWATH-MS-identified proteins and DE candidates from FFP PWS samples

| Protein | Protein ID | Changes | T-test p value | Protein full name |
|---|---|---|---|---|
| RLA2 | P05387 | decrease | 0.0379 | 60S acidic ribosomal protein P2 |
| PRDX6 | P30041 | decrease | 0.0448 | Peroxiredoxin-6 |
| CACP | P43155-2 | increase | 0.0144 | Carnitine O-acetyltransferase |
| ML12B | O14950 | increase | 0.0005 | Myosin regulatory light chain 12B |
| E9PBV3 | Q6UWP8 | increase | 0.0005 | Suprabasin |
| K1C9 | P35527 | increase | 0.0139 | Keratin, type I cytoskeletal 9 |
| UBA1 | P22314 | increase | 0.0002 | Ubiquitin-like modifier-activating enzyme 1 |
| K2C6B | P04259 | increase | 0.0082 | Keratin, type II cytoskeletal 6B |
| IMB1 | Q14974 | increase | 0.0107 | Importin subunit beta-1 |
| CAN1 | P07384 | increase | 0.0636 | Calpain-1 catalytic subunit |
| Septin-7 | Q16181-2 | increase | 0.0012 | Septin-7 |
| NPM | P06748-2 | increase | 0.0378 | Nucleophosmin |
| FACR2 | Q96K12 | increase | 0.0192 | Fatty acyl-CoA reductase 2 |
| FBLN2 | P98095-2 | increase | 0.0183 | Fibulin-2 |
| NDUAD | Q9P0J0 | increase | 0.0029 | NADH dehydrogenase 1 alpha subcomplex subunit 13 |
| VAT1 | Q99536 | increase | 0.0212 | Synaptic vesicle membrane protein VAT-1 homolog |
| HNRPU | Q00839-2 | increase | 0.0073 | Heterogeneous nuclear ribonucleoprotein U |
| ADT3 | P12236 | increase | 0.0566 | ADP/ATP translocase 3 |
| RL13A | P40429 | increase | 0.0028 | 60S ribosomal protein L13a |
| ACADV | P49748-2 | increase | 0.0003 | Very long-chain specific acyl-CoA dehydrogenase |
| G6PI | P06744-2 | increase | 0.0878 | Glucose-6-phosphate isomerase |
| PLEC | Q15149-2 | increase | 0.0222 | Plectin-1 |
| HNRPC | P07910-2 | increase | 0.0299 | Heterogeneous nuclear ribonucleoproteins C1/C2 |
| AL3A2 | P51648-2 | increase | 0.0065 | Fatty aldehyde dehydrogenase 2 |
| IF5A1 | P63241-2 | increase | 0.0070 | Eukaryotic translation initiation factor 5A-1 |
| GDIR1 | P52565 | increase | 0.0195 | Rho GDP-dissociation inhibitor 1 |
| VTDB | P02774-2 | increase | 0.0004 | Vitamin D-binding protein |
| TKT | P29401 | increase | 0.0007 | Transketolase |
| TCPB | P78371 | increase | 0.0074 | T-complex protein 1 subunit beta |
| C1QBP | Q07021 | increase | 0.0162 | Complement component 1 Q subcomponent-binding protein |
| K2C3 | P12035 | increase | 0.0241 | Keratin, type II cytoskeletal 3 |
| CAPZB | P47756-2 | increase | 0.0027 | F-actin-capping protein subunit beta |
| GANAB | Q14697-2 | increase | 0.0320 | Neutral alpha-glucosidase AB |
| ANXA6 | P08133 | increase | 0.0224 | Annexin A 6 |
| PTBP1 | P26599-2 | increase | 0.0509 | Polypyrimidine tract-binding protein 1 |
| K2C1B | Q7Z794 | increase | 0.0650 | Keratin, type II cytoskeletal 1b |
| F16P1 | P09467 | increase | 0.0071 | Fructose-1,6-bisphosphatase 1 |
| CNDP2 | Q96KP4 | increase | 0.0134 | Cytosolic non-specific dipeptidase |
| MOES | P26038 | increase | 0.0054 | Moesin |
| CYB5 | P00167 | increase | 0.0154 | Cytochrome b5 |
| PRDBP | Q969G5 | increase | 0.0392 | Caveolae-associated protein 3 |
| EHD2 | Q9NZN4 | increase | 0.0011 | EH domain-containing protein 2 |
| PHB | P35232 | increase | 0.0160 | Prohibitin |
| CDC42 | P60953 | increase | 0.0017 | Cell division control protein 42 homolog |
| RTN3 | O95197-2 | increase | 0.0042 | Reticulon-3 |
| CISY | O75390 | increase | 0.0158 | Citrate synthase, mitochondrial |
| SPTBN1 | Q01082 | increase | 0.0459 | Spectrin, non-erythrocytic 1 |
| HEP2 | P05546 | increase | 0.0056 | Heparin cofactor 2 |
| ACOC | P21399 | increase | 0.0041 | Cytoplasmic aconitate hydratase |
| CD44 | P16070-10 | increase | 0.0366 | CD44 antigen |
| CLH1 | Q00610-2 | increase | 0.0069 | Clathrin heavy chain 1 |
| CALL5 | Q9NZT1 | increase | 0.0554 | Calmodulin-like protein 5 |
| IQGA1 | P46940 | increase | 0.0030 | Ras GTPase-activating-like protein IQGAP1 |
| ECHA | P40939 | increase | 0.0009 | Trifunctional enzyme subunit alpha |
| MYO1C | O00159-2 | increase | 0.0434 | Unconventional myosin-Ic |
| HSC70 | P11142 | increase | 0.0035 | Heat shock cognate 71 kDa protein |
| TRY6 | Q8NHM4 | increase | 0.0404 | Putative trypsin-6 |
| ANXA7 | P20073-2 | increase | 0.0290 | Annexin A7 |

TABLE 4-continued

List of SWATH-MS-identified proteins and DE candidates from FFP PWS samples

| Protein | Protein ID | Changes | T-test p value | Protein full name |
|---|---|---|---|---|
| ASPN | Q9BXN1 | increase | 0.0299 | Asporin |
| U2AF1 | Q01081-2 | increase | 0.0153 | Splicing factor U2AF 35 kDa subunit |
| FIBB | P02675 | increase | 0.0416 | Fibrinogen beta chain |
| PGAM2 | P15259 | increase | 0.0171 | Phosphoglycerate mutase 2 |
| CAP1 | Q01518-2 | increase | 0.0141 | Adenylyl cyclase-associated protein 1 |
| SERPH | P50454 | increase | 0.0377 | Serpin H1 |
| RL36 | Q9Y3U8 | increase | 0.0203 | 60S ribosomal protein L36 |
| RS12 | P25398 | increase | 0.0030 | 40S ribosomal protein S12 |
| K2C1 | P04264 | | 0.1139 | Keratin, type II cytoskeletal 1 |
| ACTG | P63261 | | 0.1772 | Actin, cytoplasmic 2 |
| ATPA | P25705 | | 0.1091 | ATP synthase subunit alpha, mitochondrial |
| SODM | P04179 | | 0.2067 | Superoxide dismutase [Mn], mitochondrial |
| K1C10 | P13645 | | 0.2558 | Keratin, type I cytoskeletal 10 |
| K22E | P35908 | | 0.1209 | Keratin, type II cytoskeletal 2 epidermal |
| BLMH | Q13867 | | 0.2180 | Bleomycin hydrolase |
| DHE3 | P00367 | | 0.1715 | Glutamate dehydrogenase 1, mitochondrial |
| NDK8 | O60361 | | 0.1076 | Putative nucleoside diphosphate kinase |
| EPIPL | P58107 | | 0.0836 | Epiplakin |
| CO1A2 | P08123 | | 0.3556 | Collagen alpha-2(I) chain (Alpha-2 type I collagen) |
| MYH11 | P35749-2 | | 0.0528 | Myosin-11 |
| TTHY | P02766 | | 0.3882 | Transthyretin |
| K2C6C | P48668 | | 0.7864 | Keratin, type II cytoskeletal 6C |
| ACOT1 | Q86TX2 | | 0.1130 | Acyl-coenzyme A thioesterase 1 |
| H2B1J | P06899 | | 0.2799 | Histone H2B type 1-J |
| HS90B | P08238 | | 0.2158 | Heat shock protein HSP 90-beta |
| CO1A1 | P02452 | | 0.3156 | Collagen alpha-1(I) chain |
| CALX | P27824 | | 0.1385 | Calnexin |
| APMAP | Q9HDC9-2 | | 0.2214 | Adipocyte plasma membrane-associated protein |
| MDHC | P40925-2 | | 0.8702 | Malate dehydrogenase, cytoplasmic |
| RTN4 | Q9NQC3-2 | | 0.6569 | Reticulon-4 |
| ACLY | P53396-2 | | 0.2295 | ATP-citrate synthase |
| K2C79 | Q5XKE5 | | 0.1895 | Keratin, type II cytoskeletal 79 |
| OLFL1 | Q6UWY5 | | 0.2413 | Olfactomedin-like protein 1 |
| DESM | P17661 | | 0.6252 | Desmin |
| PDIA1 | P07237 | | 0.0617 | Protein disulfide-isomerase |
| CALL3 | P27482 | | 0.8993 | Calmodulin-like protein 3 |
| IGKC | P01834 | | 0.2819 | Immunoglobulin kappa constant |
| RS3 | P23396 | | 0.5846 | 40S ribosomal protein S3 |
| GRP75 | P38646 | | 0.4332 | Stress-70 protein, mitochondrial |
| SPTN1 | Q13813-2 | | 0.1086 | Spectrin alpha chain, non-erythrocytic 1 |
| HS90A | P07900-2 | | 0.2423 | Heat shock protein HSP 90-alpha |
| MDHM | P40926 | | 0.1712 | Malate dehydrogenase, mitochondrial |
| 1433G | P61981 | | 0.1608 | 14-3-3 protein gamma |
| KCRU | P12532 | | 0.3709 | Creatine kinase U-type, mitochondrial |
| MGST1 | P10620 | | 0.4115 | Microsomal glutathione S-transferase 1 |
| PLST | P13797 | | 0.3280 | Plastin-3 |
| TENX | P22105-3 | | 0.3180 | Tenascin-X |
| GSTP1 | P09211 | | 0.7356 | Glutathione S-transferase P |
| SPB5 | P36952-2 | | 0.7185 | Serpin B5 |
| K1C17 | Q04695 | | 0.4547 | Keratin, type I cytoskeletal 17 |
| CH10 | P61604 | | 0.7309 | 10 kDa heat shock protein, mitochondrial |
| K2C5 | P13647 | | 0.9602 | Keratin, type II cytoskeletal 5 |
| K2C75 | O95678 | | 0.7730 | Keratin, type II cytoskeletal 75 |
| KRHB4 | Q9NSB2 | | 0.2100 | Keratin, type II cuticular Hb4 |
| ACSL1 | P33121-2 | | 0.2422 | Long-chain-fatty-acid--CoA ligase 1 |
| PEBP1 | P30086 | | 0.1779 | Phosphatidylethanolamine-binding protein 1 |
| CH60 | P10809 | | 0.2522 | 60 kDa heat shock protein, mitochondrial |

TABLE 4-continued

List of SWATH-MS-identified proteins and DE candidates from FFP PWS samples

| Protein | Protein ID | Changes | T-test p value | Protein full name |
|---|---|---|---|---|
| EF2 | P13639 | | 0.8619 | Elongation factor 2 |
| G3P | P04406 | | 0.1730 | Glyceraldehyde-3-phosphate dehydrogenase |
| ROA2 | P22626-2 | | 0.0821 | Heterogeneous nuclear ribonucleoproteins A2/B1 |
| SAMP | P02743 | | 0.5089 | Serum amyloid P-component |
| ACTN4 | O43707 | | 0.1769 | Alpha-actinin-4 |
| CO7A1 | Q02388-2 | | 0.3306 | Collagen alpha-1(VII) chain |
| ANXA2 | P07355 | | 0.0670 | Annexin A2 |
| TPM4 | P67936 | | 0.8825 | Tropomyosin alpha-4 chain |
| K2C7 | P08729 | | 0.1376 | Keratin, type II cytoskeletal 7 |
| TAGL2 | P37802 | | 0.6384 | Transgelin-2 |
| TAGL | Q01995 | | 0.9556 | Transgelin |
| DESP | P15924 | | 0.8624 | Desmoplakin |
| KRHB1 | Q14533 | | 0.6614 | Keratin, type II cuticular Hb1 |
| ATPD | P30049 | | 0.9944 | ATP synthase subunit delta, mitochondrial |
| H13 | P16402 | | 0.7264 | Histone H1.3 |
| PKP1 | Q13835-2 | | 0.4539 | Plakophilin-1 |
| Q6ZN40 | Q6ZN40 | | 0.7311 | Tropomyosin 1 (Alpha), isoform CRA_f |
| VINC | P18206-2 | | 0.3318 | Vinculin |
| TPM3 | P06753-2 | | 0.9364 | Tropomyosin alpha-3 chain |
| MYH9 | P35579 | | 0.6876 | Myosin-9 |
| QCR2 | P22695 | | 0.0904 | Cytochrome b-c1 complex subunit 2, mitochondrial |
| HMCS1 | Q01581 | | 0.1303 | Hydroxymethylglutaryl-CoA synthase, cytoplasmic |
| PTRF | Q6NZI2 | | 0.1133 | Caveolae-associated protein 1 |
| I3L1M0 | UPI0001E6F9D7 | | 0.5223 | |
| FIBG | P02679-2 | | 0.5412 | Fibrinogen gamma chain |
| CBR1 | P16152 | | 0.5535 | Carbonyl reductase [NADPH] 1 |
| IGHV1-69 | P01742 | | 0.3966 | Immunoglobulin heavy variable 1-69 |
| AK1A1 | P14550 | | 0.3532 | Alcohol dehydrogenase [NADP(+)] |
| RS7 | P62081 | | 0.0898 | 40S ribosomal protein S7 |
| 6PGD | P52209 | | 0.1932 | 6-phosphogluconate dehydrogenase, decarboxylating |
| K1HB | Q14525 | | 0.7606 | Keratin, type I cuticular Ha3-II |
| RINI | P13489 | | 0.4873 | Ribonuclease inhibitor |
| KRHB5 | P78386 | | 0.3782 | Keratin, type II cuticular Hb5 |
| ACTA | P62736 | | 0.3669 | Actin, aortic smooth muscle |
| 1433T | P27348 | | 0.5399 | 14-3-3 protein theta |
| 1433S | P31947-2 | | 0.1912 | 14-3-3 protein sigma |
| KT33A | O76009 | | 0.5778 | Keratin, type I cuticular Ha3-I |
| ANXA4 | P09525 | | 0.3965 | Annexin A4 |
| COF1 | P23528 | | 0.1697 | Cofilin-1 |
| DCD | P81605-2 | | 0.3436 | Dermcidin |
| MYL6 | P60660-2 | | 0.4113 | Myosin light polypeptide 6 |
| CO3 | P01024 | | 0.3680 | Complement C3 |
| ALDOA | P04075 | | 0.7189 | Fructose-bisphosphate aldolase A |
| F8WA83 | F8WA83 | | 0.1590 | Protein disulfide-isomerase A6 |
| RS25 | P62851 | | 0.6396 | 40S ribosomal protein S25 |
| RLA0 | P05388 | | 0.8649 | 60S acidic ribosomal protein P0 |
| FPPS | P14324 | | 0.6824 | Farnesyl pyrophosphate synthase |
| SODE | P08294 | | 0.7150 | Extracellular superoxide dismutase [Cu—Zn] |
| PDIA3 | P30101 | | 0.3960 | Protein disulfide-isomerase A3 |
| H2AZ | P0C0S5 | | 0.2815 | Histone H2A.Z |
| CO6A2 | P12110 | | 0.07811 | Collagen alpha-2(VI) chain |
| UBB | P0CG47 | | 0.2636 | Polyubiquitin-B |
| H14 | P10412 | | 0.7302 | Histone H1.4 |
| H12 | P16403 | | 0.9632 | Histone H1.2 |
| PPIB | P23284 | | 0.0415 | Peptidyl-prolyl cis-trans isomerase B |
| IGHA1 | P01876 | | 0.0592 | Immunoglobulin heavy constant alpha 1 |
| PRDX2 | P32119 | | 0.2307 | Peroxiredoxin-2 |
| TETN | P05452 | | 0.6625 | Tetranectin |
| CO2A1 | P02458-1 | | 0.7240 | Collagen alpha-1 (II) chain |
| PGS1 | P21810 | | 0.6091 | Biglycan |
| PLSL | P13796 | | 0.2034 | Plastin-2 |

TABLE 4-continued

List of SWATH-MS-identified proteins and DE candidates from FFP PWS samples

| Protein | Protein ID | Changes | T-test p value | Protein full name |
|---|---|---|---|---|
| K1C16 | P08779 | | 0.1750 | Keratin, type 1 cytoskeletal 16 |
| TERA | P55072 | | 0.3518 | Transitional endoplasmic reticulum ATPase |
| IF4A1 | P60842 | | 0.5670 | Eukaryotic initiation factor 4A-I |
| ALDH2 | P05091 | | 0.1389 | Aldehyde dehydrogenase, mitochondrial |
| F213A | Q9BRX8-2 | | 0.3071 | Redox-regulatory protein FAM213A |
| TRFE | P02787 | | 0.9619 | Serotransferrin |
| DLDH | P09622 | | 0.1199 | Dihydrolipoyl dehydrogenase, mitochondrial |
| HBA | P69905 | | 0.6317 | Hemoglobin subunit alpha |
| ADT2 | P05141 | | 0.1362 | ADP/ATP translocase 2 |
| S10A4 | P26447 | | 0.2537 | Protein S100-A4 |
| K2C6A | P02538 | | 0.7811 | Keratin, type II cytoskeletal 6A |
| K2C71 | Q3SY84 | | 0.3118 | Keratin, type II cytoskeletal 71 |
| FIBA | P02671-2 | | 0.8840 | Fibrinogen alpha chain |
| RAB1A | P62820 | | 0.1385 | Ras-related protein Rab-1A |
| PRDX3 | P30048 | | 0.5286 | Thioredoxin-dependent peroxide reductase |
| HNRPM | P52272-2 | | 0.1103 | Heterogeneous nuclear ribonucleoprotein M |
| COEA1 | Q05707-2 | | 0.1047 | Collagen alpha-1(XIV) chain |
| CATD | P54720 | | 0.5173 | Putative oxidoreductase CatD |
| CYTB | P04080 | | 0.2558 | Cystatin-B |
| HBD | P02042 | | 0.8510 | Hemoglobin subunit delta |
| COCA1 | Q99715-4 | | 0.2653 | Collagen alpha-1 (XII) chain |
| PARK7 | Q99497 | | 0.5698 | Protein DJ-1 |
| HBB | P68871 | | 0.7369 | Hemoglobin subunit beta |
| H4 | P62805 | | 0.5921 | Histone H4 |
| PLAK | P14923 | | 0.0868 | Junction plakoglobin |
| FADS2 | O95864-3 | | 0.2638 | Fatty acid desaturase 2 |
| VIME | P08670 | | 0.2791 | Vimentin |
| GDIB | P50395 | | 0.4545 | Rab GDP dissociation inhibitor beta |
| AMBP | P02760 | | 0.2800 | Protein AMBP |
| ACADM | P11310-2 | | 0.1668 | Medium-chain specific acyl-CoA dehydrogenase |
| AHNK | Q09666 | | 0.2044 | Neuroblast differentiation-associated protein AHNAK |
| RL11 | P62913-2 | | 0.5031 | 60S ribosomal protein L11 |
| BLVRB | P30043 | | 0.9121 | Flavin reductase (NADPH) |
| 1433B | P31946-2 | | 0.1837 | 14-3-3 protein beta/alpha |
| LEG7 | P47929 | | 0.2234 | Galectin-7 |
| LX15B | O15296-3 | | 0.9051 | Arachidonate 15-lipoxygenase B |
| E7EN67 | E7EN67 | | 0.2188 | |
| RSSA | P08865 | | 0.2774 | 40S ribosomal protein SA |
| H2B1K | O60814 | | 0.2670 | Histone H2B type 1-K |
| PRDX1 | Q06830 | | 0.3174 | Peroxiredoxin-1 |
| GRP78 | P11021 | | 0.1801 | 78 kDa glucose-regulated protein |
| F13A | P00488 | | 0.4218 | Coagulation factor XIII A chain |
| ACTN1 | P12814-2 | | 0.5855 | Alpha-actinin-1 |
| A1AT | P01009-2 | | 0.3595 | Alpha-1-antitrypsin |
| ALBU | P02768 | | 0.6580 | Serum albumin |
| CO3A1 | P02461 | | 0.8563 | Collagen alpha-1(III) chain |
| PLIN3 | O60664-3 | | 0.1000 | Perilipin-3 |
| HV305 | P01766 | | 0.0699 | Immunoglobulin heavy variable 3-13 |
| 1433E | P62258-2 | | 0.1358 | 14-3-3 protein epsilon |
| DEST | P60981-2 | | 0.7139 | Destrin |
| SERA | O43175 | | 0.0964 | D-3-phosphoglycerate dehydrogenase |
| PYGB | P11216 | | 0.5287 | Glycogen phosphorylase, brain form |
| FLNA | P21333-2 | | 0.1114 | Filamin-A |
| KCD12 | Q96CX2 | | 0.0769 | BTB/POZ domain-containing protein KCTD12 |
| ENPL | P14625 | | 0.1996 | Endoplasmin |
| HEMO | P02790 | | 0.9227 | Hemopexin |
| K1C14 | P02533 | | 0.2896 | Keratin, type I cytoskeletal 14 |
| K2C8 | P05787 | | 0.1272 | Keratin, type II cytoskeletal 8 |
| FAS | P49327 | | 0.0829 | Fatty acid synthase |
| RAB7A | P51149 | | 0.7764 | Ras-related protein Rab-7a |
| K1C15 | P19012 | | 0.5779 | Keratin, type I cytoskeletal 15 |
| TBAL3 | A6NHL2-2 | | 0.9280 | Tubulin alpha chain-like 3 |

TABLE 4-continued

List of SWATH-MS-identified proteins and DE candidates from FFP PWS samples

| Protein | Protein ID | Changes | T-test p value | Protein full name |
|---|---|---|---|---|
| ANXA4 | P09525 | | 0.3780 | Annexin A4 |
| H10 | P07305-2 | | 0.5124 | Histone H1.0 |
| H2A1B | P04908 | | 0.2242 | Histone H2A type 1-B/E |
| GELS | P06396 | | 0.2569 | Gelsolin |
| EF1A1 | P68104 | | 0.1503 | Elongation factor 1-alpha 1 |
| GLRX1 | P35754 | | 0.7463 | Glutaredoxin-1 |
| IDHP | P48735 | | 0.1151 | Isocitrate dehydrogenase [NADP], mitochondrial |
| HNRPK | P61978-2 | | 0.8073 | Heterogeneous nuclear ribonucleoprotein K |
| K1C19 | P08727 | | 0.6558 | Keratin, type I cytoskeletal 19 |
| AL9A1 | P49189 | | 0.6336 | 4-trimethylaminobutyraldehyde dehydrogenase |
| CLIC1 | O00299 | | 0.5148 | Chloride intracellular channel protein 1 |
| DPYL2 | Q16555 | | 0.74210 | Dihydropyrimidinase-related protein 2 |
| AN32A | P39687 | | 0.3995 | Acidic leucine-rich nuclear phosphoprotein 32 family member A |
| LMNA | P02545 | | 0.2599 | Prelamin-A/C |
| PROF1 | P07737 | | 0.1528 | Profilin-1 |
| 1433Z | P63104 | | 0.1740 | 14-3-3 protein zeta/delta |
| RL22 | P35268 | | 0.8040 | 60S ribosomal protein L22 |
| K1H1 | Q15323 | | 0.7391 | Keratin, type I cuticular Ha1 |
| F5GWP8 | F5GWP8 | | 0.6802 | Keratin, type I cytoskeletal 17 |
| BGH3 | Q15582 | | 0.2281 | Transforming growth factor-beta-induced protein ig-h3 |

Figure 6A:
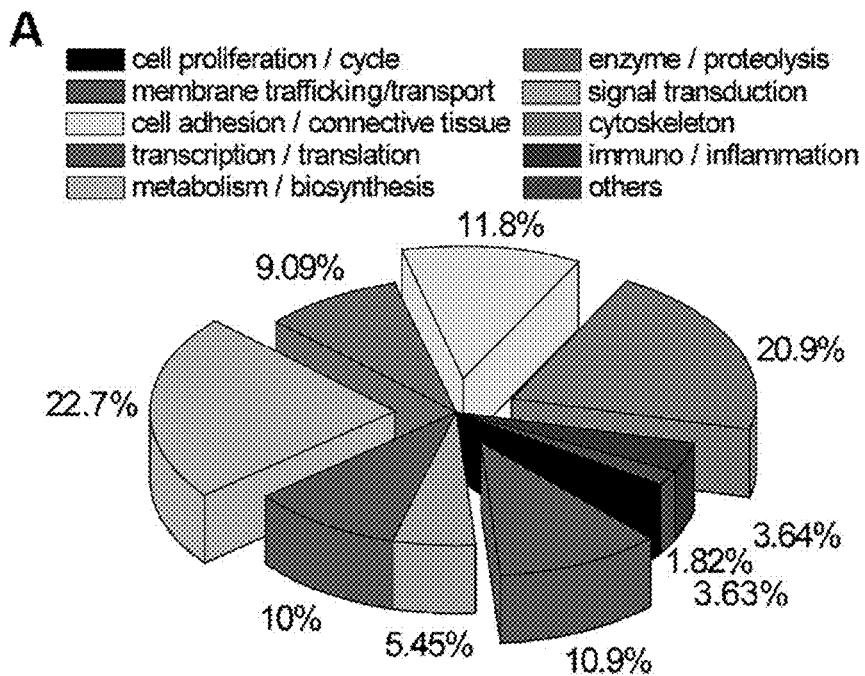
FIG. 6A-C demonstrates that exocytotic proteins are upregulated in PWS lesions. (A) Functional categories of 107 DE proteins identified by SWATH-MS from PWS FFPE sections (n=6 subjects) as compared to the control (n=3 subjects). (B) Immunoblot analysis to further verify the expression patterns of some DE exocytotic and collagenous proteins in PWS hypertrophic lesions and nodules as compared to the control. GAPDH was used as the loading control. H, hypertrophic lesions; N, nodules. (C) Fold changes of protein expression levels in PWS hypertrophic lesions and nodules as compared to the control. The data (means±SD, n=3-6) were normalized to GAPDH and the expression levels of all proteins in the control were set as 1 (dash line). #p<0.05 compared to control.
Figure 6B:
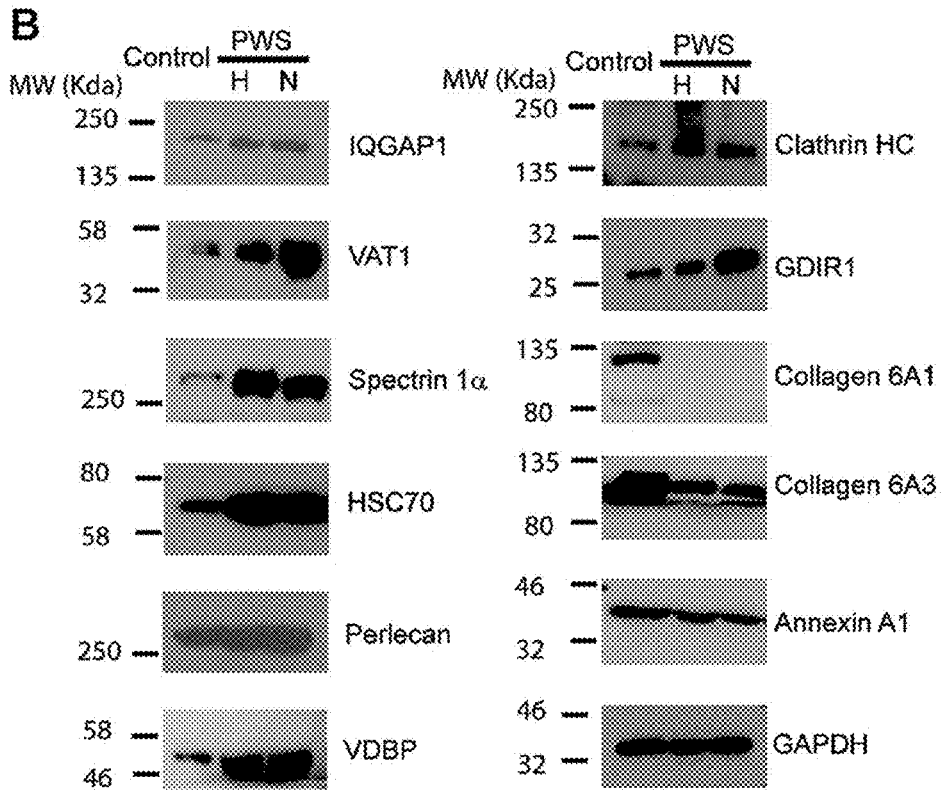
Figure 6C:
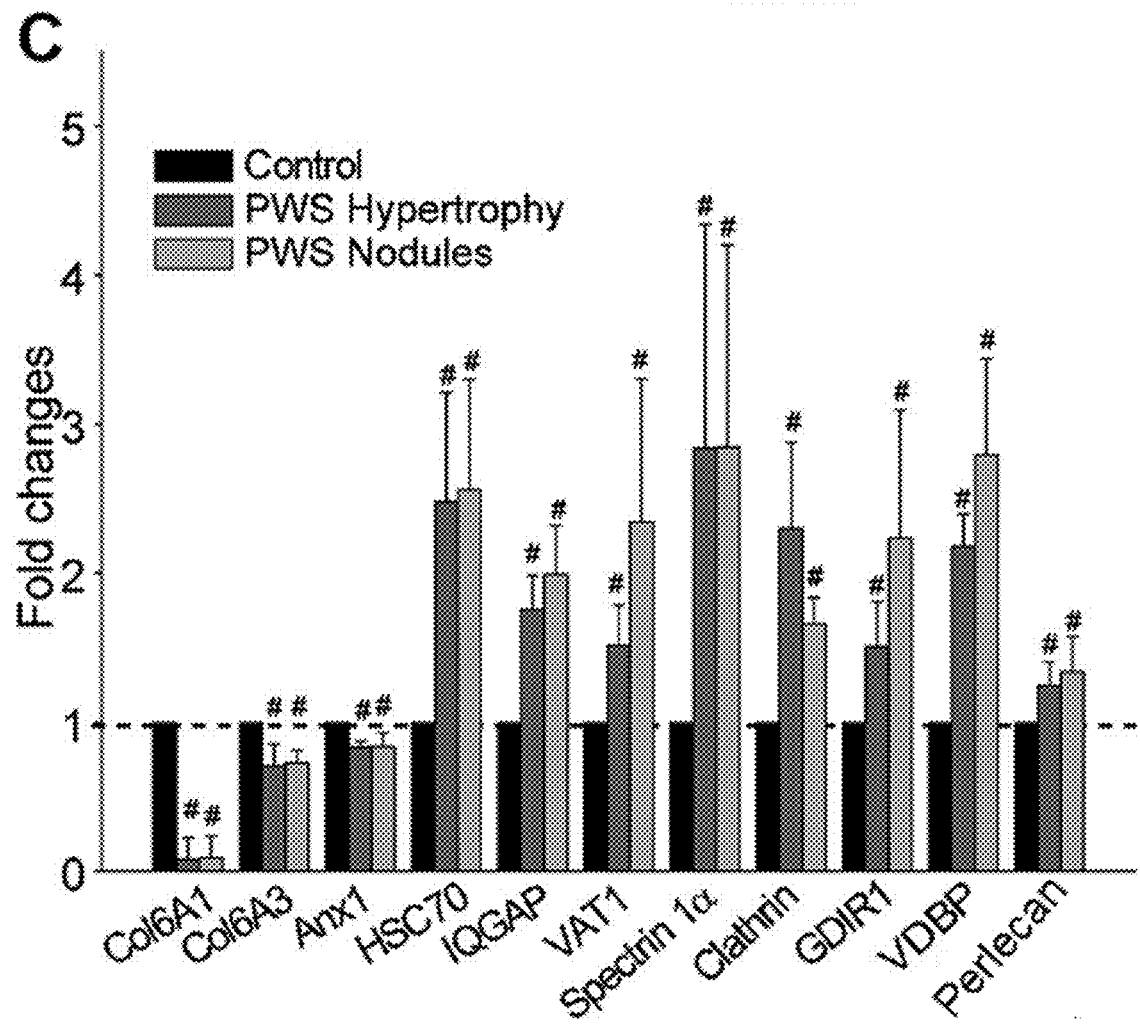

Metabolism/biosynthesis, cytoskeleton, cell adhesion/connective tissue and membrane trafficking were the leading functional categories of these DE proteins, accounting for 24.7%, 20.9%, 11.9% and 10.9% of total 107 DE proteins, respectively (see FIG. 6A).

Verifying Expression of Select Molecules Related to Adhesion/Migration/Exocytosis by Immunoblot.

An immunoblot assay was then performed to verify the expression levels of some key molecules with functions related to cell adhesion/migration/exocytosis, including IQGAP1, VAT1, spectrin 1α, clathrin, GDIR1, HSC70 and perlecan. It was found that the expression levels of all of these proteins showed a significant increase in PWS hypertrophic lesions and nodules as compared to control (see FIGS. 6B and 6C). In addition, it was confirmed that the expression of VDBP was significantly higher in PWS hypertrophic lesions and nodules as compared to control. The expressions of Col6A1, Col6A3 and Anx1 showed significant decreases in PWS lesions as compared to control (see FIGS. 6B and 6C). These results were consistent with the SWATH-MS data (see Table 4)

Figure 7:
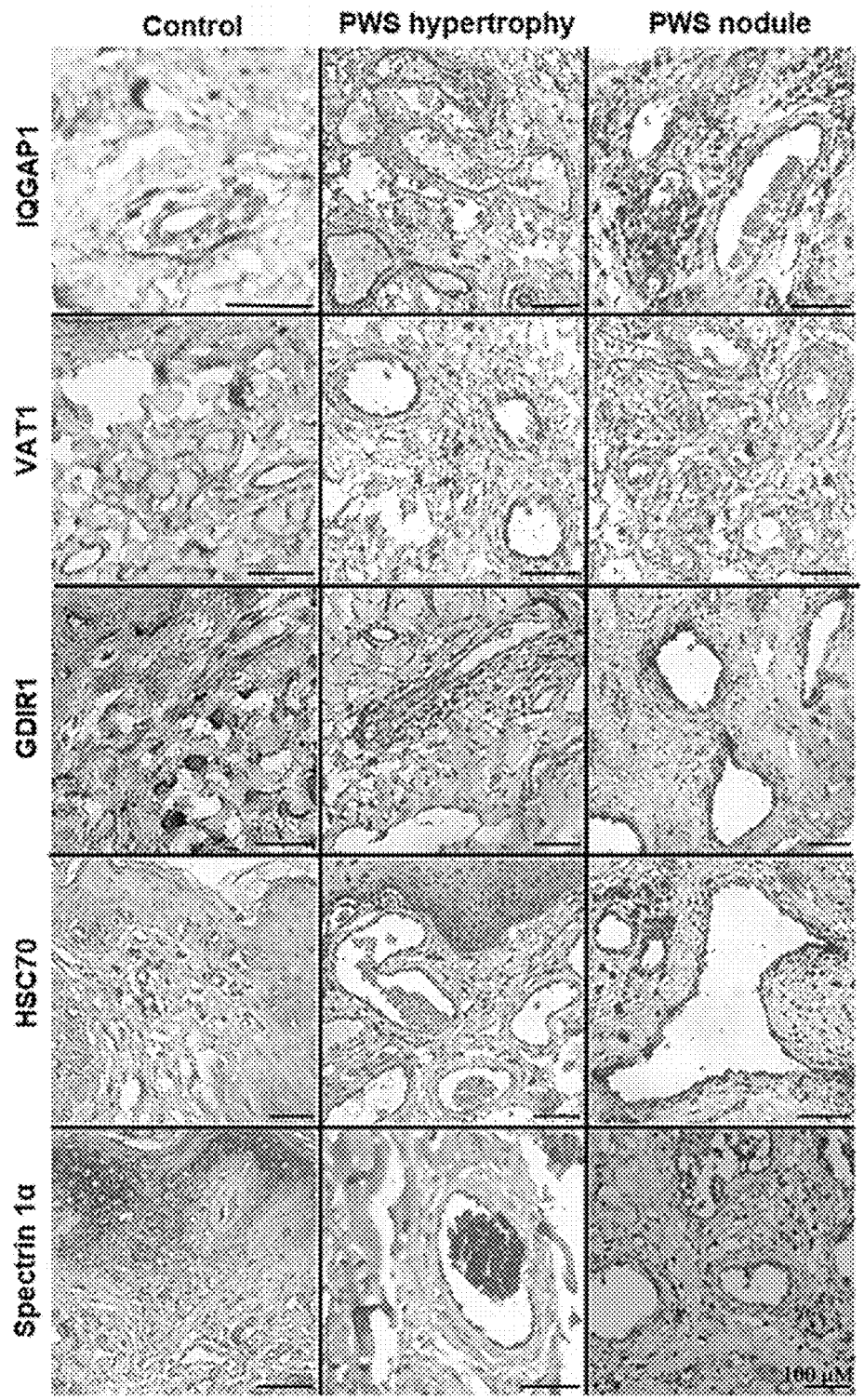
FIG. 7 indicates the immunohistochemical localization of increased IQGAP1, VAT1, GDIR1, HSC70 and spectrin 1α proteins in blood vessels of PWS hypertrophic lesions and nodules as compared to normal skin control. Scale bar: 100 μM.

Determining the cellular localization of IQGAP1, VAT1, GDIR1, HSC70 and spectrin 1α in PWS lesons by IHC IQGAP1, VAT1, GDIR1, HSC70 and Spectrin 1α showed a negative or mild expression in normal dermal blood vessels (see FIG. 7). In PWS hypertrophic lesions and nodules, all of these proteins were strongly expressed in endothelial cells (ECs). IQGAP1, VAT1, GDIR1 and HSC70 also showed a strong immuno-reactive (IR) signal in pericytes and some fibroblasts (see FIG. 7). In PWS nodules, the synaptic protein VAT1 expression extended throughout the entire PWS blood vessel stroma, showing a membrane pattern (see FIG. 7). The upregulation of a variety of membrane trafficking 174 related proteins in PWS lesions led us to posit that PWS ECs may aberrantly secrete EVs.

Examining the Fine Structures of PWS as Compared to Normal Dermal Vessels Using TEM Studies.

A large number of EVs actively budding off from the PWS vessel wall into the lumen in both infantile and adult PWSs was observed (see FIGS. 8A-C). The quantity of EVs released from PWS blood vessels showed a significant increase by 2.8-fold as compared to control vessels (1.4107±0.6309 vs 0.3196±0.2384 per unit length (μm) of endothelium, p=0.0152, n=6 subjects) (see FIG. 8D). Furthermore, the average diameter of EVs released from PWS is slightly, but significantly larger, than control vessels (0.3494±0.1495 vs 0.30118±0.1793 μm, p=0.0472, n=6 subjects) (see FIG. 8E). The findings suggest that PWS blood vessel ECs actively secrete more and larger EVs as compared to controls, demonstrating the aberrant upregulation of exocytosis pathways in PWS blood vessels.

A number of embodiments have been described herein. Nevertheless, it will be understood that various modifications may be made without departing from the spirit and scope of this disclosure. Accordingly, other embodiments are within the scope of the following claims.

What is claimed is:

1. A method comprising:
  obtaining a skin tissue biopsy sample(s) and/or extracellular vesicle (EV) serum sample(s) from a subject suspected of having or having a vascular anomaly or malformation selected from the group consisting of arterio-venous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, Dural AV fistula, and angiokeratoma;
  measuring the expression profile of a set of pathogenic associated biomarkers and/or serum EV biomarkers from the sample(s) obtained from the subject, wherein the set of pathogenic associated biomarkers and/or serum EV biomarkers comprises VAT1, IQGAP1, HSC70, CLH1, perlecan, spectrin α1, and GDIR1;

comparing the expression profile of the set pathogenic associated biomarkers and/or serum EV biomarkers from the subject's skin tissue biopsy sample(s) and/or EV serum sample(s) with the expression profile of the same set pathogenic associated biomarkers and/or serum EV biomarkers from control skin tissue biopsy sample(s) and/or EV serum sample(s) that do not have the vascular anomaly or malformation; and treating the subject with a pulsed dye laser or intense pulsed light, based upon a significant difference in the protein expression profile of the set biomarkers from the subject samples in comparison with control skin tissue biopsy sample(s) and/or EV serum sample(s).

2. The method of claim 1, wherein the set of pathogenic associated biomarkers and/or serum EV biomarkers further comprises one or more biomarkers selected from Ephs, Efns ADAMs, MMPs, STYs, CD31, CD133, CD166, VDBP, ANXA1, CO6A1 and/or CO6A3.

3. The method of claim 1, wherein the expression profile of the set of pathogenic associated biomarkers and/or serum EV biomarkers is measured using sequential windowed acquisition of all theoretical fragment ion mass spectra (SWATH-MS), immunohistochemistry, immunoblot, and/or transmission electron microscopy.

4. The method of claim 1, further comprising:
treating the subject with one or more treatments for vascular anomalies or malformations wherein the subject has a vascular anomaly or malformation selected from the group consisting of AVM, VM, PWS, SWS, KTWS, hemangioma, cavernoma, capillary telangiectasia, Dural AV fistula, and angiokeratoma;

obtaining a second skin tissue biopsy sample(s) and/or EV serum sample(s) from the subject after treatment, where the skin tissue biopsy sample(s) and/or EV serum sample(s) are from the same general area as the sample(s) obtained prior to treatment;

measuring a second expression profile of the set of pathogenic associated biomarkers and/or serum EV biomarkers from the subject's skin tissue biopsy sample(s) and/or EV serum sample(s) obtained after treatment;

comparing the expression profile of the set of pathogenic associated biomarkers and/or serum EV biomarkers prior to treatment with the second expression profile of the set pathogenic associated biomarkers and/or serum EV biomarkers after treatment, wherein the same set of pathogenic associated biomarkers and/or serum EV biomarkers are compared between the expression profiles; and identifying whether the treatment for the vascular anomalies or malformations was effective based upon an improvement in the second expression profile for the biomarkers after treatment in comparison with the expression profile of the biomarkers prior to treatment.

5. The method of claim 4, wherein the one or more treatments for vascular anomalies or malformations are small molecule drugs or therapies that inhibit or disrupt EphB1/EfnB2 signaling pathways.

6. The method of claim 4, wherein the one or more treatments for vascular anomalies or malformations are small molecule drugs or therapies that inhibit or disrupt or suppress exocytosis from lesional vasculatures by inhibiting or disrupting the expression of exocytotic proteins.

7. The method of claim 1, wherein the pathogenic associated biomarkers and/or serum extracellular vesicle (EV) biomarkers are used to quantify protein expression.

8. A method comprising:
treating a subject having vascular anomalies or malformations selected from the group consisting of arteriovenous malformations (AVM), venous malformations (VM), port-wine stain (PWS), Sturge-Weber syndrome (SWS), Klippel-Trenaunay-Weber syndrome (KTWS), hemangioma, cavernoma, capillary telangiectasia, dural AV fistula, and angiokeratoma with one or more treatments for the vascular anomalies or malformations;

obtaining a skin tissue biopsy sample(s) and/or extracellular vesicle (EV) serum sample(s) from the subject at the site of the vascular anomaly or malformation;

measuring the expression profile of a set of pathogenic associated biomarkers and/or serum EV biomarkers from sample(s) obtained from the subject, wherein the set of pathogenic associated biomarkers and/or serum EV biomarkers comprises VAT1, IQGAP1, HSC70, CLH1, perlecan, spectrin α1, and GDIR1;

comparing the expression profile of the set pathogenic associated biomarkers and/or serum EV biomarkers from the subject's skin tissue biopsy sample(s) and/or EV serum sample(s) with the expression profile of the same set pathogenic associated biomarkers and/or serum EV biomarkers from control skin tissue biopsy sample(s) and/or EV serum sample(s) that do not have a vascular anomaly or malformation;

identifying that the treatment for vascular anomalies or malformations in the subject was effective based upon measuring an improvement in the expression levels of the set of pathogenic associated biomarkers and/or serum EV biomarkers in the subject's sample(s).

9. The method of claim 8, wherein the set of pathogenic associated biomarkers and/or serum EV biomarkers further comprises one or more biomarkers selected from Ephs, Efns, ADAMs, MMPs, STYs, CD31, CD133, CD166, VDBP, ANXA1, CO6A1 and/or CO6A3.

10. The method of claim 8, wherein the expression profile of the set of pathogenic associated biomarkers and/or serum EV biomarkers is measured using sequential windowed acquisition of all theoretical fragment ion mass spectra (SWATH-MS), immunohistochemistry, immunoblot, and/or transmission electron microscopy.

11. The method of claim 8, wherein the one or more treatments are small molecule drugs or therapies, gene silencing agents or surface targeting ligands.

12. The method of claim 11, wherein the gene silencing agents are antisense oligonucleotides, ribozymes, RNA interference, microRNAs, and/or CRISPR.

13. The method of claim 11, wherein the surface targeting ligands bind or complex with CD133, CD166, EphB1, and/or EfnB2.

14. The method of claim 11, wherein the small molecule drugs or therapies inhibit or disrupt EphB1/EfnB2 signaling pathways.

15. The method of claim 11, wherein the small molecule drugs or therapies disrupt or suppress exocytosis from lesional vasculatures by inhibiting or disrupting the expression of exocytotic proteins.

16. The method of claim 8, wherein the one or more treatments are pulsed dye laser, intense pulsed light, surgery, radiation, and/or freezing.

* * * * *